United States Patent
Wu et al.

(10) Patent No.: US 9,284,315 B2
(45) Date of Patent: Mar. 15, 2016

(54) THREE-RING PI3K AND/OR MTOR INHIBITOR

(71) Applicant: XUANZHU PHARMA CO., LTD., Jinan (CN)

(72) Inventors: Frank Wu, Jinan (CN); Yan Zhang, Jinan (CN)

(73) Assignee: ZUANZHU PHARMA CO., LTD., Jinan (CN)

( * ) Notice: Subject to any disclaimer, the term of this patent is extended or adjusted under 35 U.S.C. 154(b) by 0 days.

(21) Appl. No.: 14/358,906

(22) PCT Filed: Nov. 16, 2012

(86) PCT No.: PCT/CN2012/001551
§ 371 (c)(1),
(2) Date: May 16, 2014

(87) PCT Pub. No.: WO2013/071698
PCT Pub. Date: May 23, 2013

(65) Prior Publication Data
US 2015/0166539 A1    Jun. 18, 2015

(30) Foreign Application Priority Data

Nov. 17, 2011   (CN) .......................... 2011 1 0364054
Mar. 20, 2012   (CN) .......................... 2012 1 0072834

(51) Int. Cl.
| | | |
|---|---|---|
| *C07D 471/14* | (2006.01) | |
| *C07D 519/00* | (2006.01) | |
| *A61K 31/519* | (2006.01) | |
| *A61K 31/5377* | (2006.01) | |
| *A61K 45/06* | (2006.01) | |

(52) U.S. Cl.
CPC ............ *C07D 471/14* (2013.01); *A61K 31/519* (2013.01); *A61K 31/5377* (2013.01); *A61K 45/06* (2013.01); *C07D 519/00* (2013.01)

(58) Field of Classification Search
CPC .. C07D 471/14; C07D 519/00; A61K 31/519; A61K 31/5377; A61K 45/06
See application file for complete search history.

(56) References Cited

FOREIGN PATENT DOCUMENTS

| | | |
|---|---|---|
| CN | 102399220 | 4/2012 |
| CN | 102399220 A * | 4/2012 |
| WO | 2005047285 | 5/2005 |
| WO | 2006/122806 A2 | 11/2006 |
| WO | 2010/044885 A2 | 4/2010 |
| WO | 2010/139731 A1 | 12/2010 |

OTHER PUBLICATIONS

CAS STN Abstract for RN 1370640-12-2, Apr. 26, 2012.*
Sonpavde et. al., Current Oncology Reports, 2007, Current Medicine Group LLC, vol. 9, pp. 115-119.*
Japanese Application No. 2014-541506, Office Action mailed Mar. 2, 2015, 7 pages.
International Application No. PCT/CN2012/001551, International Search Report dated Feb. 14, 2013.
EP Application No. 12 84 9086.9, Extended Search Report mailed Jun. 10, 2015, 5 pages.

* cited by examiner

*Primary Examiner* — Sarah Pihonak
(74) *Attorney, Agent, or Firm* — Kilpatrick Townsend & Stockton LLP

(57) ABSTRACT

The present application relates to a compound as represented by general formula (I), a pharmaceutically acceptable salt, ester, solvate or stereoisomer thereof, preparation method of the compounds, a pharmaceutical composition containing the compounds, uses thereof in the preparation of drugs for treating and/or preventing proliferative diseases, and a method using the compounds to treat and/or prevent proliferative diseases. $R^1$, $R^2$, $R^3$, $R^4$, $R^5$, $R^6$, X, A and B in the formula are as defined in the specification.

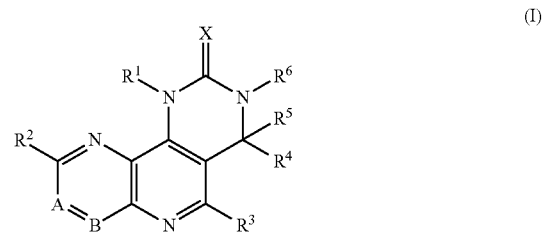

8 Claims, No Drawings ically acceptable salt, ester, solvate or stereoisomer thereof, a method for preparing these compounds, a pharmaceutical composition comprising the same, as well as a use of these compounds in the manufacture of a medicament for treating and/or preventing proliferative diseases.

BACKGROUND ART

Tumors are new creatures formed in the body due to actions of a variety of oncogenic factors and the following changes of genetic material of cells resulting in abnormal gene expression and cell proliferation. The tumor cells lose their normal growth regulatory function and have autonomous or relatively autonomous growth ability. The tumor cells can continue to grow even the oncogenic factors disappear and will cause a consumption of large quantities of human's nutrients. If not being found and treated early, the cancer cells will be transferred and grow throughout the body, and release a variety of toxins that cause the body weight loss, anemia, organ failure and even death.

The method of treating tumors mainly includes three aspects: drug therapy, surgery and radiation therapy. Drug therapy is becoming increasingly important in cancer treatment since surgery and radiation therapy are difficult to eradicate the tumor and fail to show obvious effect in patients with the mid-advanced cancer. Conventional anticancer drugs do not distinguish between tumor cells and normal cells, and often cause serious side effects. Targeted drugs specifically target to cancer cells and can accurately act on the tumor, which greatly improves the level of treatment and reduces the adverse response rate, such as making the median survival time of patients with advanced colorectal cancer increased 66.7%, and the efficiency of the treatment of advanced breast cancer increased 71.3%.

As pharmaceutical companies are accelerating the development of targeted antineoplastic drugs, and there is a great market demand for this class of antineoplastic drugs, molecular targeted drugs have become the world's fastest growing unit in the worldwide market.

Phosphatidylinositol 3-kinase (PI3K) pathway is the most common place where human cancer cells mutate, and it can lead to cell proliferation, activation and signal amplification. PI3K and mammalian target of rapamycin (mTOR) are important kinases of PI3K signaling pathway.

PI3K is a member of lipid kinase family, it regulates cell metabolism and growth through phosphorylation at 3-position of phosphatidylinositol to produce phosphatidylinositol-triphosphate (PIP3). This PIP3, which is the second messenger of lipid, can make PI3K paired with downstream effectors (especially Akt), resulting in membrane recruitment and phosphorylation, cell proliferation and activation. Therefore, inhibition of phosphatidylinositol 3-kinase can affect the PI3K pathway, thereby inhibiting cancer cell proliferation and activation.

mTOR is a serine/threonine protein kinase present in the cytoplasm, it belongs to the phosphoinositide 3-kinase-related protein kinase family and exists in organism as two complexes forms, namely mTORC1 (rapamycin target) and mTORC2 (not inhibited by rapamycin). mTOR is a cellular signal transduction protein, which regulates the response of tumor cells to nutrients and growth factors, and controls tumor blood supply through the role of vascular endothelial growth factor. mTOR inhibitors can make cancer cells starved, and reduce the tumor volume by inhibiting mTOR.

In Novartis' patent application of WO2006122806 and Pfizer's patent application of WO201003816, a series of compounds inhibiting both PI3K and mTOR have been reported. These compounds have good activity in tumor therapy. However, there is no compound inhibiting both PI3K and mTOR on the current drug market. Therefore, it is needed to develop multi-targeted drugs that have inhibiting activity for both PI3K and mTOR in order to facilitate the treatment of cancer.

SUMMARY OF THE INVENTION

The object of the present invention is to provide a PI3K and/or mTOR inhibitor. Specifically, the present invention relates to:

(1) A compound of general formula (I):

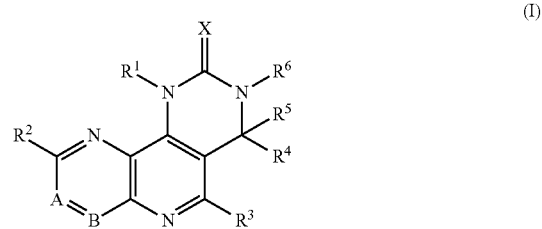

or a pharmaceutically acceptable salt, ester, solvate or stereoisomer thereof,
wherein
X is O or S;
A and B are each $CR^8$, $R^8$ is hydrogen, halogen, cyano, hydroxy, carboxyl, $-(CH_2)_nNR^{10a}R^{10b}$, $-(CH_2)_nC(O)R^{11}$, $-(CH_2)_nS(O)_mR^{11}$, $-(CH_2)_nS(O)_mNR^{10a}R^{10b}$, $-(CH_2)_nN(R^{10a})S(O)_mR^{11}$, $-(CH_2)_nC(O)NR^{10a}R^{10b}$, $-(CH_2)_nOC(O)R^{11}$, $-(CH_2)_nC(O)(CH_2)_nOR^{11}$, $-(CH_2)_nN(R^{10a})C(O)R^{11}$, $C_{1-6}$ alkyl or $C_{1-6}$ alkoxy, wherein $C_{1-6}$ alkyl and $C_{1-6}$ alkoxy may be optionally substituted with 1 to 3 substituents selected from halogen, hydroxy and carboxyl;

$R^1$ is hydrogen, or $C_{1-6}$ alkyl, $C_{2-8}$ alkenyl, $C_{2-8}$ alkynyl, $C_{3-8}$ cycloalkyl, 6- to 14-membered aryl, 5- to 14-membered heteroaryl, 3- to 14-membered heterocyclic group, 7- to 12-membered spirocyclic group or 7- to 12-membered endocyclic group, all of which except hydrogen may be optionally substituted with 1 to 5 $R^{9a}$;

$R^2$ is hydrogen, $C_{1-6}$ alkyl, $C_{2-8}$ alkenyl, $C_{2-8}$ alkynyl, $C_{3-8}$ cycloalkyl, 6- to 14-membered aryl, 5- to 14-membered heteroaryl, 3- to 14-membered heterocyclic group, 7- to 12-membered spirocyclic group or 7- to 12-membered endocyclic group, all of which except hydrogen may be optionally substituted with 1 to 5 $R^{9b}$;

$R^3$ is hydrogen, carboxyl or $C_{1-6}$ alkyl, wherein $C_{1-6}$ alkyl may be optionally substituted with 1 to 3 substituents selected from halogen, hydroxy and carboxyl;

$R^4$ and $R^5$ are each independently hydrogen or $C_{1-6}$ alkyl, wherein $C_{1-6}$ alkyl may be optionally substituted with 1 to 3 substituents selected from halogen, hydroxy and carboxyl; or $R^4$ and $R^5$ combine each other to form $C_{3-8}$ cycloalkyl, 5- to 6-membered monocyclic heteroaryl or 5- to 6-membered monocyclic heterocyclic group;

$R^6$ is hydrogen or $C_{1-6}$ alkyl, wherein $C_{1-6}$ alkyl may be optionally substituted with 1 to 3 substituents selected from halogen, hydroxy and carboxyl;

$R^{9a}$ and $R^{9b}$ are each independently (i) halogen, cyano, hydroxy, $-(CH_2)_n NR^{10a}R^{10b}$, $-(CH_2)_n C(O)R^{11}$, $-(CH_2)_n S(O)_m R^{11}$, $-(CH_2)_n S(O)_m NR^{10a}R^{10b}$, $-(CH_2)_n N(R^{10a})S(O)_m R^{11}$, $-(CH_2)_n C(O)NR^{10a}R^{10b}$, $-(CH_2)_n OC(O)R^{11}$, $-(CH_2)_n C(O)(CH_2)_n OR^{11}$, $-(CH_2)_n N(R^{10a})C(O)R^{11}$;

(ii) $C_{1-6}$ alkyl, $C_{2-8}$ alkenyl, $C_{2-8}$ alkynyl or $C_{1-6}$ alkoxy, all of which may be optionally substituted with 1 to 3 substituents selected from halogen, hydroxy and cyano;

(iii) $C_{3-8}$ cycloalkyl, 6- to 14-membered aryl, 5- to 14-membered heteroaryl or 3- to 14-membered heterocyclic group, all of which may be optionally substituted with 1 to 3 substituents selected from halogen, hydroxy, cyano, trifluoromethyl, $C_{1-6}$ alkyl, $C_{2-8}$ alkenyl, $C_{2-8}$ alkynyl, $C_{1-6}$ alkoxy, $-(CH_2)_n NR^{10a}R^{10b}$, $-(CH_2)_n C(O)R^{11}$, $-(CH_2)_n C(O)NR^{10a}R^{10b}$, $-(CH_2)_n S(O)_m R^{11}$, $-(CH_2)_n S(O)_m NR^{10a}R^{10b}$, $-(CH_2)_n N(R^{10a})S(O)_m R^{11}$, $-(CH_2)_n OC(O)R^{11}$ and $-(CH_2)_n N(R^{10a})C(O)R^{11}$;

$R^{10a}$ and $R^{10b}$ are each independently hydrogen, or $C_{1-6}$ alkyl, $C_{3-8}$ cycloalkyl, 6- to 14-membered aryl, 5- to 14-membered heteroaryl or 3- to 14-membered heterocyclic group, all of which except hydrogen may be optionally substituted with 1 to 3 substituents selected from hydroxy, halogen, cyano, carboxyl, $-(CH_2)_n NR^{10a}R^{10b}$, sulfamoyl, carbamoyl and sulfamino;

$R^{11}$ is hydrogen, $C_{1-6}$ alkyl or $C_{1-6}$ alkoxy, wherein $C_{1-6}$ alkyl and $C_{1-6}$ alkoxy may be optionally substituted with 1 to 3 substituents selected from halogen, cyano, hydroxy, carboxyl, $-(CH_2)_n NR^{10a}R^{10b}$, sulfamoyl and carbamoyl;

m is 0, 1 or 2; and n is 0-4.

(2) The compound of above (1), or a pharmaceutically acceptable salt, ester, solvate or stereoisomer thereof, wherein $R^8$ is hydrogen, halogen, cyano, hydroxy, carboxyl, $-(CH_2)_n NR^{10a}R^{10b}$, $-(CH_2)_n S(O)_m NR^{10a}R^{10b}$, $-(CH_2)_n N(R^{10a})S(O)_m R^{11}$, $C_{1-6}$ alkyl or $C_{1-6}$ alkoxy, wherein $C_{1-6}$ alkyl and $C_{1-6}$ alkoxy may be optionally substituted with 1 to 3 substituents selected from halogen, hydroxy and carboxyl;

$R^1$ is $C_{3-8}$ cycloalkyl, 6- to 10-membered aryl, 5- to 10-membered heteroaryl or 5- to 10-membered heterocyclic group, all of which may be optionally substituted with 1 to 3 $R^{9a}$;

$R^2$ is $C_{3-8}$ cycloalkyl, 6- to 10-membered aryl, 5- to 10-membered heteroaryl or 5- to 10-membered heterocyclic group, all of which may be optionally substituted with 1 to 3 $R^{9b}$;

$R^3$, $R^4$, $R^5$ and $R^6$ are each independently hydrogen or $C_{1-6}$ alkyl, wherein $C_{1-6}$ alkyl may be optionally substituted with 1 to 3 substituents selected from halogen, hydroxy and carboxyl;

$R^{9a}$ and $R^{9b}$ are each independently (i) halogen, cyano, hydroxy, $-(CH_2)_n NR^{10a}R^{10b}$, $-(CH_2)_n C(O)R^{11}$, $-(CH_2)_n S(O)_m R^{11}$, $-(CH_2)_n S(O)_m NR^{10a}R^{10b}$, $-(CH_2)_n N(R^{10a})S(O)_m R^{11}$, $-(CH_2)_n C(O)NR^{10a}R^{10b}$, $-(CH_2)_n OC(O)R^{11}$, $-(CH_2)_n C(O)(CH_2)_n OR^{11}$, $-(CH_2)_n N(R^{10a})C(O)R^{11}$;

(ii) $C_{1-6}$ alkyl or $C_{1-6}$ alkoxy, all of which may be optionally substituted with 1 to 3 substituents selected from halogen, hydroxy and cyano;

(iii) $C_{3-8}$ cycloalkyl, 6- to 10-membered aryl, 5- to 10-membered heteroaryl or 5- to 10-membered heterocyclic group, all of which may be optionally substituted with 1 to 3 substituents selected from halogen, hydroxy, cyano, trifluoromethyl, $C_{1-6}$ alkyl, $C_{1-6}$ alkoxy, $-(CH_2)_n NR^{10a}R^{10b}$, $-(CH_2)_n C(O)R^{11}$, $-(CH_2)_n C(O)NR^{10a}R^{10b}$, $-(CH_2)_n S(O)_m R^{11}$, $-(CH_2)_n S(O)_m NR^{10a}R^{10b}$, $-(CH_2)_n N(R^{10a})S(O)_m R^{11}$, $-(CH_2)_n OC(O)R^{11}$ and $-(CH_2)_n N(R^{10a})C(O)R^{11}$;

$R^{10a}$ and $R^{10b}$ are each independently hydrogen or $C_{1-6}$ alkyl, wherein $C_{1-6}$ alkyl may be optionally substituted with 1 to 3 substituents selected from hydroxy, halogen, cyano, carboxyl, $-(CH_2)_n NR^{10a}R^{10b}$, sulfamoyl, carbamoyl and sulfamino; and $R^{11}$ is hydrogen or $C_{1-6}$ alkyl, wherein $C_{1-6}$ alkyl may be optionally substituted with 1 to 3 substituents selected from halogen, cyano, hydroxy, carboxyl, $-NR^{10a}R^{10b}$, sulfamoyl and carbamoyl.

(3) The compound of above (2), or a pharmaceutically acceptable salt, ester, solvate or stereoisomer thereof, wherein X is O;

A and B are each CH;

$R^1$ is 6- to 10-membered aryl, 5- to 6-membered monocyclic heteroaryl, 9- to 10-membered fused heteroaryl, 5- to 6-membered monocyclic heterocyclic group or 9- to 10-membered fused heterocyclic group, all of which may be optionally substituted with 1 to 3 $R^{9a}$;

$R^2$ is 6- to 10-membered aryl, 5- to 6-membered monocyclic heteroaryl, 9- to 10-membered fused heteroaryl, 5- to 6-membered monocyclic heterocyclic group or 9- to 10-membered fused heterocyclic group, all of which may be optionally substituted with 1 to 3 $R^{9b}$;

$R^3$, $R^4$ and $R^5$ are each hydrogen;

$R^6$ is hydrogen or $C_{1-6}$ alkyl;

$R^{9a}$ and $R^{9b}$ are each independently (i) halogen, cyano, hydroxy, $-(CH_2)_n NR^{10a}R^{10b}$, $-(CH_2)_n C(O)R^{11}$, $-(CH_2)_n S(O)_m R^{11}$, $-(CH_2)_n S(O)_m NR^{10a}R^{10b}$, $-(CH_2)_n N(R^{10a})S(O)_m R^{11}$, $-(CH_2)_n C(O)NR^{10a}R^{10b}$, $-(CH_2)_n OC(O)R^{11}$, $-(CH_2)_n C(O)(CH_2)_n OR^{11}$, $-(CH_2)_n N(R^{10a})C(O)R^{11}$;

(ii) $C_{1-6}$ alkyl or $C_{1-6}$ alkoxy, all of which may be optionally substituted with 1 to 3 substituents selected from halogen, hydroxy and cyano;

(iii) 5- to 10-membered heteroaryl or 5- to 10-membered heterocyclic group, all of which may be optionally substituted with 1 to 3 substituents selected from halogen, hydroxy, cyano, trifluoromethyl, $C_{1-6}$ alkyl, $C_{1-6}$ alkoxy, $-(CH_2)_n NR^{10a}R^{10b}$, $-(CH_2)_n C(O)R^{11}$, $-(CH_2)_n C(O)NR^{10a}R^{10b}$, $-(CH_2)_n S(O)_m R^{11}$, $-(CH_2)_n S(O)_m NR^{10a}R^{10b}$, $-(CH_2)_n N(R^{10a})S(O)_m R^{11}$, $-(CH_2)_n OC(O)R^{11}$ and $-(CH_2)_n N(R^{10a})C(O)R^{11}$;

$R^{10a}$ and $R^{10b}$ are each independently hydrogen or $C_{1-6}$ alkyl;

$R^{11}$ is hydrogen or $C_{1-6}$ alkyl, wherein $C_{1-6}$ alkyl may be optionally substituted with 1 to 3 substituents selected from halogen, cyano, hydroxyl and $-(CH_2)_n NR^{10a}R^{10b}$; and n is 0-3.

(4) The compound of above (3), or a pharmaceutically acceptable salt, ester, solvate or stereoisomer thereof, wherein $R^1$ is 6- to 10-membered aryl or 5- to 6-membered monocyclic heteroaryl, all of which may be optionally substituted with 1 to 3 $R^{9a}$;

R² is 6- to 10-membered aryl, 5- to 6-membered monocyclic heteroaryl or 9- to 10-membered fused heteroaryl, all of which may be optionally substituted with 1 to 3 $R^{9b}$; and $R^{9a}$ and $R^{9b}$ are each independently (i) halogen, cyano, hydroxy, $-(CH_2)_nNR^{10a}R^{10b}$, $-(CH_2)_nN(R^{10a})C(O)R^{11}$, $-(CH_2)_nC(O)R^{11}$, $-(CH_2)_nS(O)_mR^{11}$, $-(CH_2)_nC(O)NR^{10a}R^{10b}$, $-(CH_2)_nC(O)(CH_2)_nOR^{11}$;

(ii) $C_{1-6}$ alkyl or $C_{1-6}$ alkoxy, all of which may be optionally substituted with 1 to 3 substituents selected from halogen, hydroxy and cyano;

(iii) 5- to 6-membered monocyclic heteroaryl or 5- to 6-membered monocyclic heterocyclic group, all of which may be optionally substituted with 1 to 3 substituents selected from halogen, hydroxy, cyano, trifluoromethyl, $C_{1-6}$ alkyl, $C_{1-6}$ alkoxy, $-(CH_2)_nNR^{10a}R^{10b}$, $-(CH_2)_nC(O)R^{11}$, $-(CH_2)C(O)NR^{10a}R^{10b}$, $-(CH_2)_nOC(O)R^{11}$ and $-(CH_2)_nN(R^{10a})C(O)R^{11}$.

(5) The compound of above (4), or a pharmaceutically acceptable salt, ester, solvate or stereoisomer thereof, wherein $R^1$ is phenyl, pyridyl or pyrimidinyl, all of which may be optionally substituted with 1 to 3 $R^{9a}$;

$R^2$ is phenyl, pyridyl, pyrimidinyl, thienyl, pyrazolyl, indazolyl, indolyl, pyridopyrrolyl, pyrazolopyridyl or quinolyl, all of which may be optionally substituted with 1 to 3 $R^{9b}$;

$R^{9a}$ and $R^{9b}$ are each independently (i) cyano, hydroxy, $-NR^{10a}R^{10b}$, $-N(R^{10a})C(O)R^{11}$, $-C(O)R^{11}$, $-S(O)_mR^{11}$, $-C(O)NR^{10a}R^{10b}$, $-C(O)CH_2OR^{11}$;

(ii) $C_{1-6}$ alkyl or $C_{1-6}$ alkoxy, all of which may be optionally substituted with 1 to 3 substituents selected from halogen, hydroxy and cyano;

(iii) pyrrolyl, pyrazolyl, imidazolyl, piperidinyl, piperazinyl or morpholinyl, all of which may be optionally substituted with 1 to 3 substituents selected from halogen, hydroxy, cyano, trifluoromethyl, $C_{1-6}$ alkyl, $C_{1-6}$ alkoxy, $-NR^{10a}R^{10b}$, $-C(O)R^{11}$, $-C(O)NR^{10a}R^{10b}$, $-OC(O)R^{11}$ and $-N(R^{10a})C(O)R^{11}$;

$R^{11}$ is hydrogen or $C_{1-6}$ alkyl, wherein $C_{1-6}$ alkyl may be optionally substituted with 1 to 3 substituents selected from halogen, cyano and hydroxy; and n is 0.

(6) The compound of above (5), or a pharmaceutically acceptable salt, ester, solvate or stereoisomer thereof, wherein $R^1$ is phenyl optionally substituted with 1 to 3 $R^{9a}$.

(7) The compound of above (1), or a pharmaceutically acceptable salt, ester, solvate or stereoisomer thereof, wherein general formula (I) is represented by general formula (II) as shown below:

(II)

wherein $R^2$, $R^3$, $R^4$, $R^5$, $R^6$, X, A and B are as defined in above (1), and $R^{9a}$ is $C_{1-6}$ alkyl optionally substituted with 1 to 3 halogen atoms.

More preferred compounds of the present invention are as shown in the following Table 1.

| No. | Structural Formula |
|---|---|
| 1 | |
| 2 | |
| 3 | |
| 4 | |
| 5 | |

| No. | Structural Formula |
|---|---|
| 6 | 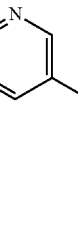 |
| 7 | |
| 8 | |
| 9 | |
| 10 | |
| No. | Structural Formula |
|---|---|
| 11 | 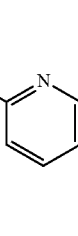 |
| 12 | |
| 13 | |
| 14 | |
| 15 | |

| No. | Structural Formula |
|---|---|
| 16 | 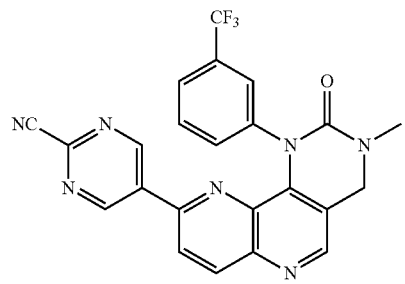 [SMILES: CN1Cc2cnc3ccc(-c4cnc(C#N)nc4)nc3c2N(c2cccc(C(F)(F)F)c2)C1=O] |
| 17 | 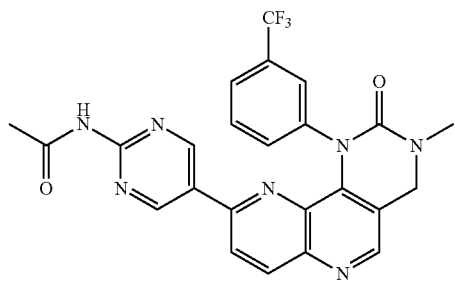 [SMILES: CC(=O)Nc1ncc(-c2ccc3ncc4c(c3n2)N(c2cccc(C(F)(F)F)c2)C(=O)N(C)C4)cn1] |
| 18 | 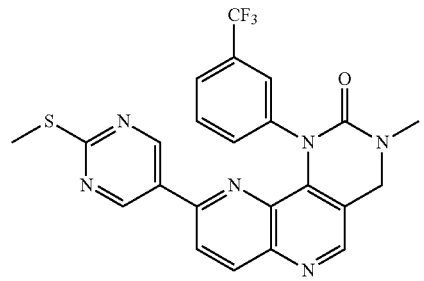 |
| 19 | 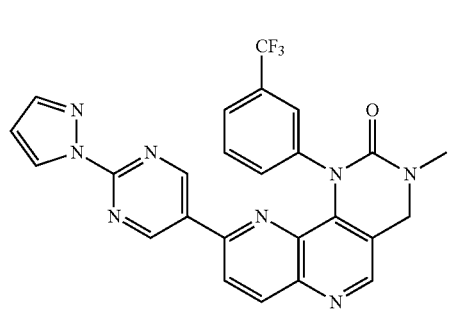 [SMILES: CN1Cc2cnc3ccc(-c4cnc(-n5cccn5)nc4)nc3c2N(c2cccc(C(F)(F)F)c2)C1=O] |
| 20 | 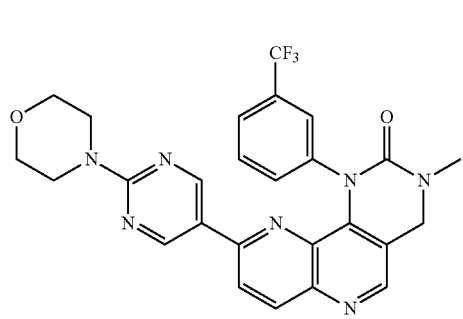 |
| No. | Structural Formula |
|---|---|
| 21 | 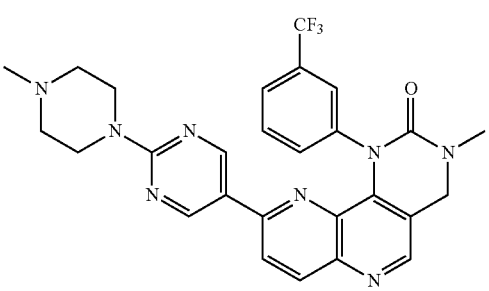 |
| 22 | 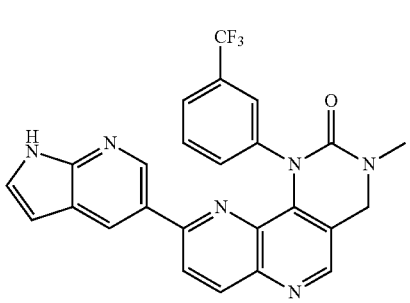 [SMILES: CN1Cc2cnc3ccc(-c4cnc5[nH]ccc5c4)nc3c2N(c2cccc(C(F)(F)F)c2)C1=O] |
| 23 | 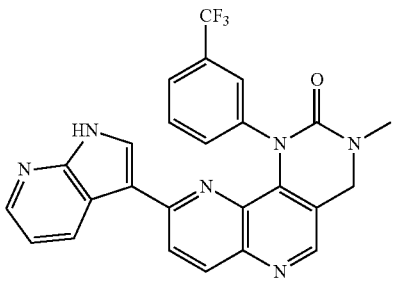 [SMILES: CN1Cc2cnc3ccc(-c4c[nH]c5ncccc45)nc3c2N(c2cccc(C(F)(F)F)c2)C1=O] |
| 24 | 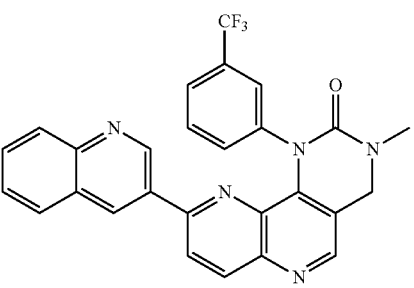 [SMILES: CN1Cc2cnc3ccc(-c4cnc5ccccc5c4)nc3c2N(c2cccc(C(F)(F)F)c2)C1=O] |
| 25 | 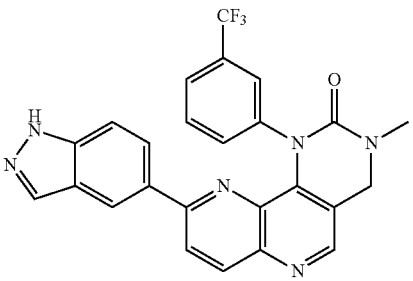 [SMILES: CN1Cc2cnc3ccc(-c4ccc5[nH]ncc5c4)nc3c2N(c2cccc(C(F)(F)F)c2)C1=O] |

| No. | Structural Formula |
|---|---|
| 26 | 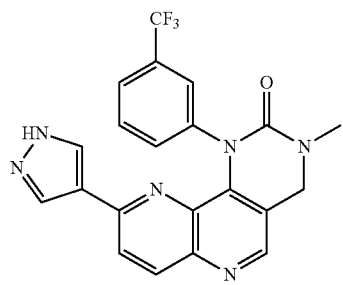 [SMILES: CN1Cc2cnc3ccc(-c4cn[nH]c4)nc3c2N(c2cccc(C(F)(F)F)c2)C1=O] |
| 27 | 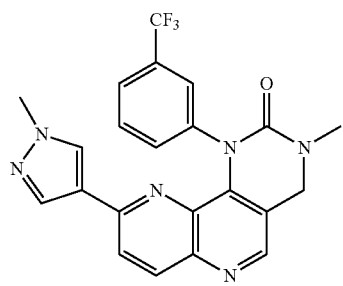 [SMILES: CN1Cc2cnc3ccc(-c4cnn(C)c4)nc3c2N(c2cccc(C(F)(F)F)c2)C1=O] |
| 28 | 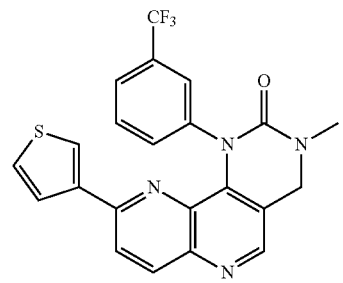 [SMILES: CN1Cc2cnc3ccc(-c4ccsc4)nc3c2N(c2cccc(C(F)(F)F)c2)C1=O] |
| 29 | 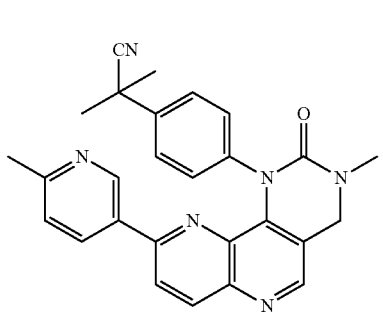 |
| 30 | 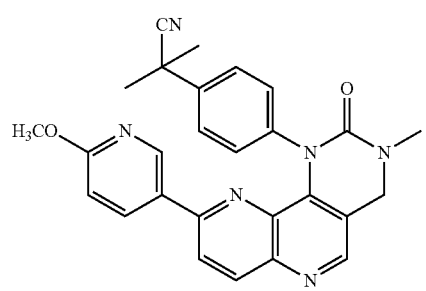 [SMILES: COc1ccc(-c2ccc3ncc4c(c3n2)N(c2ccc(C(C)(C)C#N)cc2)C(=O)N(C)C4)cn1] |
| No. | Structural Formula |
|---|---|
| 31 | 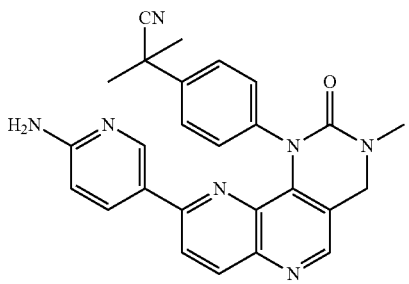 [SMILES: CN1Cc2cnc3ccc(-c4ccc(N)nc4)nc3c2N(c2ccc(C(C)(C)C#N)cc2)C1=O] |
| 32 | 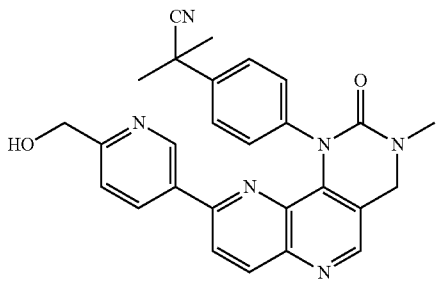 [SMILES: CN1Cc2cnc3ccc(-c4ccc(CO)nc4)nc3c2N(c2ccc(C(C)(C)C#N)cc2)C1=O] |
| 33 | 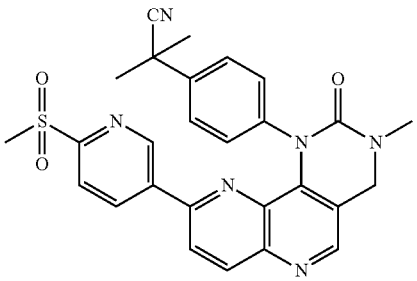 |
| 34 | 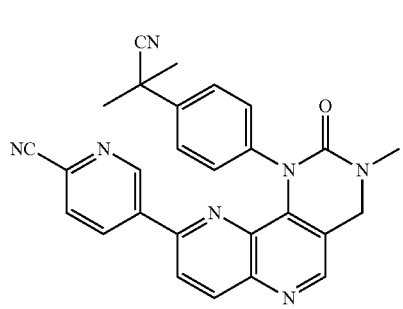 |
| 35 | 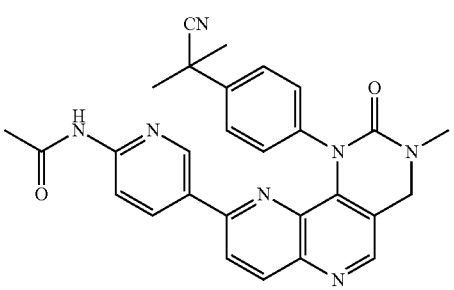 [SMILES: CC(=O)Nc1ccc(-c2ccc3ncc4c(c3n2)N(c2ccc(C(C)(C)C#N)cc2)C(=O)N(C)C4)cn1] |

-continued
| No. | Structural Formula |
|---|---|
| 36 | 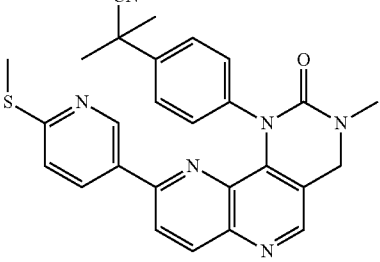 |
| 37 | 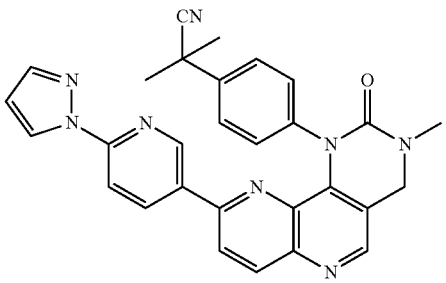 [SMILES: CN1Cc2cnc3ccc(-c4ccc(-n5cccn5)nc4)nc3c2N(c2ccc(C(C)(C)C#N)cc2)C1=O] |
| 38 | 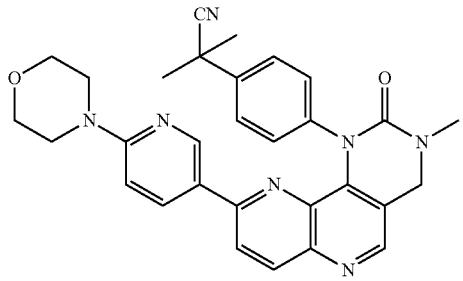 [SMILES: CN1Cc2cnc3ccc(-c4ccc(N5CCOCC5)nc4)nc3c2N(c2ccc(C(C)(C)C#N)cc2)C1=O] |
| 39 | 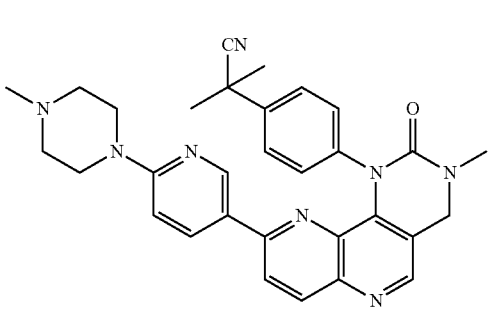 |
| 40 | 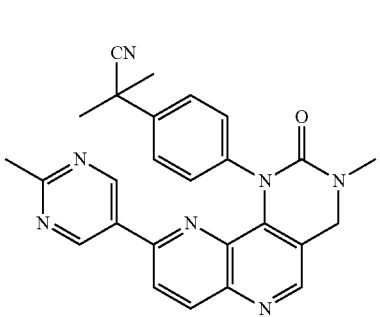 |
-continued
| No. | Structural Formula |
|---|---|
| 41 | 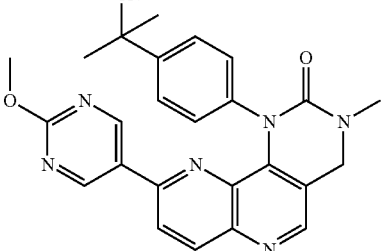 |
| 42 | 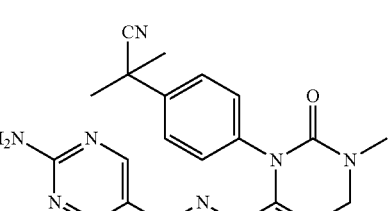 |
| 43 | 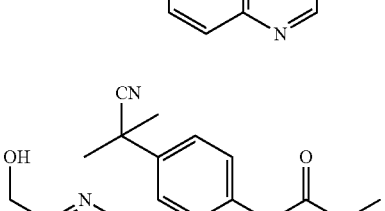 |
| 44 | 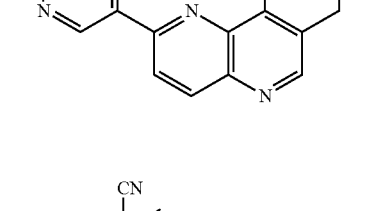 |
| 45 | 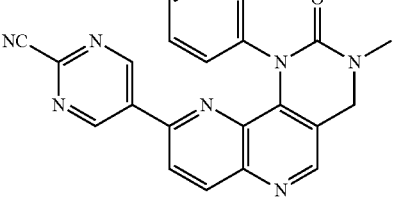 |

| No. | Structural Formula |
|---|---|
| 46 | 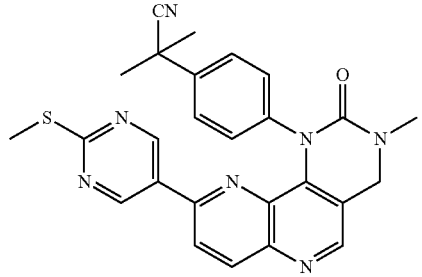 |
| 47 | 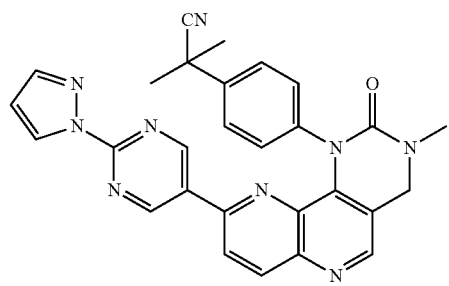 [SMILES: CN1Cc2cnc3ccc(-c4cnc(-n5cccn5)nc4)nc3c2N(c2ccc(C(C)(C)C#N)cc2)C1=O] |
| 48 | 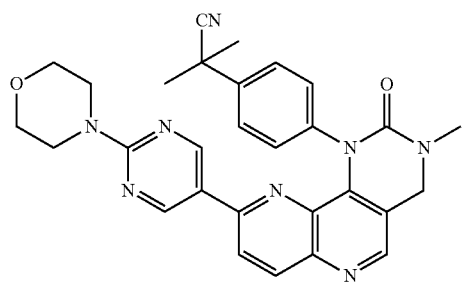 [SMILES: CN1Cc2cnc3ccc(-c4cnc(N5CCOCC5)nc4)nc3c2N(c2ccc(C(C)(C)C#N)cc2)C1=O] |
| 49 | 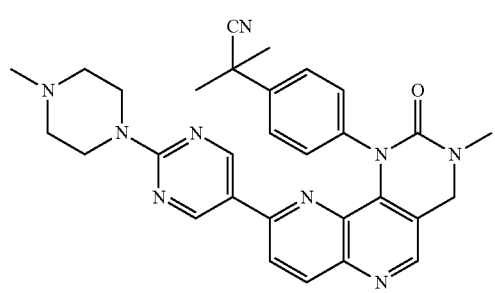 |
| 50 | 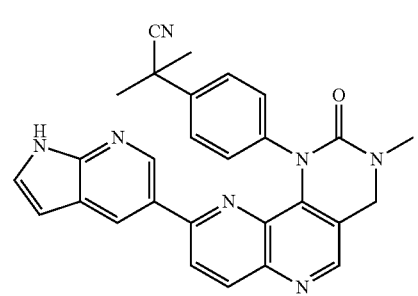 [SMILES: CN1Cc2cnc3ccc(-c4cnc5[nH]ccc5c4)nc3c2N(c2ccc(C(C)(C)C#N)cc2)C1=O] |
| No. | Structural Formula |
|---|---|
| 51 | 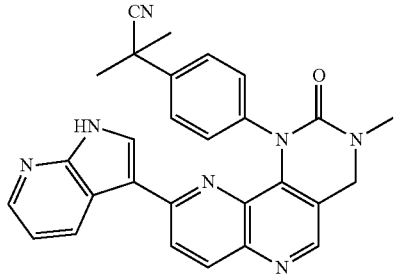 [SMILES: CN1Cc2cnc3ccc(-c4c[nH]c5ncccc45)nc3c2N(c2ccc(C(C)(C)C#N)cc2)C1=O] |
| 52 | 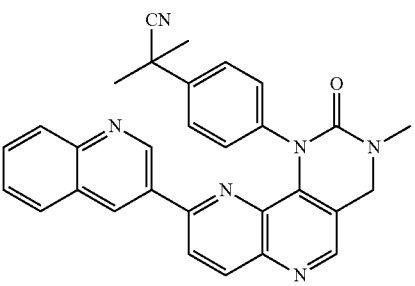 [SMILES: CN1Cc2cnc3ccc(-c4cnc5ccccc5c4)nc3c2N(c2ccc(C(C)(C)C#N)cc2)C1=O] |
| 53 | 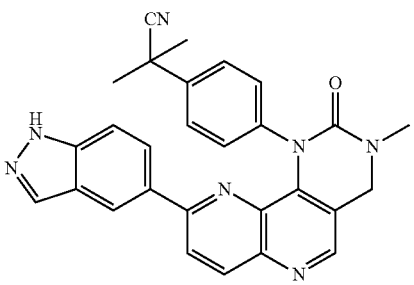 [SMILES: CN1Cc2cnc3ccc(-c4ccc5[nH]ncc5c4)nc3c2N(c2ccc(C(C)(C)C#N)cc2)C1=O] |
| 54 | 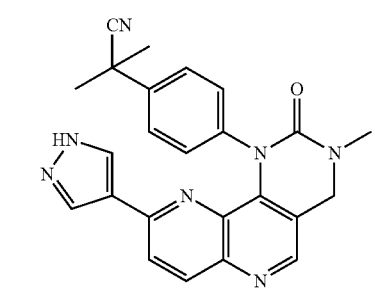 [SMILES: CN1Cc2cnc3ccc(-c4cn[nH]c4)nc3c2N(c2ccc(C(C)(C)C#N)cc2)C1=O] |
| 55 | 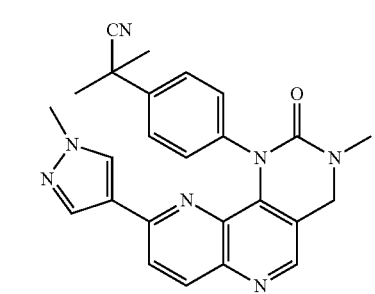 [SMILES: CN1Cc2cnc3ccc(-c4cnn(C)c4)nc3c2N(c2ccc(C(C)(C)C#N)cc2)C1=O] |

-continued

| No. | Structural Formula |
|---|---|
| 56 | |
| 57 | |
| 58 | |
| 59 | |
| 60 | |

-continued

| No. | Structural Formula |
|---|---|
| 61 | |
| 62 | |
| 63 | |
| 64 | |
| 65 | |

| No. | Structural Formula |
|---|---|
| 66 | |
| 67 | |
| 68 | |
| 69 | |
| 70 | |

| No. | Structural Formula |
|---|---|
| 71 | |
| 72 | |
| 73 | |
| 74 | |
| 75 | |

| No. | Structural Formula |
|---|---|
| 76 | 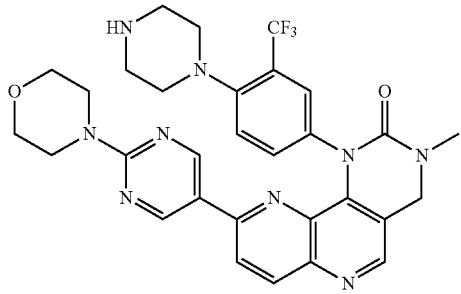 [SMILES: CN1Cc2cnc3ccc(-c4cnc(N5CCOCC5)nc4)nc3c2N(c2ccc(N3CCNCC3)c(C(F)(F)F)c2)C1=O] |
| 77 | 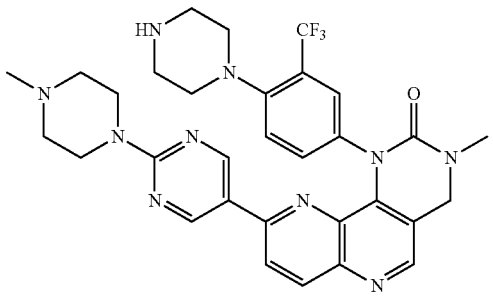 |
| 78 | 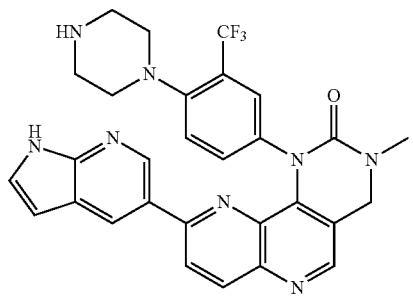 [SMILES: CN1Cc2cnc3ccc(-c4cnc5[nH]ccc5c4)nc3c2N(c2ccc(N3CCNCC3)c(C(F)(F)F)c2)C1=O] |
| 79 | 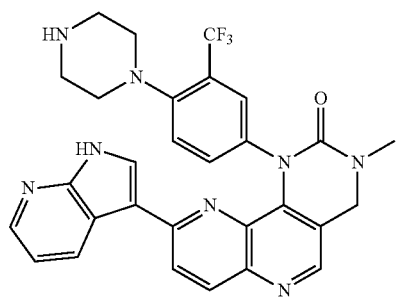 [SMILES: CN1Cc2cnc3ccc(-c4c[nH]c5ncccc45)nc3c2N(c2ccc(N3CCNCC3)c(C(F)(F)F)c2)C1=O] |
| 80 | 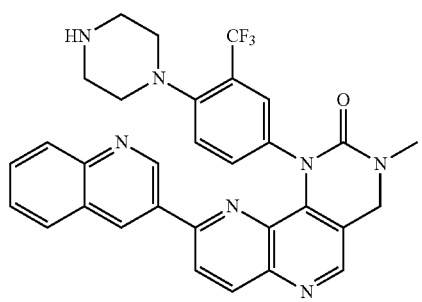 [SMILES: CN1Cc2cnc3ccc(-c4cnc5ccccc5c4)nc3c2N(c2ccc(N3CCNCC3)c(C(F)(F)F)c2)C1=O] |
| 81 | 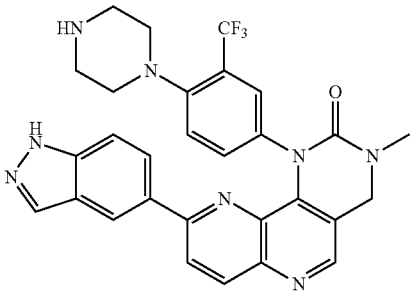 [SMILES: CN1Cc2cnc3ccc(-c4ccc5[nH]ncc5c4)nc3c2N(c2ccc(N3CCNCC3)c(C(F)(F)F)c2)C1=O] |
| 82 | 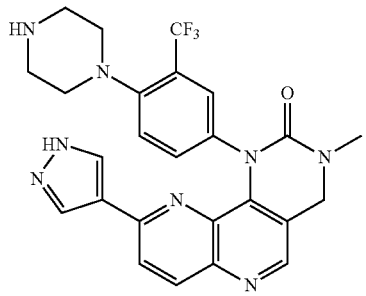 [SMILES: CN1Cc2cnc3ccc(-c4cn[nH]c4)nc3c2N(c2ccc(N3CCNCC3)c(C(F)(F)F)c2)C1=O] |
| 83 | 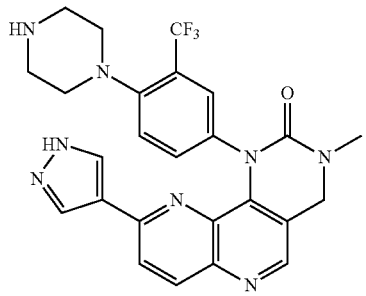 [SMILES: CN1Cc2cnc3ccc(-c4cn[nH]c4)nc3c2N(c2ccc(N3CCNCC3)c(C(F)(F)F)c2)C1=O] |
| 84 | 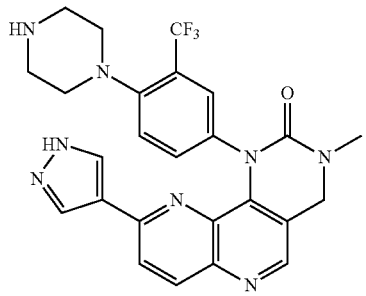 [SMILES: CN1Cc2cnc3ccc(-c4cn[nH]c4)nc3c2N(c2ccc(N3CCNCC3)c(C(F)(F)F)c2)C1=O] |
| 85 | 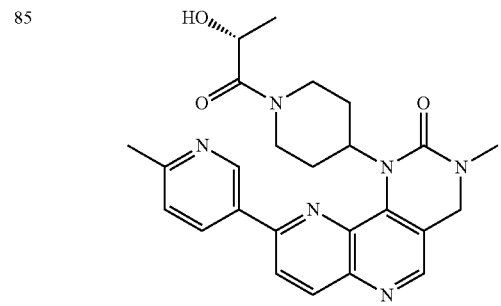 |

| No. | Structural Formula |
|---|---|
| 86 | (structure) |
| 87 | (structure) |
| 88 | (structure) |
| 89 | (structure) |
| 90 | (structure) |
| 91 | (structure) |
| 92 | (structure) |
| 93 | (structure) |
| 94 | (structure) |
| 95 | (structure) |

| No. | Structural Formula |
|---|---|
| 96 | 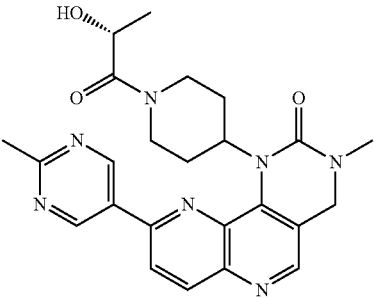 |
| 97 | 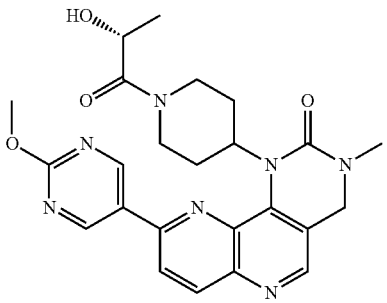 [SMILES: COc1ncc(-c2ccc3ncc4c(c3n2)N(C2CCN(C(=O)[C@@H](C)O)CC2)C(=O)N(C)C4)cn1] |
| 98 | 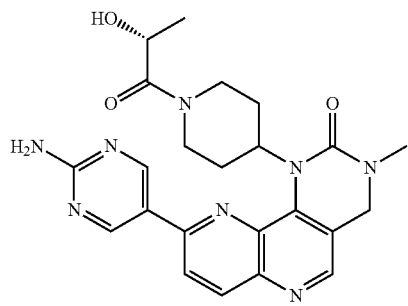 [SMILES: C[C@@H](O)C(=O)N1CCC(N2C(=O)N(C)Cc3cnc4ccc(-c5cnc(N)nc5)nc4c32)CC1] |
| 99 | 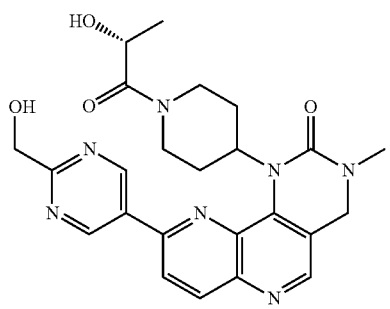 [SMILES: C[C@@H](O)C(=O)N1CCC(N2C(=O)N(C)Cc3cnc4ccc(-c5cnc(CO)nc5)nc4c32)CC1] |
| 100 | 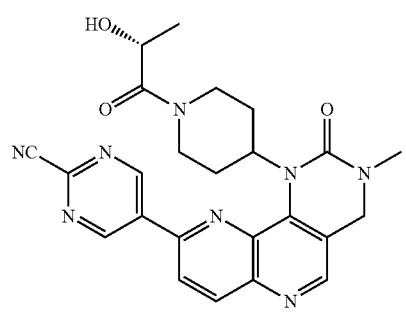 [SMILES: C[C@@H](O)C(=O)N1CCC(N2C(=O)N(C)Cc3cnc4ccc(-c5cnc(C#N)nc5)nc4c32)CC1] |
| No. | Structural Formula |
|---|---|
| 101 | 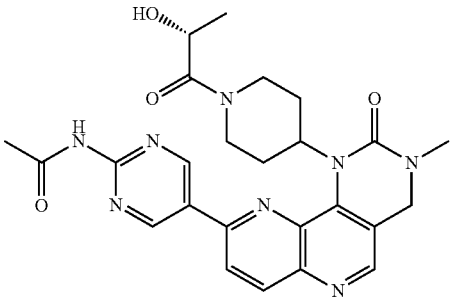 [SMILES: CC(=O)Nc1ncc(-c2ccc3ncc4c(c3n2)N(C2CCN(C(=O)[C@@H](C)O)CC2)C(=O)N(C)C4)cn1] |
| 102 | 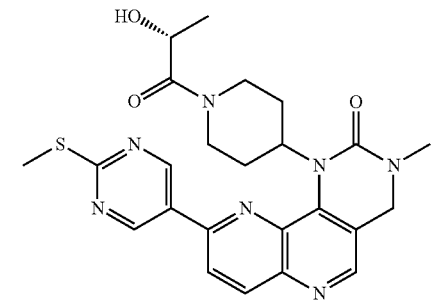 |
| 103 | 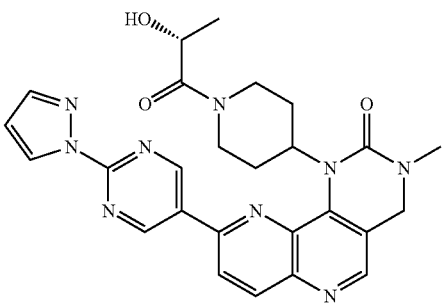 [SMILES: C[C@@H](O)C(=O)N1CCC(N2C(=O)N(C)Cc3cnc4ccc(-c5cnc(-n6cccn6)nc5)nc4c32)CC1] |
| 104 | 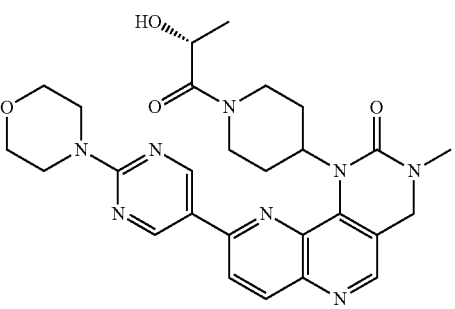 [SMILES: C[C@@H](O)C(=O)N1CCC(N2C(=O)N(C)Cc3cnc4ccc(-c5cnc(N6CCOCC6)nc5)nc4c32)CC1] |
| 105 | 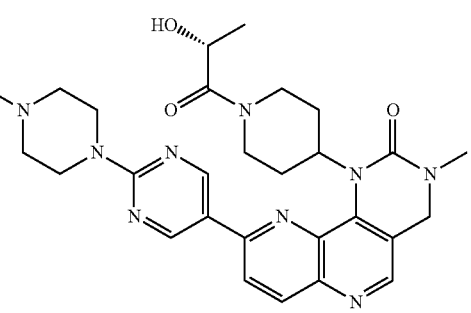 |

| No. | Structural Formula |
|---|---|
| 106 | |
| 107 | |
| 108 | |
| 109 | |
| 110 | |
| 111 | |
| 112 | |
| 113 | |
| 114 | |
| 115 | |
| 116 | |

| No. | Structural Formula |
|---|---|
| 117 | 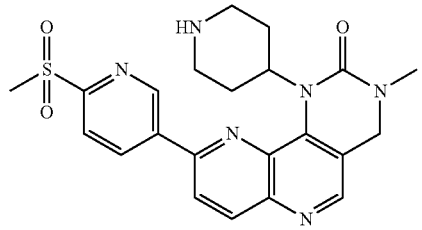 |
| 118 | 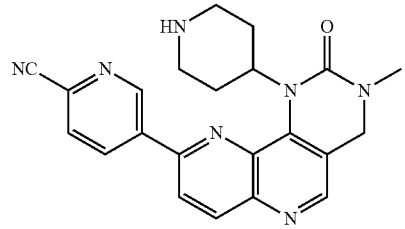 |
| 119 | 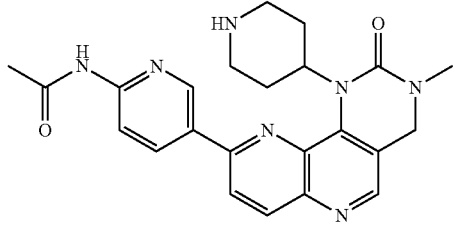 |
| 120 | 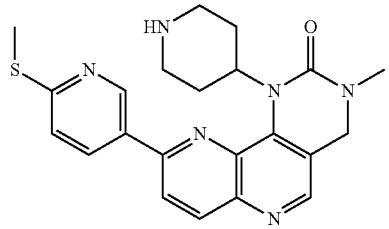 [SMILES: CSc1ccc(-c2ccc3ncc4c(c3n2)N(C2CCNCC2)C(=O)N(C)C4)cn1] |
| 121 | 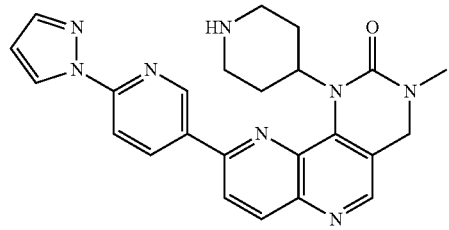 [SMILES: CN1Cc2cnc3ccc(-c4ccc(-n5cccn5)nc4)nc3c2N(C2CCNCC2)C1=O] |
| 122 | 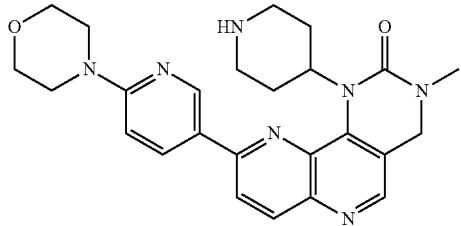 [SMILES: CN1Cc2cnc3ccc(-c4ccc(N5CCOCC5)nc4)nc3c2N(C2CCNCC2)C1=O] |
| No. | Structural Formula |
|---|---|
| 123 | 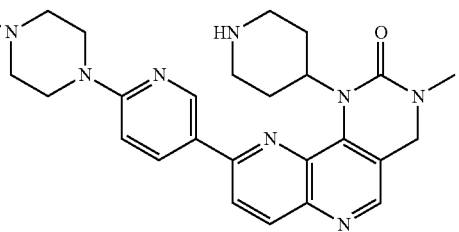 |
| 124 | 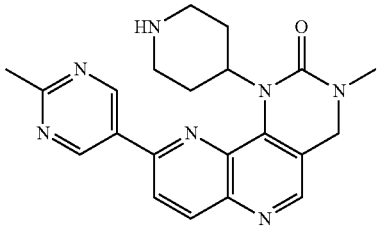 |
| 125 | 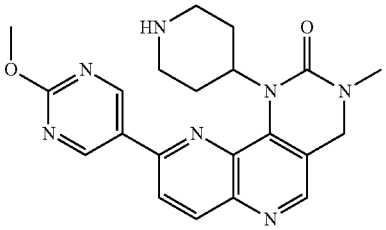 [SMILES: COc1ncc(-c2ccc3ncc4c(c3n2)N(C2CCNCC2)C(=O)N(C)C4)cn1] |
| 126 | 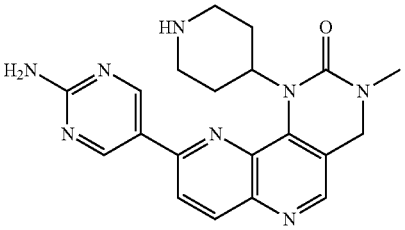 [SMILES: CN1Cc2cnc3ccc(-c4cnc(N)nc4)nc3c2N(C2CCNCC2)C1=O] |
| 127 | 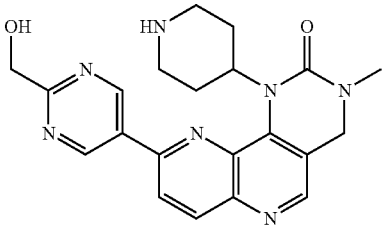 [SMILES: CN1Cc2cnc3ccc(-c4cnc(CO)nc4)nc3c2N(C2CCNCC2)C1=O] |
| 128 | 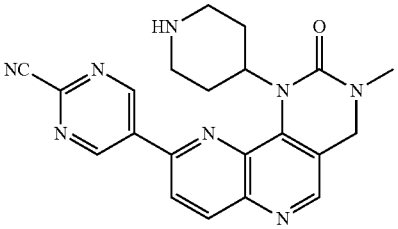 [SMILES: CN1Cc2cnc3ccc(-c4cnc(C#N)nc4)nc3c2N(C2CCNCC2)C1=O] |

| No. | Structural Formula |
|---|---|
| 129 | 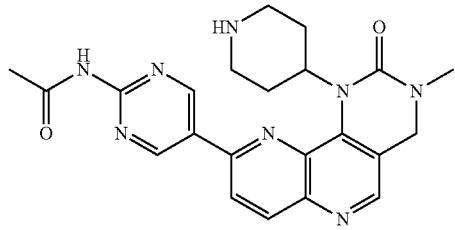 [SMILES: CC(=O)Nc1ncc(-c2ccc3ncc4c(c3n2)N(C2CCNCC2)C(=O)N(C)C4)cn1] |
| 130 | 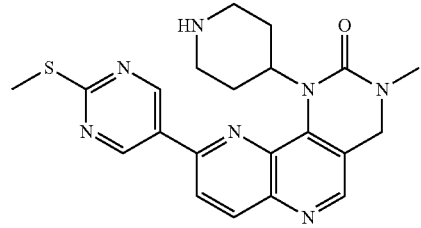 |
| 131 | 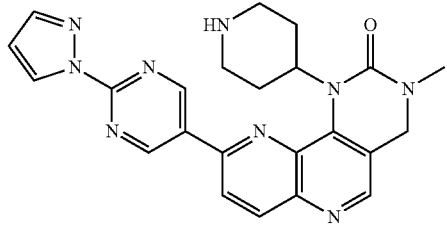 [SMILES: CN1Cc2cnc3ccc(-c4cnc(-n5cccn5)nc4)nc3c2N(C2CCNCC2)C1=O] |
| 132 | 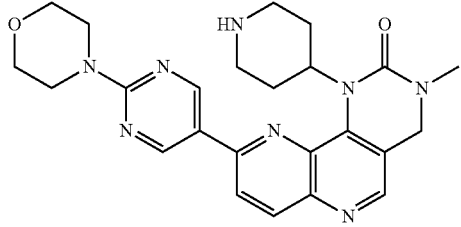 [SMILES: CN1Cc2cnc3ccc(-c4cnc(N5CCOCC5)nc4)nc3c2N(C2CCNCC2)C1=O] |
| 133 | 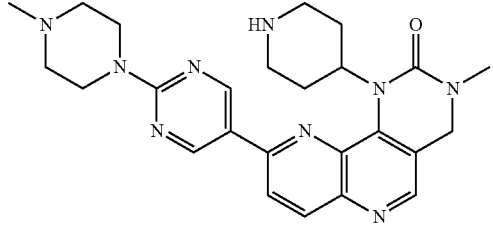 |
| 134 | 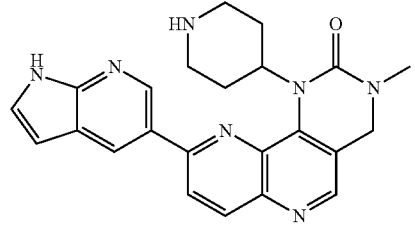 [SMILES: CN1Cc2cnc3ccc(-c4cnc5[nH]ccc5c4)nc3c2N(C2CCNCC2)C1=O] |
| No. | Structural Formula |
|---|---|
| 135 | 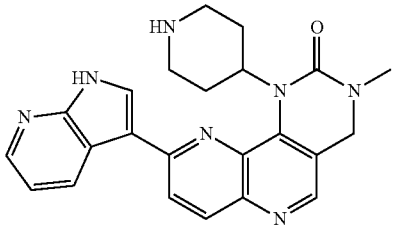 [SMILES: CN1Cc2cnc3ccc(-c4c[nH]c5ncccc45)nc3c2N(C2CCNCC2)C1=O] |
| 136 | 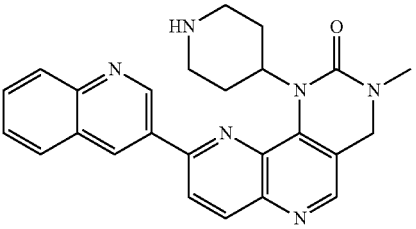 [SMILES: CN1Cc2cnc3ccc(-c4cnc5ccccc5c4)nc3c2N(C2CCNCC2)C1=O] |
| 137 | 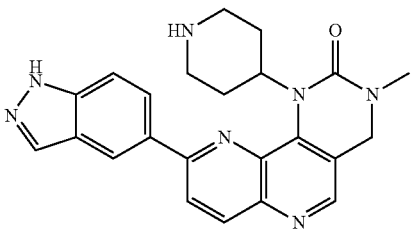 [SMILES: CN1Cc2cnc3ccc(-c4ccc5[nH]ncc5c4)nc3c2N(C2CCNCC2)C1=O] |
| 138 | 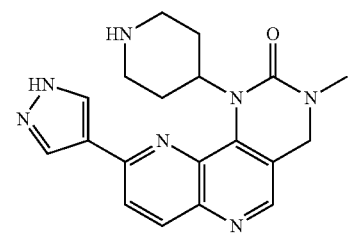 [SMILES: CN1Cc2cnc3ccc(-c4cn[nH]c4)nc3c2N(C2CCNCC2)C1=O] |
| 139 | 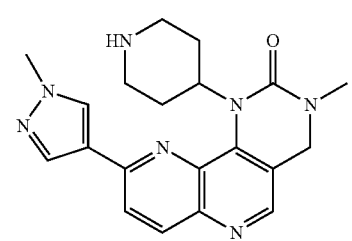 [SMILES: CN1Cc2cnc3ccc(-c4cnn(C)c4)nc3c2N(C2CCNCC2)C1=O] |
| 140 | 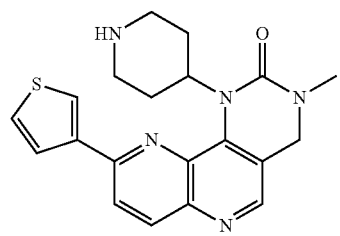 [SMILES: CN1Cc2cnc3ccc(-c4ccsc4)nc3c2N(C2CCNCC2)C1=O] |

| No. | Structural Formula |
|---|---|
| 141 | 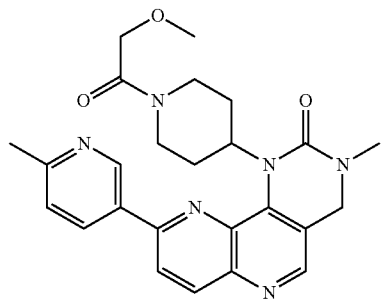 |
| 142 | 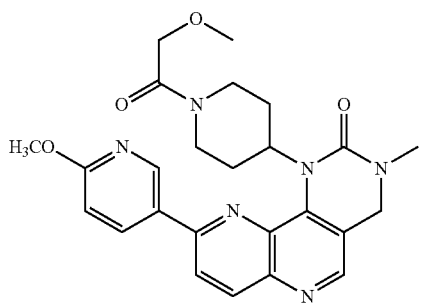 [SMILES: COCC(=O)N1CCC(N2C(=O)N(C)Cc3cnc4ccc(-c5ccc(OC)nc5)nc4c32)CC1] |
| 143 | 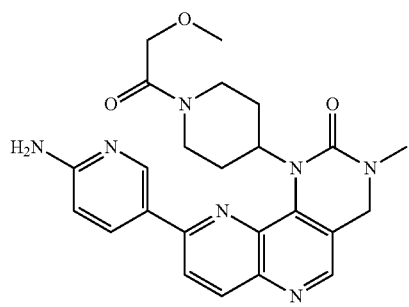 [SMILES: COCC(=O)N1CCC(N2C(=O)N(C)Cc3cnc4ccc(-c5ccc(N)nc5)nc4c32)CC1] |
| 144 | 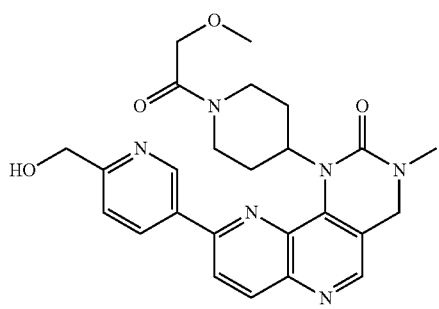 [SMILES: COCC(=O)N1CCC(N2C(=O)N(C)Cc3cnc4ccc(-c5ccc(CO)nc5)nc4c32)CC1] |
| 145 | 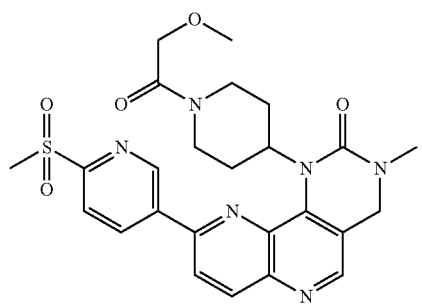 |
| No. | Structural Formula |
|---|---|
| 146 | 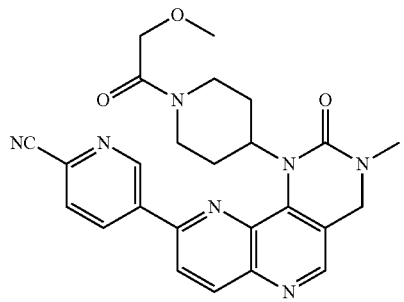 |
| 147 | 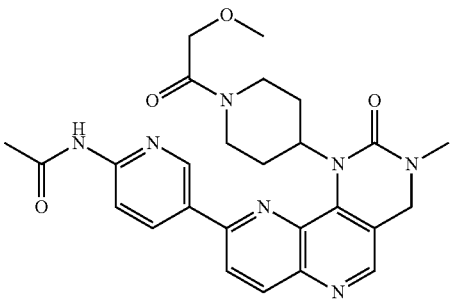 |
| 148 | 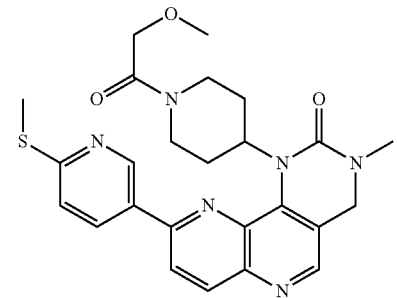 [SMILES: COCC(=O)N1CCC(N2C(=O)N(C)Cc3cnc4ccc(-c5ccc(SC)nc5)nc4c32)CC1] |
| 149 | 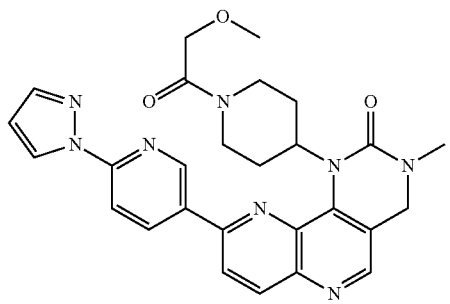 |
| 150 | 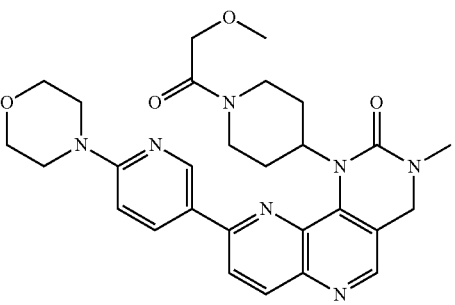 |

| No. | Structural Formula |
|---|---|
| 151 | 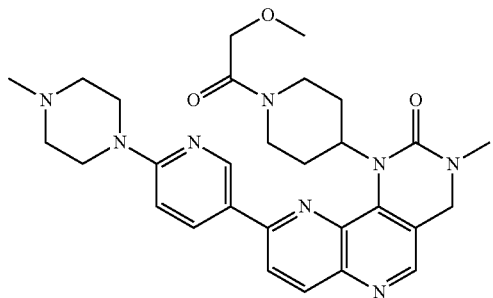 |
| 152 | 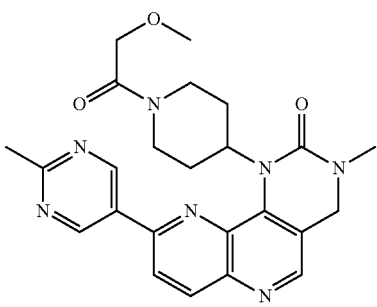 |
| 153 | 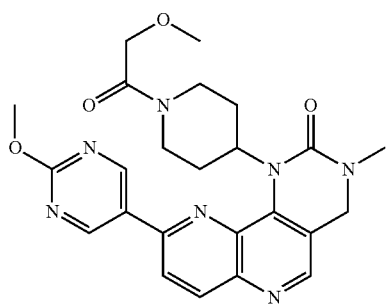 [SMILES: COCC(=O)N1CCC(N2C(=O)N(C)Cc3cnc4ccc(-c5cnc(OC)nc5)nc4c32)CC1] |
| 154 | 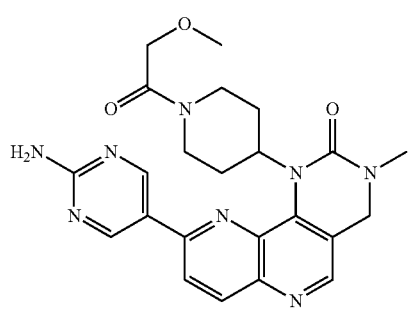 [SMILES: COCC(=O)N1CCC(N2C(=O)N(C)Cc3cnc4ccc(-c5cnc(N)nc5)nc4c32)CC1] |
| 155 | 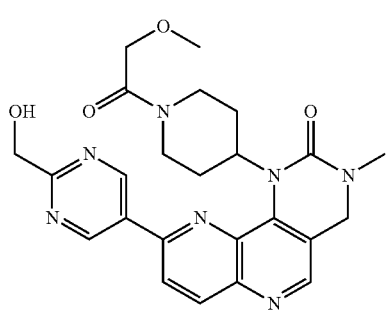 [SMILES: COCC(=O)N1CCC(N2C(=O)N(C)Cc3cnc4ccc(-c5cnc(CO)nc5)nc4c32)CC1] |
| No. | Structural Formula |
|---|---|
| 156 | 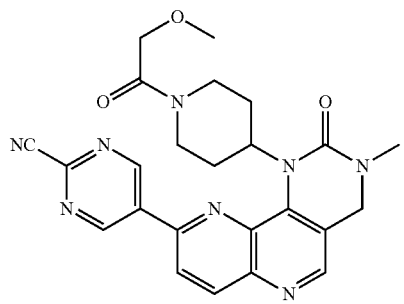 [SMILES: COCC(=O)N1CCC(N2C(=O)N(C)Cc3cnc4ccc(-c5cnc(C#N)nc5)nc4c32)CC1] |
| 157 | 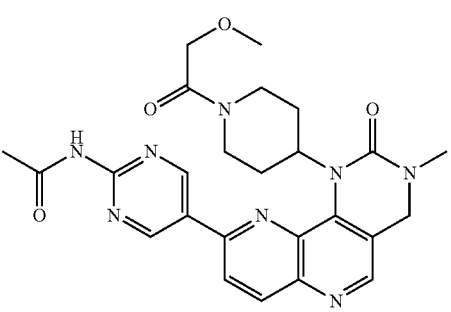 [SMILES: COCC(=O)N1CCC(N2C(=O)N(C)Cc3cnc4ccc(-c5cnc(NC(C)=O)nc5)nc4c32)CC1] |
| 158 | 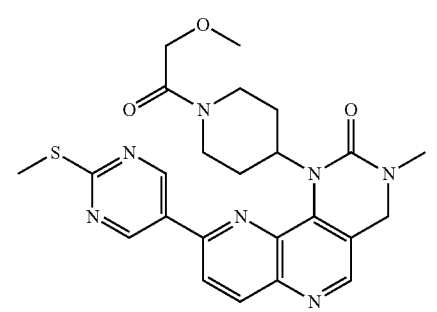 |
| 159 | 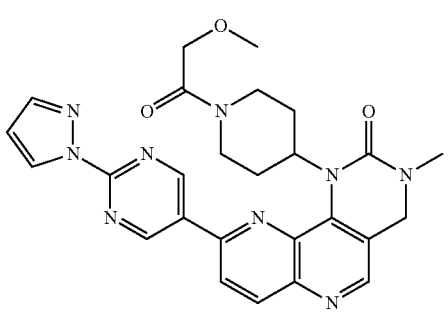 [SMILES: COCC(=O)N1CCC(N2C(=O)N(C)Cc3cnc4ccc(-c5cnc(-n6cccn6)nc5)nc4c32)CC1] |
| 160 | 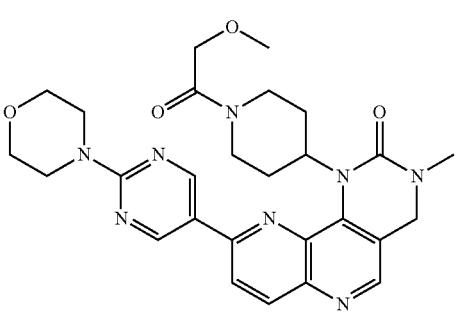 [SMILES: COCC(=O)N1CCC(N2C(=O)N(C)Cc3cnc4ccc(-c5cnc(N6CCOCC6)nc5)nc4c32)CC1] |

-continued

| No. | Structural Formula |
|---|---|
| 161 | |
| 162 | |
| 163 | |
| 164 | |
| 165 | |
| 166 | |
| 167 | |
| 168 | |
| 169 | |
| 170 | |

| No. | Structural Formula |
|---|---|
| 171 | 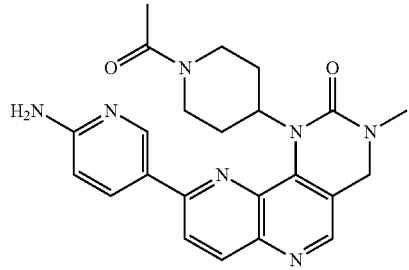 [SMILES: CC(=O)N1CCC(N2C(=O)N(C)Cc3cnc4ccc(-c5ccc(N)nc5)nc4c32)CC1] |
| 172 | 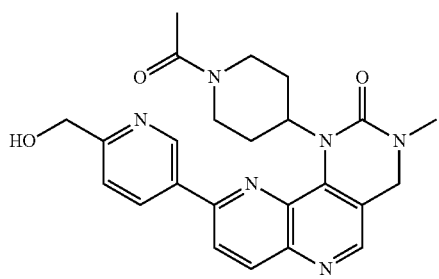 [SMILES: CC(=O)N1CCC(N2C(=O)N(C)Cc3cnc4ccc(-c5ccc(CO)nc5)nc4c32)CC1] |
| 173 | 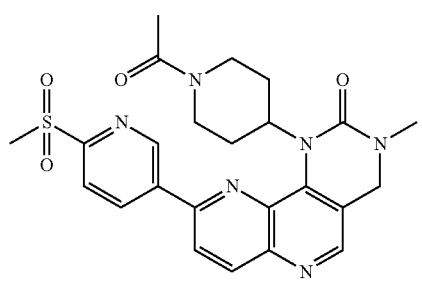 |
| 174 | 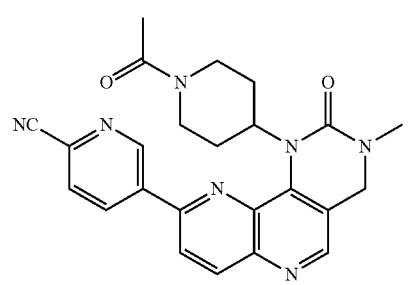 [SMILES: CC(=O)N1CCC(N2C(=O)N(C)Cc3cnc4ccc(-c5ccc(C#N)nc5)nc4c32)CC1] |
| 175 | 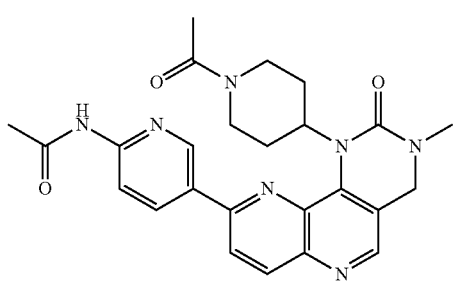 [SMILES: CC(=O)Nc1ccc(-c2ccc3ncc4c(c3n2)N(C2CCN(C(C)=O)CC2)C(=O)N(C)C4)cn1] |
| 176 | 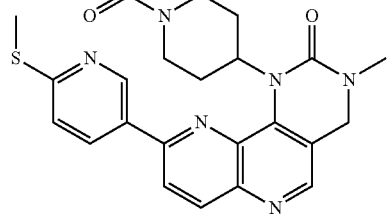 |
| 177 | 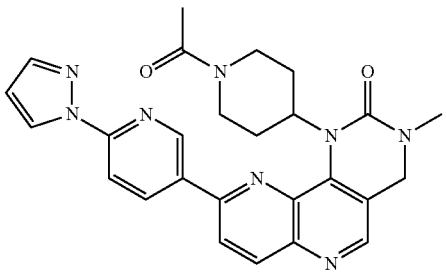 [SMILES: CC(=O)N1CCC(N2C(=O)N(C)Cc3cnc4ccc(-c5ccc(-n6cccn6)nc5)nc4c32)CC1] |
| 178 | 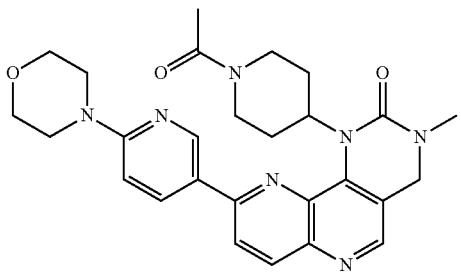 [SMILES: CC(=O)N1CCC(N2C(=O)N(C)Cc3cnc4ccc(-c5ccc(N6CCOCC6)nc5)nc4c32)CC1] |
| 179 | 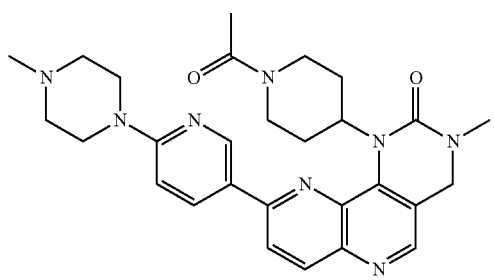 |
| 180 | 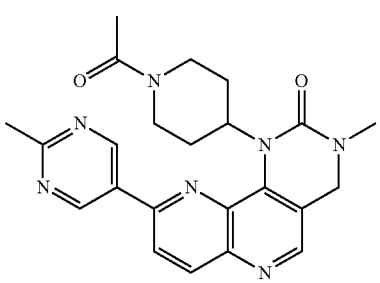 |

| No. | Structural Formula |
|---|---|
| 181 | 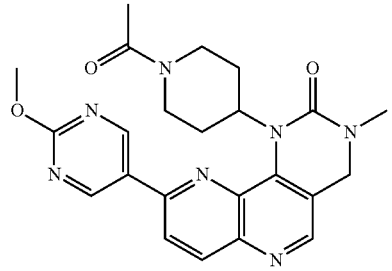 [SMILES: COc1ncc(-c2ccc3ncc4c(c3n2)N(C2CCN(C(C)=O)CC2)C(=O)N(C)C4)cn1] |
| 182 | 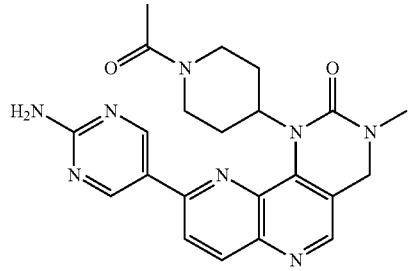 |
| 183 | 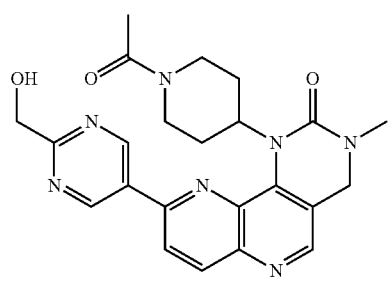 [SMILES: CC(=O)N1CCC(N2C(=O)N(C)Cc3cnc4ccc(-c5cnc(CO)nc5)nc4c32)CC1] |
| 184 | 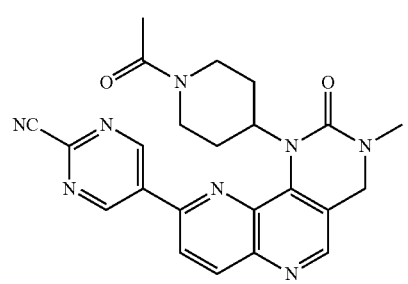 [SMILES: CC(=O)N1CCC(N2C(=O)N(C)Cc3cnc4ccc(-c5cnc(C#N)nc5)nc4c32)CC1] |
| 185 | 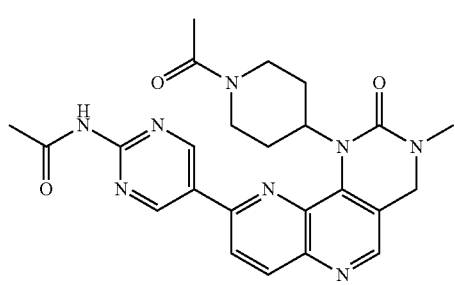 [SMILES: CC(=O)Nc1ncc(-c2ccc3ncc4c(c3n2)N(C2CCN(C(C)=O)CC2)C(=O)N(C)C4)cn1] |
| No. | Structural Formula |
|---|---|
| 186 | 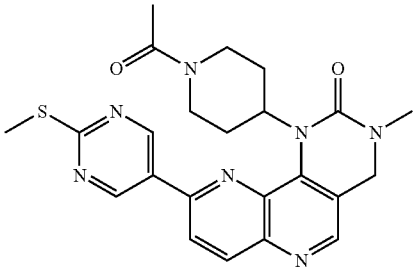 |
| 187 | 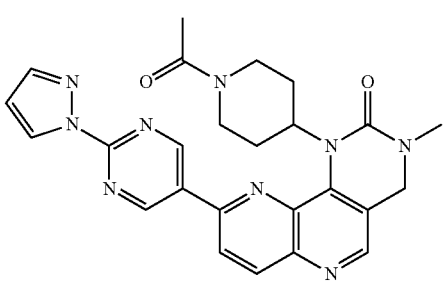 [SMILES: CC(=O)N1CCC(N2C(=O)N(C)Cc3cnc4ccc(-c5cnc(-n6cccn6)nc5)nc4c32)CC1] |
| 188 | 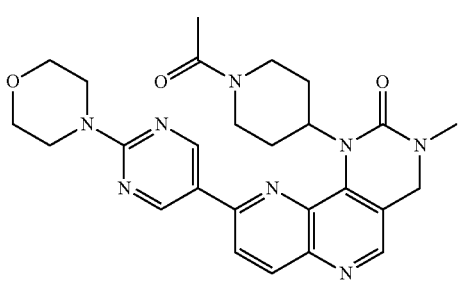 [SMILES: CC(=O)N1CCC(N2C(=O)N(C)Cc3cnc4ccc(-c5cnc(N6CCOCC6)nc5)nc4c32)CC1] |
| 189 | 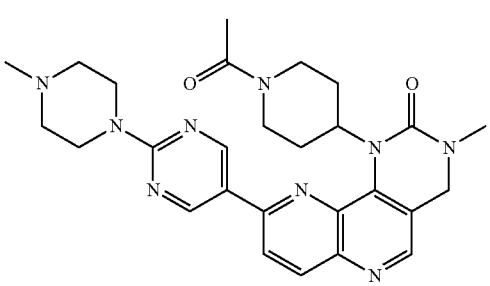 |
| 190 | 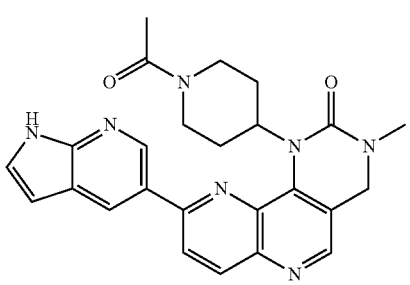 [SMILES: CC(=O)N1CCC(N2C(=O)N(C)Cc3cnc4ccc(-c5cnc6[nH]ccc6c5)nc4c32)CC1] |

| No. | Structural Formula |
|---|---|
| 191 | 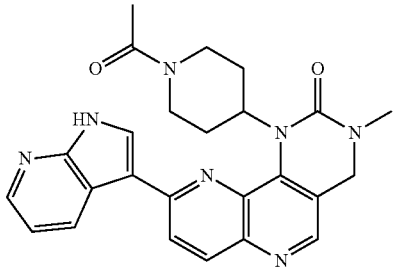 [SMILES: CC(=O)N1CCC(N2C(=O)N(C)Cc3cnc4ccc(-c5c[nH]c6ncccc56)nc4c32)CC1] |
| 192 | 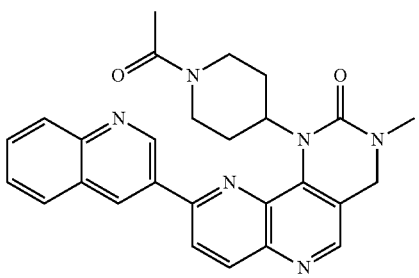 [SMILES: CC(=O)N1CCC(N2C(=O)N(C)Cc3cnc4ccc(-c5cnc6ccccc6c5)nc4c32)CC1] |
| 193 | 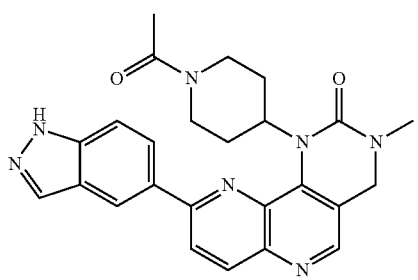 [SMILES: CC(=O)N1CCC(N2C(=O)N(C)Cc3cnc4ccc(-c5ccc6[nH]ncc6c5)nc4c32)CC1] |
| 194 | 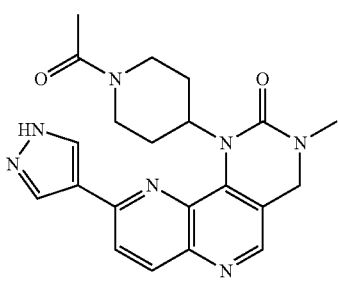 [SMILES: CC(=O)N1CCC(N2C(=O)N(C)Cc3cnc4ccc(-c5cn[nH]c5)nc4c32)CC1] |
| 195 | 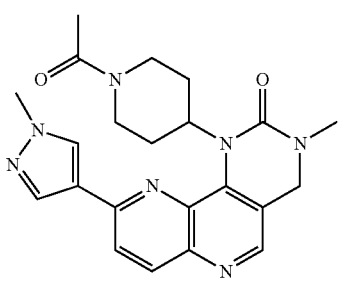 [SMILES: CC(=O)N1CCC(N2C(=O)N(C)Cc3cnc4ccc(-c5cnn(C)c5)nc4c32)CC1] |
| 196 | 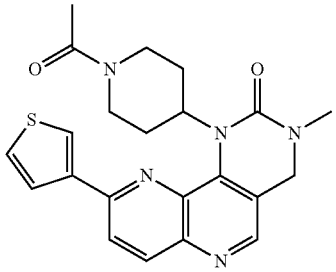 [SMILES: CC(=O)N1CCC(N2C(=O)N(C)Cc3cnc4ccc(-c5ccsc5)nc4c32)CC1] |
| 197 | 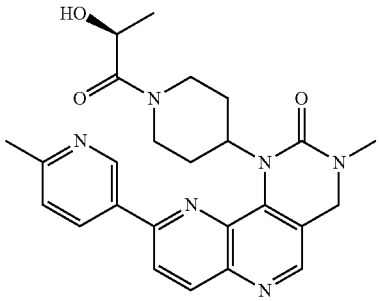 |
| 198 | 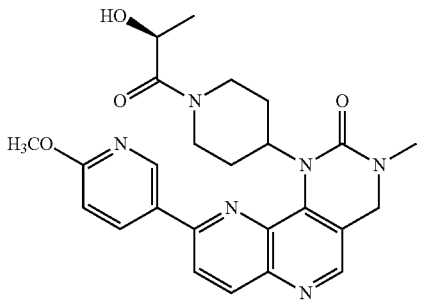 |
| 199 | 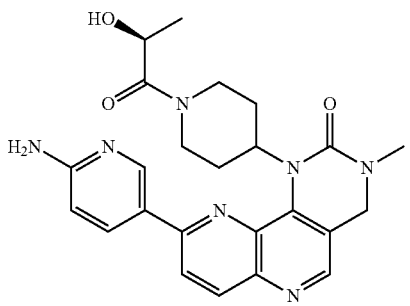 [SMILES: C[C@H](O)C(=O)N1CCC(N2C(=O)N(C)Cc3cnc4ccc(-c5ccc(N)nc5)nc4c32)CC1] |
| 200 | 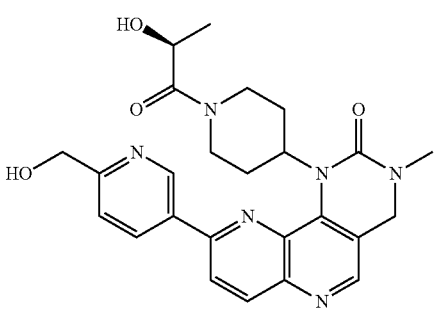 [SMILES: C[C@H](O)C(=O)N1CCC(N2C(=O)N(C)Cc3cnc4ccc(-c5ccc(CO)nc5)nc4c32)CC1] |

| No. | Structural Formula |
|---|---|
| 201 | 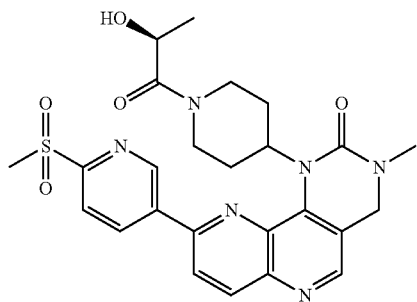 |
| 202 | 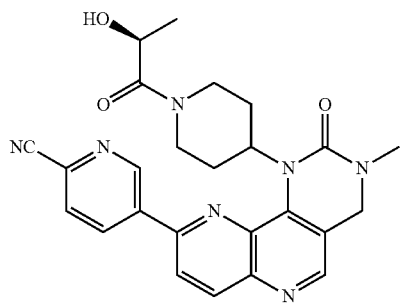 [SMILES: C[C@H](O)C(=O)N1CCC(N2C(=O)N(C)Cc3cnc4ccc(-c5ccc(C#N)nc5)nc4c32)CC1] |
| 203 | 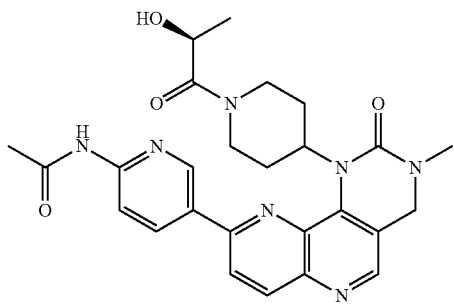 |
| 204 | 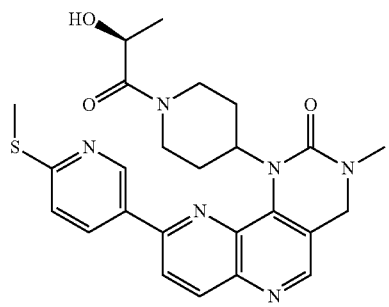 [SMILES: CSc1ccc(-c2ccc3ncc4c(c3n2)N(C2CCN(C(=O)[C@H](C)O)CC2)C(=O)N(C)C4)cn1] |
| 205 | 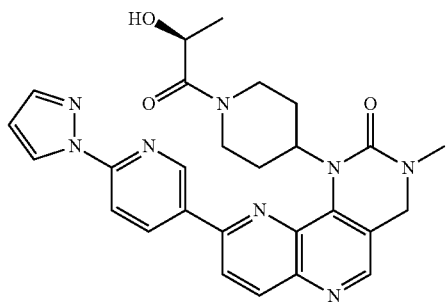 [SMILES: C[C@H](O)C(=O)N1CCC(N2C(=O)N(C)Cc3cnc4ccc(-c5ccc(-n6cccn6)nc5)nc4c32)CC1] |орм
| No. | Structural Formula |
|---|---|
| 206 | 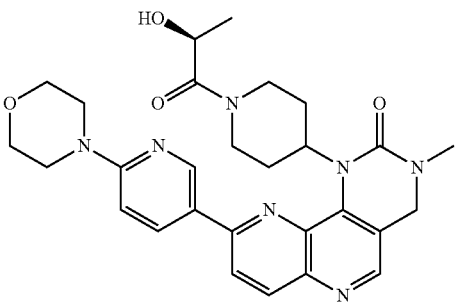 |
| 207 | 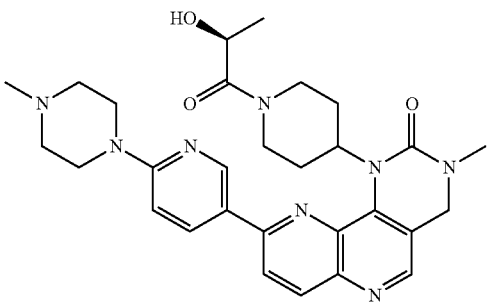 |
| 208 | 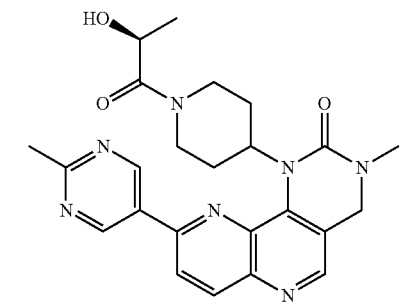 |
| 209 | 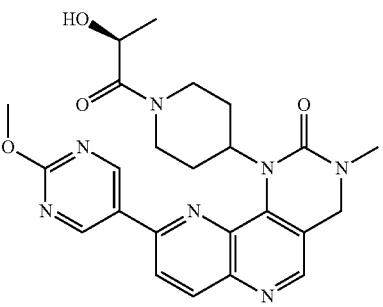 [SMILES: COc1ncc(-c2ccc3ncc4c(c3n2)N(C2CCN(C(=O)[C@H](C)O)CC2)C(=O)N(C)C4)cn1] |
| 210 | 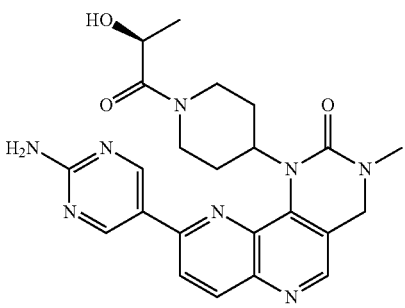 |

| No. | Structural Formula |
|---|---|
| 211 | 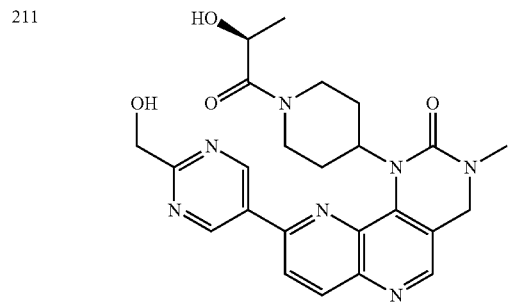 |
| 212 | 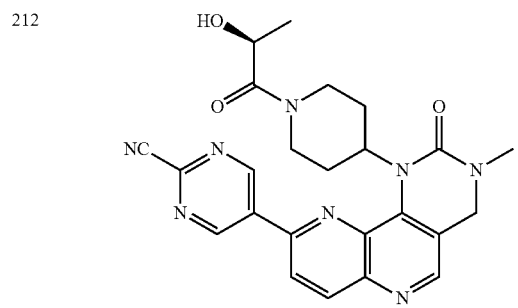 |
| 213 | 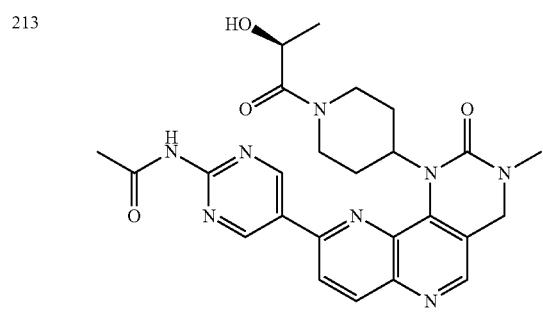 |
| 214 | 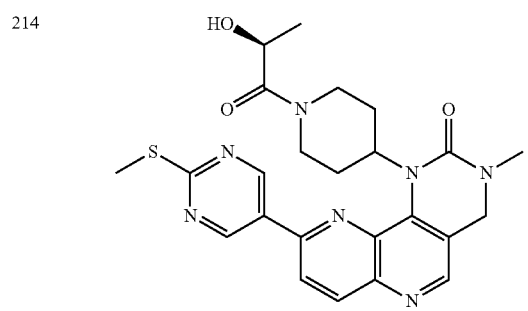 |
| 215 | 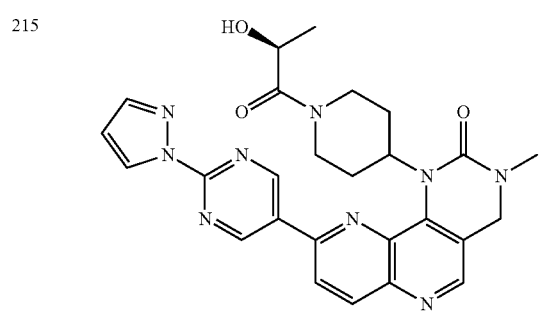 |
| No. | Structural Formula |
|---|---|
| 216 | 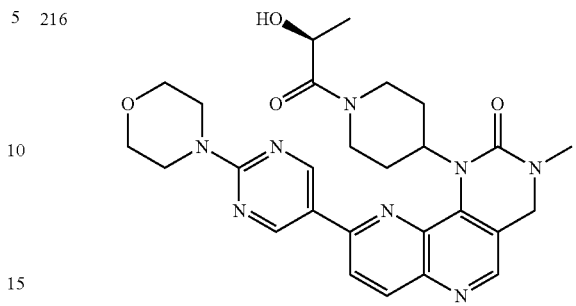 |
| 217 | 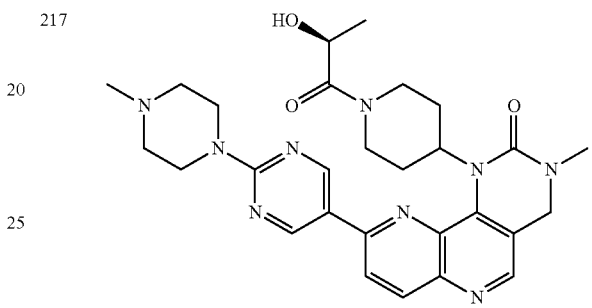 |
| 218 | 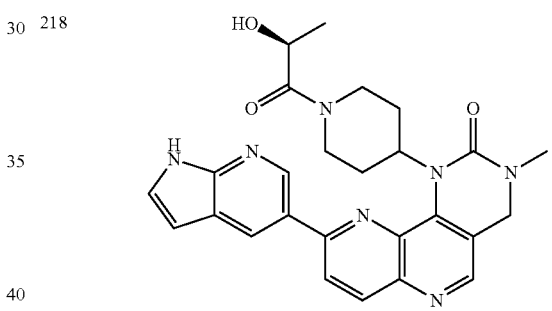 |
| 219 | 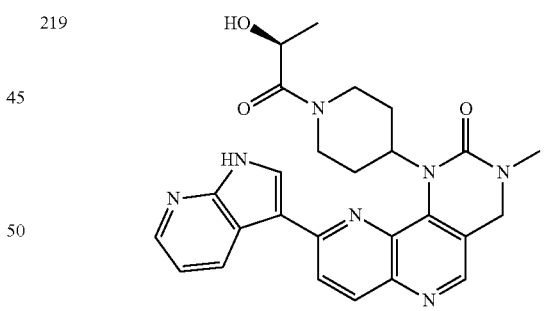 |
| 220 | 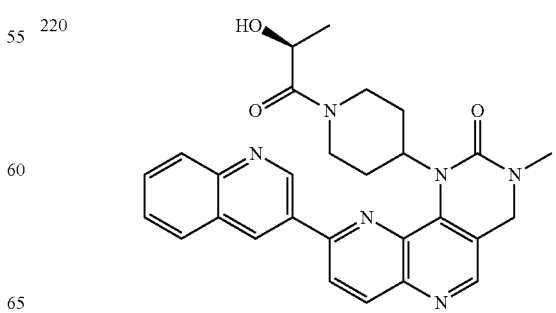 |

| No. | Structural Formula |
|---|---|
| 221 | |
| 222 | |
| 223 | |
| 224 | |
| 225 | |

| No. | Structural Formula |
|---|---|
| 226 | |
| 227 | |
| 228 | |
| 229 | |
| 230 | |

| No. | Structural Formula |
|---|---|
| 231 | |
| 232 | |
| 233 | |
| 234 | |
| 235 | |

| No. | Structural Formula |
|---|---|
| 236 | |
| 237 | |
| 238 | |
| 239 | |
| 240 | |

| No. | Structural Formula |
|---|---|
| 241 | 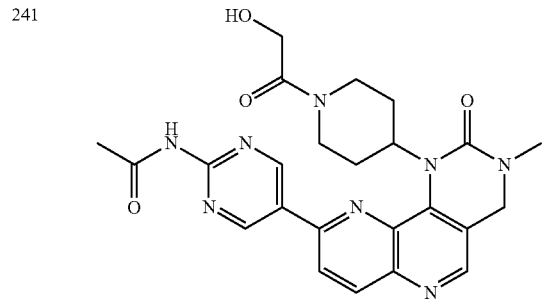 |
| 242 | 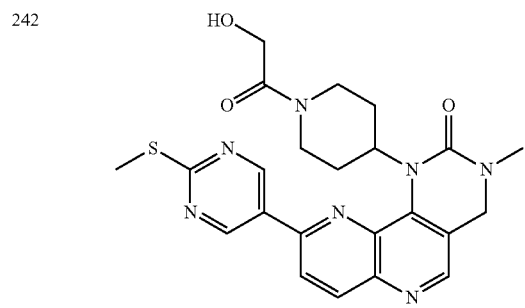 |
| 243 | 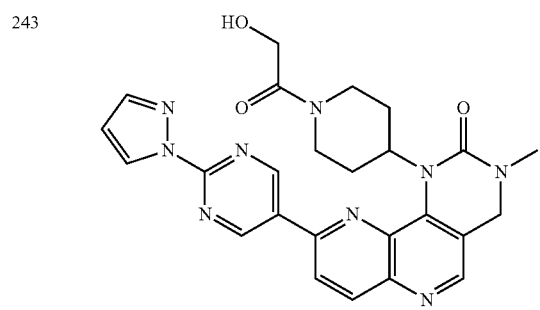 |
| 244 | 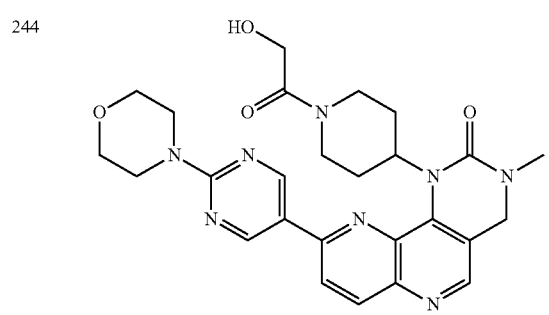 |
| 245 | 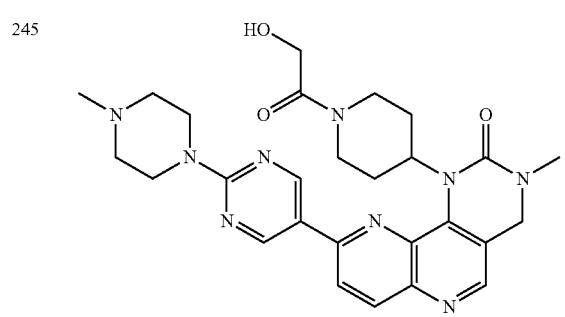 |
| 246 | 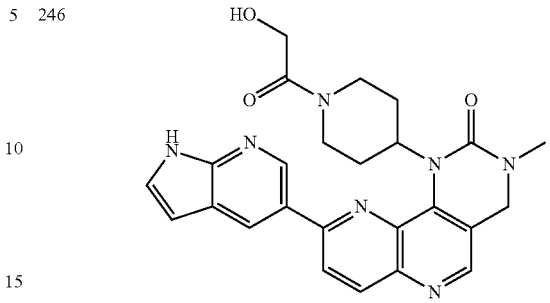 |
| 247 | 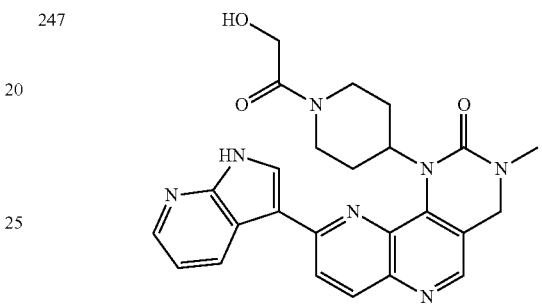 |
| 248 | 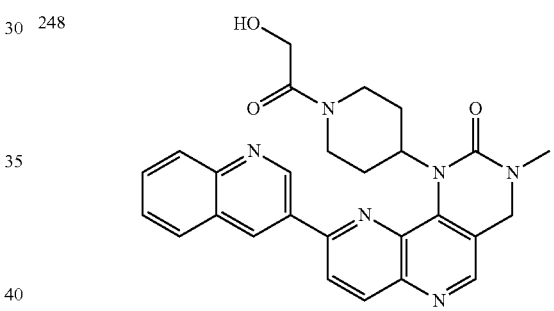 |
| 249 | 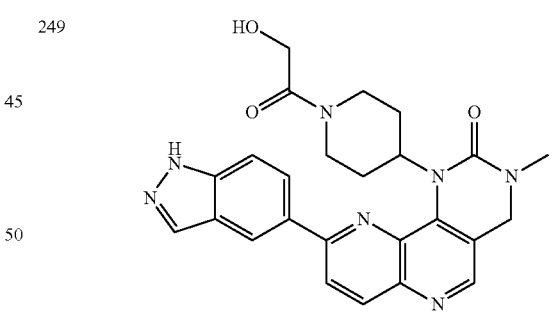 |
| 250 | 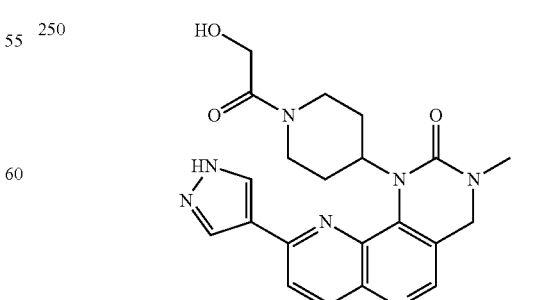 |

| No. | Structural Formula |
|---|---|
| 251 | 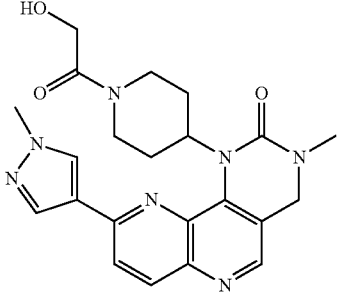 [SMILES: CN1Cc2cnc3ccc(-c4cnn(C)c4)nc3c2N(C2CCN(C(=O)CO)CC2)C1=O] |
| 252 | 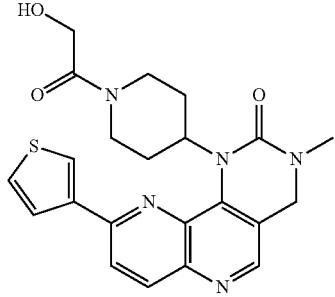 [SMILES: CN1Cc2cnc3ccc(-c4ccsc4)nc3c2N(C2CCN(C(=O)CO)CC2)C1=O] |
| 253 | 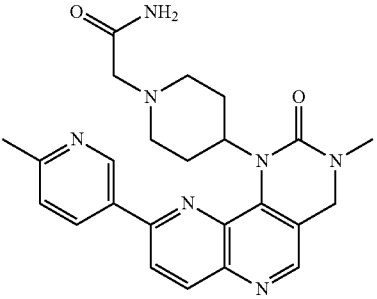 |
| 254 | 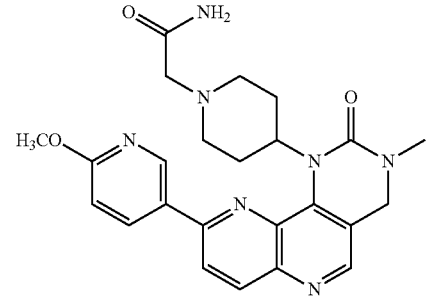 [SMILES: COc1ccc(-c2ccc3ncc4c(c3n2)N(C2CCN(CC(N)=O)CC2)C(=O)N(C)C4)cn1] |
| 255 | 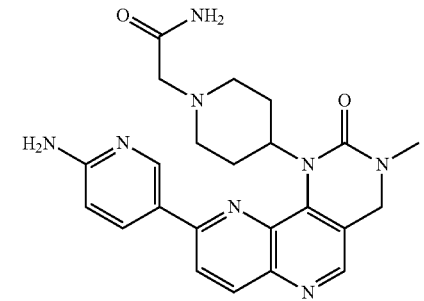 [SMILES: CN1Cc2cnc3ccc(-c4ccc(N)nc4)nc3c2N(C2CCN(CC(N)=O)CC2)C1=O] |
| 256 | 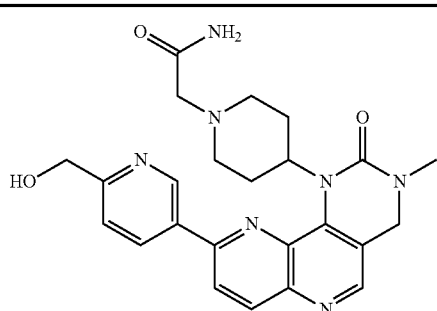 |
| 257 | 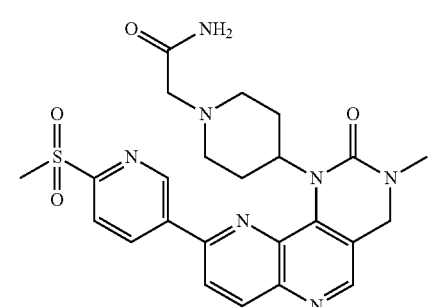 |
| 258 | 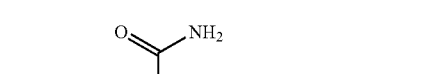 |
| 259 | 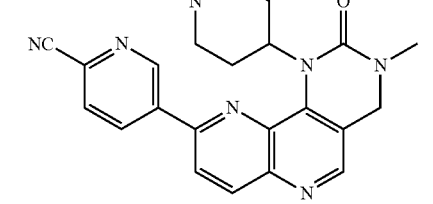 |
| 260 | 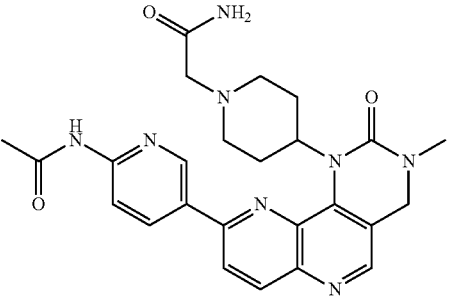 [SMILES: CC(=O)Nc1ccc(-c2ccc3ncc4c(c3n2)N(C2CCN(CC(N)=O)CC2)C(=O)N(C)C4)cn1] |

-continued

| No. | Structural Formula |
|---|---|
| 261 | |
| 262 | |
| 263 | |
| 264 | |
| 265 | |

-continued

| No. | Structural Formula |
|---|---|
| 266 | |
| 267 | |
| 268 | |
| 269 | |
| 270 | |

| No. | Structural Formula |
|---|---|
| 271 | 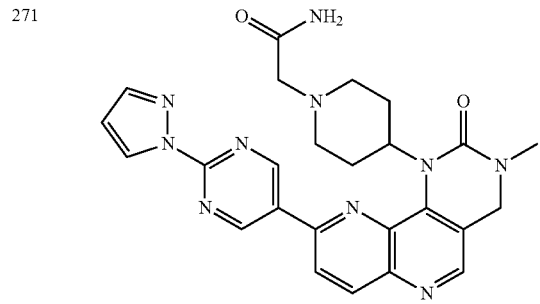 |
| 272 | 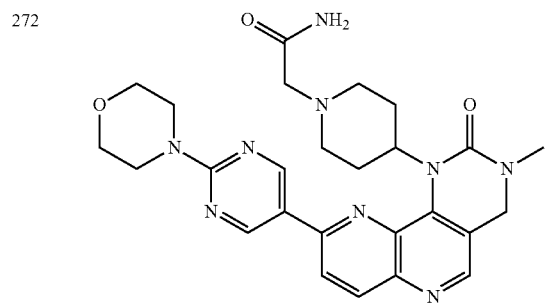 |
| 273 | 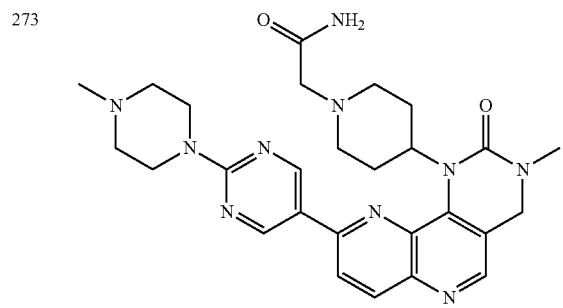 |
| 274 | 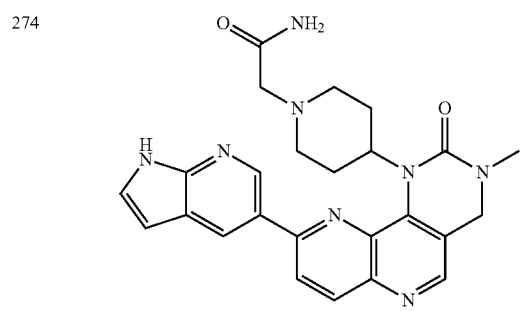 |
| 275 | 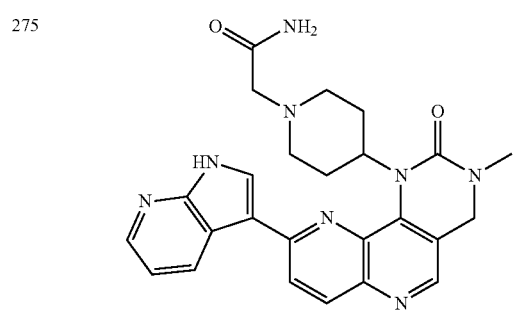 |
| 276 | 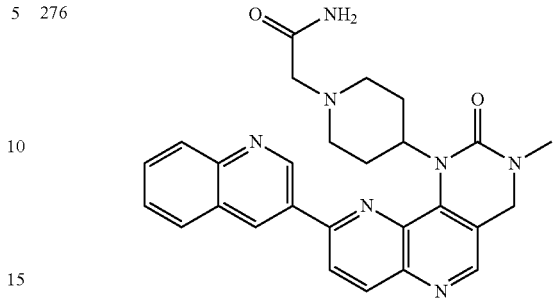 |
| 277 | 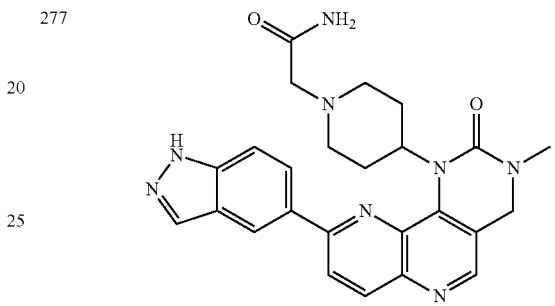 |
| 278 | 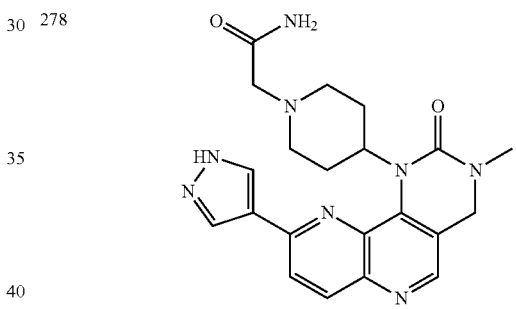 |
| 279 | 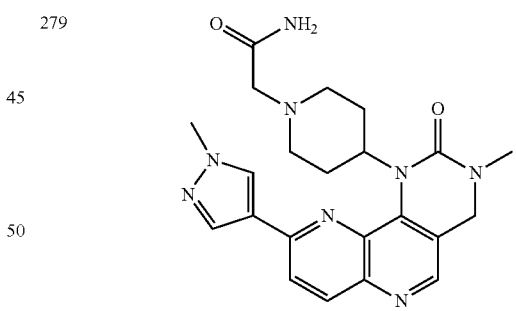 |
| 280 | 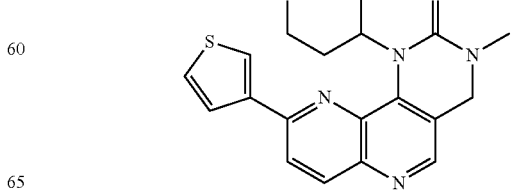 |

| No. | Structural Formula |
|---|---|
| 281 | |
| 282 | |
| 283 | |
| 284 | |
| 285 | |
| 286 | |
| 287 | |
| 288 | |
| 289 | |

| No. | Structural Formula |
|---|---|
| 290 | 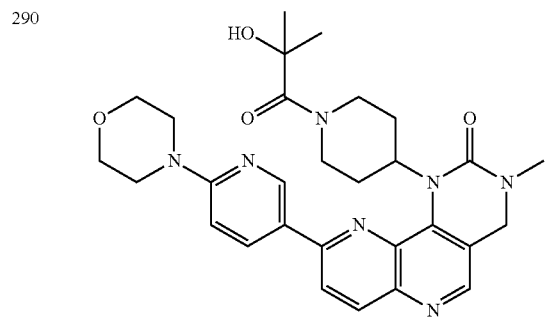 |
| 291 | 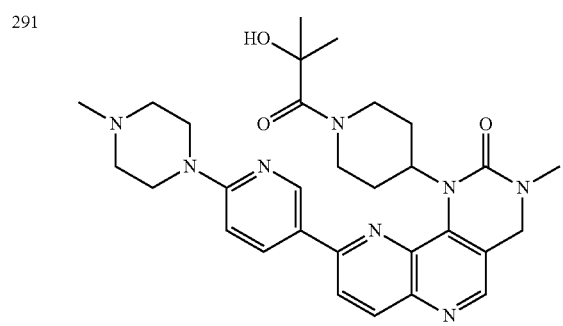 |
| 292 | 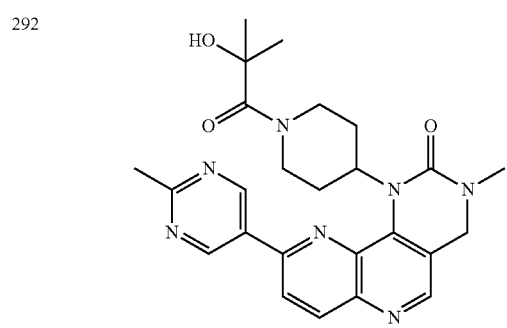 |
| 293 | 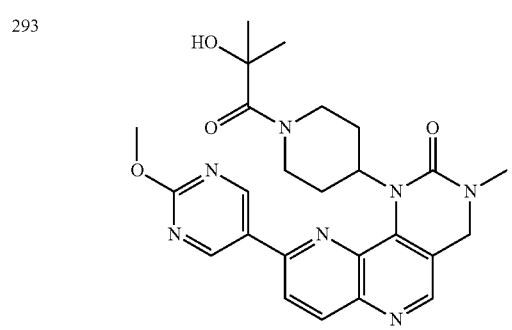 |
| 294 | 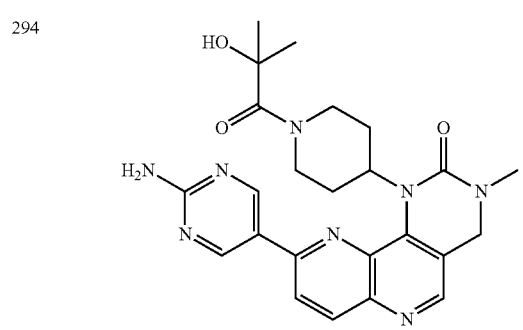 |
| No. | Structural Formula |
|---|---|
| 295 | 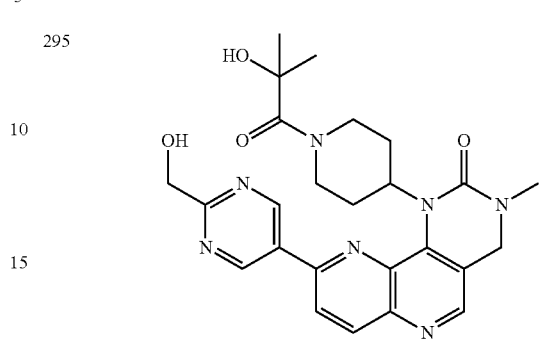 |
| 296 | 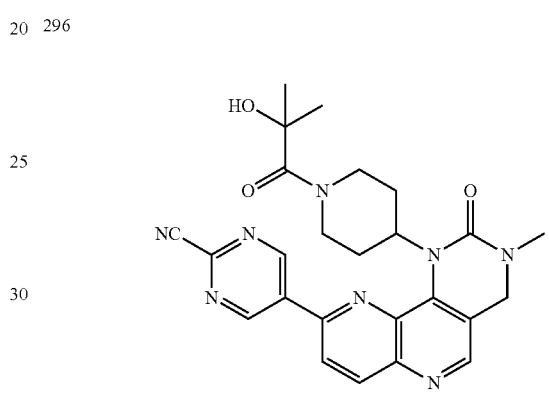 |
| 297 | 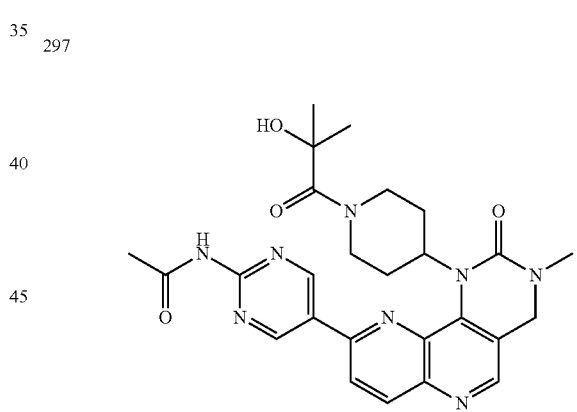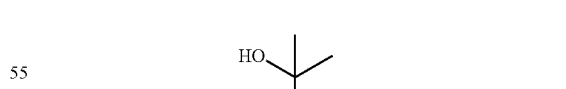 |
| 298 | 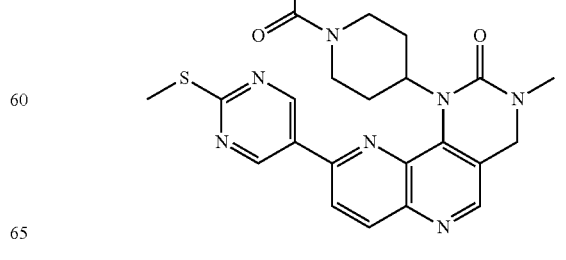 |

| No. | Structural Formula |
|---|---|
| 299 | 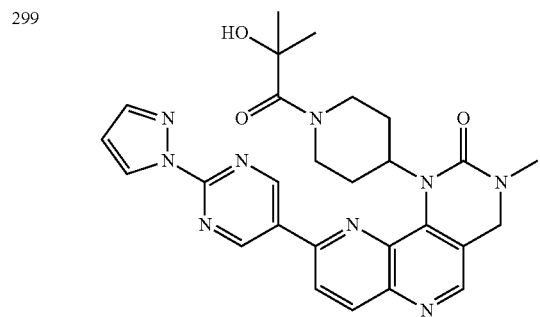 |
| 300 | 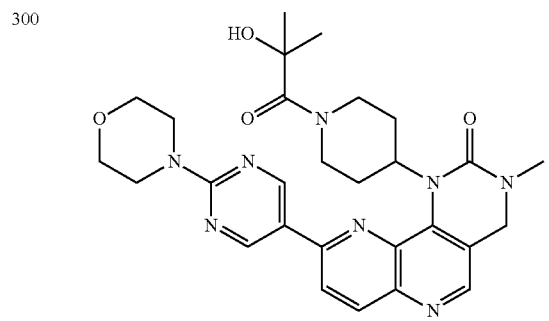 |
| 301 | 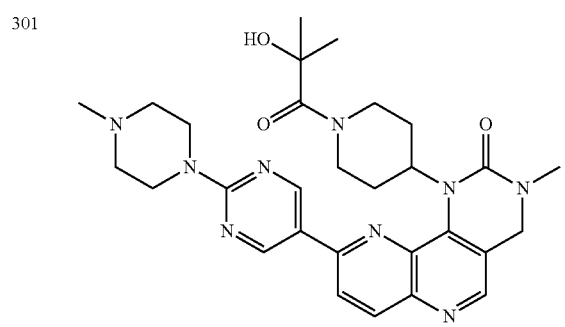 |
| 302 | 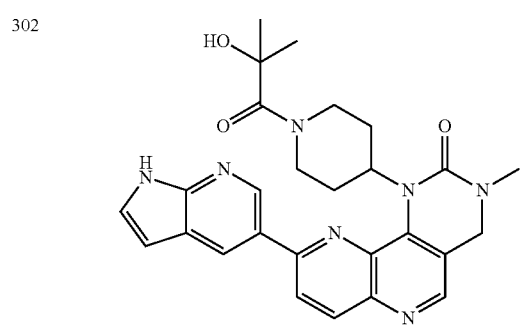 |
| 303 | 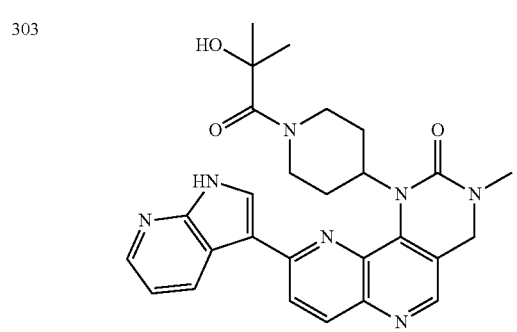 |
| No. | Structural Formula |
|---|---|
| 304 | 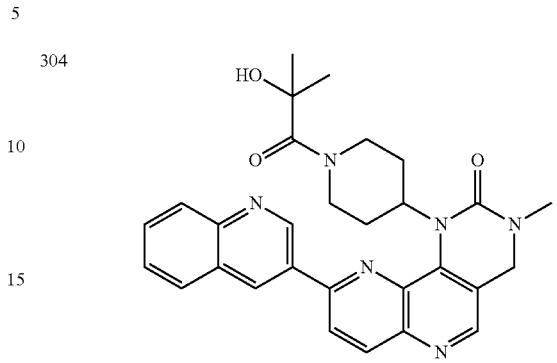 |
| 305 | 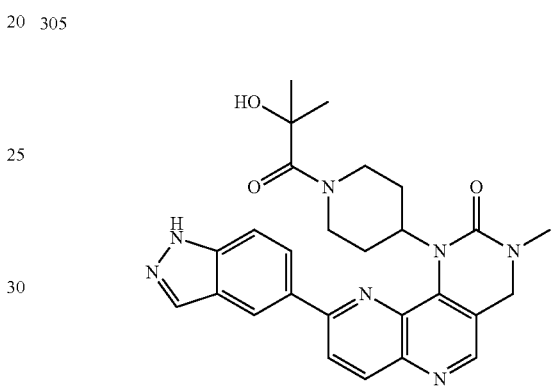 |
| 306 | 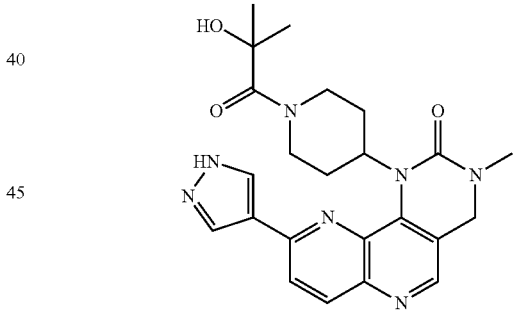 |
| 307 |  |

| No. | Structural Formula |
|-----|-------------------|
| 308 | 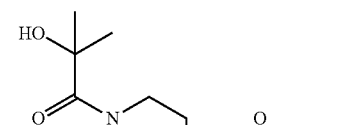 |

The term "halogen" as used herein includes fluorine, chlorine, bromine and iodine.

The term "$C_{1-6}$ alkyl" may be linear or branched and includes for example "$C_{1-4}$ alkyl", "$C_{1-3}$ alkyl", "$C_{1-2}$ alkyl". Examples include, but are not limited to, methyl, ethyl, n-propyl, isopropyl, n-butyl, 2-methylpropyl, 1-methylpropyl, 1,1-dimethylethyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl and the like.

The term "$C_{3-8}$ cycloalkyl" as used herein includes for example "$C_{3-7}$ cycloalkyl", "$C_{3-6}$ cycloalkyl", "$C_{4-6}$ cycloalkyl" and "$C_{5-6}$ cycloalkyl". Examples include, but are not limited to, cyclopropyl, cyclobutyl, cyclopentyl, cyclohexyl, cycloheptyl, cyclooctyl and the like.

The term "$C_{2-8}$ alkenyl" as used herein may be linear or branched or cyclic, and includes for example "$C_{2-5}$ alkenyl", "$C_{2-4}$ alkenyl", "$C_{2-3}$ alkenyl" and "$C_{3-6}$ cycloalkenyl". Examples include, but are not limited to, ethenyl, 1-propenyl, 2-propenyl, 1-butenyl, 2-butenyl, 2-methyl-1-propenyl, 1-methyl-2-propenyl, 1-pentenyl, 2-pentenyl, 2-methyl-1-butenyl, 1-methyl-2-butenyl, 3-methyl-2-butenyl, 2-methyl-3-butenyl, 3-methyl-3-butenyl, 1,1-dimethyl-2-propenyl, 1-ethyl-2-propenyl, 3-hex enyl, 2-methyl-1-pentenyl, 3-methyl-1-pentenyl, 1-methyl-2-pentenyl, 3-methyl-2-pentenyl, 1-methyl-3-pentenyl, 2-methyl-3-pentenyl, 4-methyl-3-pentenyl, 1-methyl-4-pentenyl, 2-methyl-4-pentenyl, 1,1-dimethyl-2-butenyl, 1,1-dimethyl-3-butenyl, 1,2-dimethyl-3-butenyl, 1,3-dimethyl-2-butenyl, 2,3-dimethyl-1-butenyl, 2-ethyl-1-butenyl, 2-ethyl-3-butenyl, 2-heptenyl, 3-heptenyl, 4-heptenyl, 1-octenyl, 2-octenyl, 4-octenyl, 1,3-butadienyl, 1,4-pentadienyl, 2,4-pentadienyl, 1,4-hexadienyl, 2,4-hexadienyl, cyclopentenyl, 1,3-cyclopentadienyl, cyclohexenyl, 1,4-cyclohexadienyl, cycloheptenyl, 1,4-cycloheptadienyl, cyclooctenyl and 1,5-cyclooctadienyl and the like. The double bond may be optionally cis- and trans-.

The term "$C_{2-8}$ alkynyl" as used herein may be linear or branched and includes for example "$C_{2-5}$ alkynyl", "$C_{2-4}$ alkynyl" and "$C_{2-3}$ alkynyl". Examples include, but are not limited to, ethynyl, 1-propinyl, 2-propinyl, 2-butynyl, 3-butynyl, 1-methyl-2-propinyl, 2-pentynyl, 3-pentynyl, 2-methyl-3-butynyl, 2-hexynyl, 3-hexynyl, 4-methyl-2-pentynyl, 2-methyl-3-pentynyl, 2-methyl-4-pentynyl, 3-methyl-4-pentynyl, 1,2-dimethyl-3-butynyl, 2,2-dimethyl-3-butynyl, 1-ethyl-2-butynyl, 1-ethyl-3-butynyl, 2-ethyl-3-butynyl, 2-heptynyl, 3-heptynyl, 4-methyl-2-hexynyl, 2-methyl-3-hexynyl, 2-methyl-4-hexynyl, 3-methyl-5-hexynyl, 2-octynyl, 4-octynyl, 4-methyl-2-heptynyl, 2-methyl-3-heptynyl, 5-methyl-3-heptynyl, 1-methyl-4-heptynyl, 2-methyl-5-heptynyl, 2-methyl-6-heptynyl and the like.

The term "$C_{1-6}$ alkoxy" as used herein refers to "$C_{1-6}$ alkyl-O—" wherein "$C_{1-6}$ alkyl" is defined as above.

The term "$C_{1-6}$ alkyl carbonyl" as used herein refers to "$C_{1-6}$ alkyl-C(O)—" wherein "$C_{1-6}$ alkyl" is defined as above.

The term "6- to 14-membered aryl" as used herein includes 6- to 8-membered monocyclic aryl and 8- to 14-membered fused aryl. 6- to 8-membered monocyclic aryl includes for example phenyl and cyclooctatetraenyl. 8- to 14-membered fused aryl includes for example naphthyl, phenanthryl, 2,3-dihydro-1H-indenyl, 1H-indenyl, 1,2,3,4-tetrahydronaphthyl, 1,4-dihydronaphthyl and the like.

The term "5- to 14-membered heteroaryl" as used herein includes 5- to 8-membered monocyclic heteroaryl and 6- to 14-membered fused heteroaryl, wherein heteroatoms are nitrogen, oxygen, sulfur and the like. It includes the case that a carbon atom, a nitrogen atom or a sulfur atom is substituted by oxo.

Examples of 5- to 8-membered monocyclic heteroaryl include, but are not limited to, furyl, thienyl, pyrrolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, 2-pyridone, 4-pyridone, pyrimidinyl, 1,4-dioxinyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,3,5-triazinyl, 1,2,4,5-tetrazinyl, azepinyl, 1,3-diazepinyl, azacyclooctatetraenyl and the like. It is preferably 5- to 6-membered monocyclic heteroaryl.

Examples of 6- to 14-membered fused heteroaryl include, but are not limited to, benzofuryl, isobenzofuryl, benzothienyl, indolyl, isoindolyl, benzoxazolyl, benzimidazolyl, indazolyl, benzotriazolyl, quinolyl, 2-quinolinone, 4-quinolinone, 1-isoquinolinone, isoquinolyl, acridinyl, phenanthridinyl, benzopyridazinyl, phthalazinyl, quinazolinyl, quinoxalinyl, phenazinyl, pteridinyl, purinyl, naphthyridinyl, phenazinyl, phenothiazinyl and the like. It is preferably 9- to 10-membered fused heteroaryl.

The term "3- to 14-membered heterocyclic group" as used herein includes 3- to 8-membered monocyclic heterocyclic group and 6- to 14-membered fused heterocyclic group, wherein heteroatoms are nitrogen, oxygen, sulfur and the like. It includes the case that a carbon atom, a nitrogen atom or a sulfur atom is substituted by oxo.

Examples of 3- to 8-membered monocyclic heterocyclic group include, but are not limited to, aziridinyl, 2H-aziridinyl, diazirinyl, 3H-diazirinyl, azetidinyl, 1,4-dioxanyl, 1,3-dioxanyl, 1,3-dioxolanyl, 1,4-dioxinyl, tetrahydrofuryl, dihydropyrrolyl, pyrrolidinyl, imidazolidinyl, 4,5-dihydroimidazolyl, pyrazolidinyl, 4,5-dihydropyrazolyl, 2,5-dihydrothienyl, tetrahydrothienyl, 4,5-dihydrothiazolyl, piperidinyl, piperazinyl, morpholinyl, 4,5-dihydrooxazolyl, 4,5-dihydroisoxazolyl, 2,3-dihydroisoxazolyl, 2H-1,2-oxazinyl, 6H-1,3-ox azinyl, 4H-1,3-thiazinyl, 6H-1,3-thiazinyl, 2H-pyranyl, 2H-pyran-2-keto, 3,4-dihydro-2H-pyranyl and the like. It is preferably 5- to 6-membered monocyclic heterocyclic group.

Examples of 6- to 14-membered fused heterocyclic group include, but are not limited to, tetrahydroimidazo[4,5-c]pyridyl, 3,4-dihydroquinazolinyl, 1,2-dihydroquinoxalinyl, benzo[d][1,3]dioxolyl, 1,3-dihydroisobenzofuryl, 2H-chromenyl, 2H-chromene-2-keto, 4H-chromenyl, 4H-chromene-4-keto, chromanyl, 4H-1,3-benzoxazinyl, 4,6-dihydro-1H-furo[3,4-d]imidazolyl, 3a,4,6,6a-tetrahydro-1H-furo[3,4-d]imidazolyl, 4,6-dihydro-1H-thieno[3,4-d]

imidazolyl, 4,6-dihydro-1H-pyrrolo[3,4-d]imidazolyl, 4,5,6,7-tetrahydro-1H-benzo[d]imidazolyl and the like. It is preferably 9- to 10-membered fused heterocyclic group.

The term "7- to 12-membered endocyclic group" as used herein refers to 7- to 12-membered endocyclic group in which any two rings share two non-adjacent atoms and all ring atoms are carbon atoms, or 7- to 12-membered endo-heterocyclic group containing at least one hetero atoms such as nitrogen, oxygen and sulfur and the like. The 7- to 12-membered endocyclic group and 7- to 12-membered endo-heterocyclic group may be saturated or partially saturated.

Saturated endocyclic group refers to an endocyclic group in which all rings are saturated, and preferably 7- to 8-membered saturated endocyclic group. Specific examples include, but are not limited to,

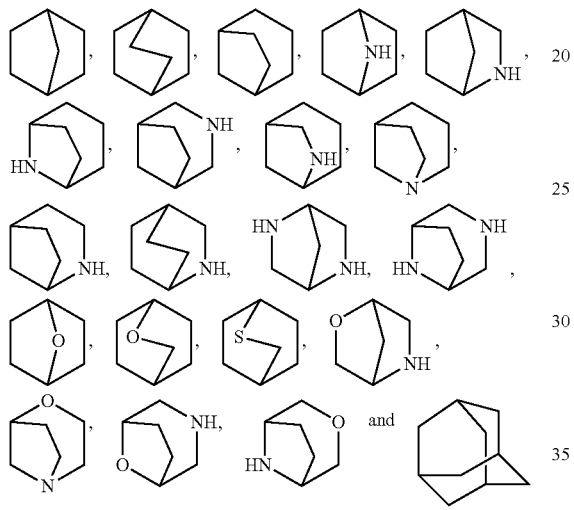

and the like.

Partially saturated endocyclic group means that at least one ring in the endocyclic group is an unsaturated cyclic group, preferably a 7- to 8-membered partially saturated endocyclic group, specific examples include, but are not limited to,

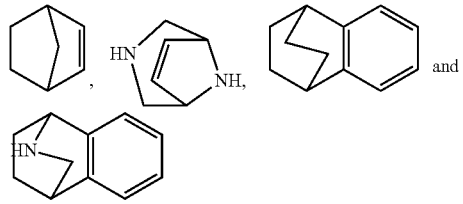

and the like.

The term "7- to 12-membered spirocyclic group" as used herein refers to 7- to 12-membered spirocyclic group wherein at least two rings share one atom and all ring atoms are carbon atoms, or 7- to 12-membered spiro-heterocyclic group containing at least one hetero atom such as nitrogen, oxygen and sulfur and the like. The 7- to 12-membered spirocyclic group and 7- to 12-membered spiro-heterocyclic group may be saturated or partially saturated.

Saturated spirocyclic group ring group means that all rings in the spirocyclic group are saturated cyclic groups. Examples include, but are not limited to,

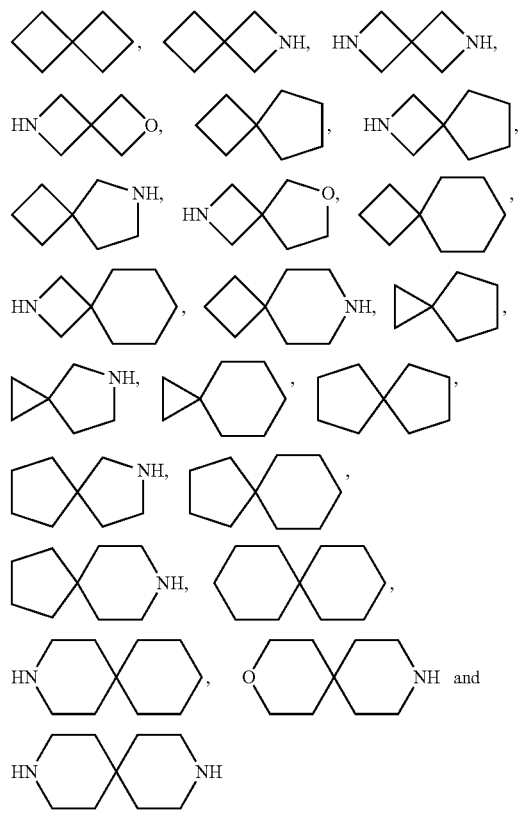

and the like.

Partially saturated spirocyclic group means that at least one ring in the spirocyclic group is an unsaturated cyclic group. Examples include, but are not limited to,

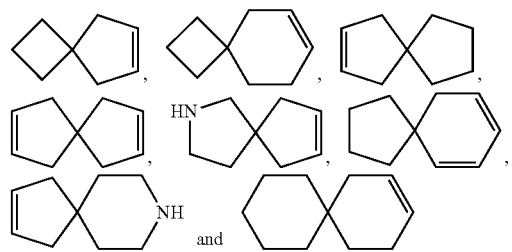

and the like.

The compounds of the present invention may be prepared by the following method and/or other synthesis technologies known by a person skilled in the art, but the method is not limited to the following.

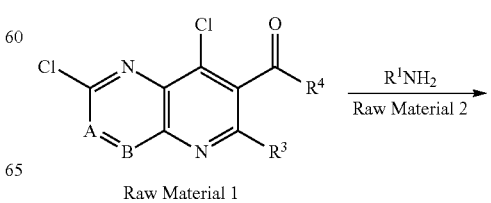

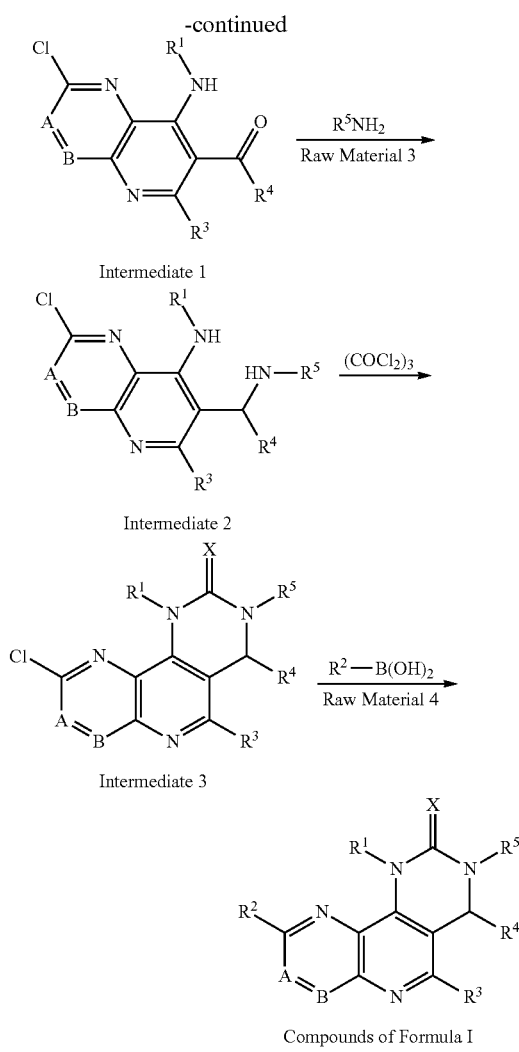

Compounds of Formula I

In the reaction equation, $R^1$, $R^2$, $R^3$, $R^4$, $R^5$, X, A and B are as defined above.

Reaction Steps:

(1) Preparation of Intermediate 1

The raw material 2 was added to a solution of the raw material 1 in alcohols (e.g. methanol, ethanol, isopropanol, tert-butanol, etc.) and heated under reflux. The end of the reaction was determined by thin layer chromatography, the solvent was rotary evaporated to dry, and the residue was subjected to column chromatography to give Intermediate 1.

(2) Preparation of Intermediate 2

Method 1: Intermediate 1 was dissolved in an organic solvent of alcohols (e.g. methanol, ethanol, isopropanol, tert-butanol, etc.) or dichloromethane, and added the raw material 3, then added a small amount of acetic acid to adjust the system to be weakly acidic. After a period of stirring, sodium triacetoxyborohydride was added in batches and stirring was continued. The reaction was quenched with water, and extracted with an organic solvent of halogenated hydrocarbon (such as chlorobenzene, dichlorobenzene, chloromethane, or dichloromethane). The organic phase was concentrated and subjected to column chromatography to give Intermediate 2.

Method 2: Intermediate 1 and the raw material 3 were dissolved in an organic solvent of alcohols (e.g. methanol, ethanol, isopropanol, tert-butanol, etc.), and after a period of stirring at room temperature, sodium borohydride was added in batches and stirring was continued. The reaction was quenched with water, rotary evaporated to remove most of the alcohol solvent, and extracted with an organic solvent of halogenated hydrocarbon (such as chlorobenzene, dichlorobenzene, chloromethane, dichloromethane and the like). The organic phase was concentrated and subjected to column chromatography to provide Intermediate 2.

(3) Preparation of Intermediate 3

In a dry reaction flask, triphosgene and triethylamine were dissolved in tetrahydrofuran or dichloromethane. Intermediate 2 was added under cooling in an ice bath and stirred. The reaction was quenched with saturated aqueous sodium carbonate solution, and extracted with an organic solvent of halogenated hydrocarbon (such as chlorobenzene, dichlorobenzene, chloromethane or dichloromethane and the like), washed with a saturated aqueous solution of sodium carbonate and saturated brine. The organic layer was dried with a drying agent (such as anhydrous calcium sulfate, anhydrous sodium sulfate or anhydrous magnesium sulfate and the like), and purified by column chromatography to give Intermediate Compound 3.

(4) Preparation of Compounds of General Formula I

Intermediate 3, the raw material 4, palladium catalysts (including but not limited to $Pd(PPh_3)_4$, $Pd(dppf)_2Cl_2$ and $Pd(PPh_3)_2Cl_2$) and a base (including but not limited to $CH_3COOK$, $K_3PO_4$ and $K_2CO_3$) were added sequentially to an organic solvent (including but not limited to dioxane, DMSO, DMF and toluene) and a small amount of water (v:v=2~4:1). The reaction mixture was heated under nitrogen atmosphere. The reaction was quenched with water, and extracted with an organic solvent of halogenated hydrocarbon (such as chlorobenzene, dichlorobenzene, chloromethane or dichloromethane and the like). The organic layer was dried with a drying agent (such as anhydrous calcium sulfate, anhydrous sodium sulfate or anhydrous magnesium sulfate and the like) and subjected to column chromatography to give the compounds of general formula I.

In the reaction, the functional groups in the material compounds, which should not be involved in the reaction, may be protected in advance, and then all or part of the protecting groups can be removed according to conventional methods. For example, if there is a proton of amino acid, it can be protected by a conventional "amino protecting group".

"A pharmaceutically acceptable salt" of the present compounds of general formula (I) refers to salts formed by the compounds of general formula (I) containing a basic nitrogen atom with an inorganic acid, organic acid or organic protonic acid, including hydrochloride and so on.

"An ester" of the present compounds of general formula (I) refers to those that can be hydrolyzed in the human body to become the parent compounds. It is apparent to those skilled in the art that an ester of the present compounds of general formula (I), which can be easily hydrolysable, may be formed at the free carboxyl or hydroxy group of the compounds, and it can be prepared by a conventional method.

"A solvate" of the present compounds of general formula (I) refers to their association with a solvent. The solvent may be an organic solvent (such as ethanol, methanol, propanol, acetonitrile, etc.) and water. For example, the present compounds can form ethanolate with ethanol, and hydrate with water.

When one or more asymmetric carbon atoms exist in the present compounds of general formula (I), there are enantiomers. When the compounds contain an alkenyl group or a cyclic structure, there are cis/trans isomers. When the compounds contain a ketone or an oxime, there are tautomers. All these enantiomers, diastereomers, racemic isomers, cis/trans isomers, tautomers, geometric isomers, epimerides and mixture thereof are included within the scope of the present invention.

The present compounds of general formula (I), a pharmaceutically acceptable salt, ester, solvate or stereoisomer thereof is useful for treating and/or preventing proliferative diseases including cancer and non-cancer diseases, wherein the cancer disease is selected from a brain tumor, lung cancer, non-small cell lung cancer, squamous cell carcinoma, bladder cancer, stomach cancer, ovarian cancer, peritoneal cancer, pancreatic cancer, breast cancer, head and neck cancer, cervical cancer, endometrial cancer, colorectal cancer, liver cancer, kidney cancer, esophageal adenocarcinoma, esophageal squamous cell carcinoma, solid tumors, non-Hodgkin's lymphoma, glioma, glioblastoma multiforme, gliosarcoma, prostate cancer, thyroid carcinoma, genital tract carcinoma, carcinoma in situ, lymphoma, histiocytic lymphoma, neurofibromatosis, bone cancer, skin cancer, brain cancer, colon cancer, testicular cancer, small cell lung cancer, gastrointestinal stromal tumor, prostate tumor, mast cell tumor, multiple myeloma, melanoma, glioma, glioblastoma, astrocytoma, neuroblastoma, sarcomas; and the non-cancer disease is selected from a skin disease or benign prostate hyperplasia.

The present compounds of general formula (I), a pharmaceutically acceptable salt, ester, solvate or stereoisomer thereof can be made into pharmaceutical preparations with one or more pharmaceutically acceptable carriers. Said pharmaceutical preparations refer to conventional preparations in the clinical use, and can be orally or parenterally applied to patients in need of such treatment. For oral administration, they can be made into conventional solid preparations such as tablets, capsulas, pills, granules, etc., as well as oral liquid preparations, such as oral solutions, oral suspensions, syrups, etc. For parenteral administration, they can be made into injections, including injection solution, a sterile powder for injection, concentrated solution for injection and suspension for injection. For rectal administration, they can be made into suppositories and the like. For transpulmonary administration, they can be made into inhalations or aerosols and the like. For topical or percutaneous administration, they can be made into ointments, pastes, creams, lotions, gels, powders, solutions or transdermal stickers and the like. These preparations can be prepared by a conventional method, adding pharmaceutically acceptable carriers such as excipients, binders, moistening agents, disintegrating agents, thickeners and the like.

The administration amount and frequency of the present compounds can be adjusted according to the judgment of the clinician or pharmacist, for example according to the patient's age, weight, the severity of the symptoms. Generally, the daily dose of the present compounds when administrated in a single dose or divided doses may be 20 mg~500 mg, preferably 50~300 mg.

The compounds of Formula (I), a pharmaceutically acceptable salt, ester, solvate, or stereoisomer thereof can be used in combination with one or more anti-cancer agents and immunosuppressants. The anti-tumor agents and immunosuppressants are selected from anti-metabolites, including but not limited to, capecitabine, gemcitabine and pemetrexed disodium; growth factor inhibitors, including but not limited to, pazopanib, imatinib, erlotinib, lapatinib, gefitinib and vandetanib; antibodies, including but not limited to Herceptin and Avastin; mitotic inhibitors, including but not limited to paclitaxel, vinorelbine, docetaxel and doxorubicin; anti-tumor hormones, including but not limited to letrozole, tamoxifen, fulvestrant, flutamide and triptorelin; alkylating agents, including but not limited to cyclophosphamide, nitrogen mustard, melphalan, chlorambucil and carmustine; platinum metals, including but not limited to carboplatin, cisplatin and oxaliplatin; topoisomerase inhibitors, including but not limited to camptothecin, topotecan and irinotecan; immunosuppression categories, including but not limited to everolimus, sirolimus and temsirolimus; purine analogues, including but not limited to, 6-mercaptopurine, 6-thioguanine and azathioprine; antibiotics, including but not limited to streptozotocin D, daunorubicin, doxorubicin, mitoxantrone, bleomycin and plicamycin; adrenal cortex inhibitor, including but not limited to aminoglutethimide.

The present invention also relates to a method for treating and/or preventing proliferative diseases, which comprises administering to a patient a therapeutically effective amount of the present compounds of general formula (I), a pharmaceutically acceptable salt, ester, solvate or stereoisomer thereof.

PREFERRED EMBODIMENTS

The beneficial effects of the present compounds will be further elaborated hereinafter. Other compounds of the present invention have the same beneficial effects with the compounds listed in the experiments, but it should not be understood that the present compounds only have the following beneficial effects.

Experimental Example 1

Enzymatic Inhibitory Activity of the Present Compounds In Vitro

Test Substances

Tested compounds: the present compounds, made by the applicant, see Preparative Examples for the chemical names and structures of each compound;

Control compounds: BGT-226 and BEZ-235 disclosed in WO2006122806 (published on Nov. 23, 2006), which were prepared according the methods disclosed in the application.

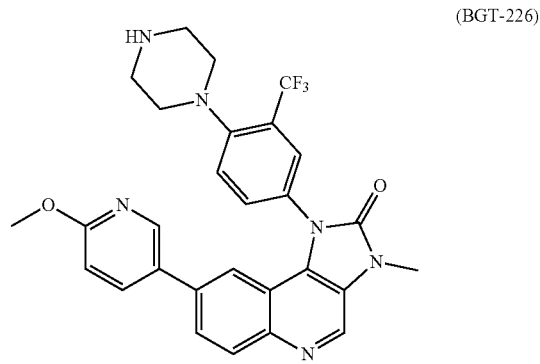

(BGT-226)

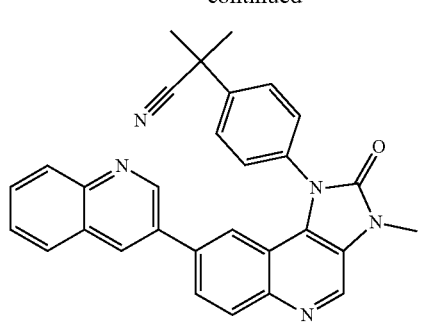
(BEZ-235)

Experimental Method 1 Activity Test

The abbreviations in the following experiments have the meanings as below:
HEPES: hydroxyethylpiperazine-ethane sulfonic acid;
EDTA: ethylenediaminetetraacetic acid;
CHAPS: 3-((3-Cholamidopropyl)dimethylammonium)-1-propanesulfonate
DTT: dithiothreitol;
PIP2: phosphatidylinositol-4,5-bisphosphate;
ATP: adenosine triphosphate (Sigma);
DMSO: dimethylsulfoxide;
Tween-20: Tween 20;
Determination of the inhibitory activity of PI3K
1. Preparation of test reagents
① 1× kinase buffer (50 mM HEPES, pH 7.5, 3 mM $MgCl_2$, 1 mM EGTA, 100 mM NaCl, 0.03% CHAPS, 2 mM DTT);
② 4× kinase solution (added PI3K a kinase to 1× kinase buffer to provide 4× kinase solution with a final concentration of 1.65 nM);
③ 2× substrate solution (added the substrates of PIP2 and ATP into 1× kinase buffer to provide 2× substrate solution with PIP2 final concentration of 50 μM and ATP final concentration of 25 μM);
④ 4× test substance solutions (100× test substance solutions with different concentration gradients were prepared using 100% DMSO, and diluted 25-fold with 1× kinase buffer to give 4× test substance solutions with different concentration gradients);
⑤ Invitrogen's activity test kit with the test solution was kept stand to room temperature.
2. 2.5 μL of 4× test solution was added to a 384-well plate in parallel;
3. added 2.54 μL of 4× kinase solution and incubated for 10 min;
4. then added 5 μL of 2× solutions of PIP2 and ATP substrates and incubated for 1 h at room temperature;
5. finally, added 10 μL of test solution to quench the reaction, and read after 15 min;
6. $IC_{50}$ value was obtained via curve fitting.

Inhibition rate (%)=(sample value−minimum)/(maximum−minimum)×100

Maximum refers to the readings of control wells without enzyme, minimum refers to the readings of DMSO control wells.

$IC_{50}$ value was obtained via curve fitting using a soft of Graphpad 5.0.

Determination of the Inhibitory Activity of mTOR
1. Preparation of test reagents
① 1× kinase buffer (50 mM HEPES, pH 7.5, 10 mM $MgCl_2$, 1 mM EGTA, 3 mM MnCl, 0.01% Tween-20, 2 mM DTT);
② 4× kinase solution (added mTOR kinase to 1× kinase buffer to provide 4× kinase solution with a final concentration of 2.5 nM);
③ 2× substrate solution (added the substrates of 4EBP1 and ATP into 1× kinase buffer to provide 2× substrate solution with 4EBP1 final concentration of 50 nM and ATP final concentration of 10.8 μM);
④ 4× test substance solutions (100× test substance solutions with different concentration gradients were prepared using 100% DMSO, and diluted 25-fold with 1× kinase buffer to give 4× test substance solutions with different concentration gradients)
⑤ preparation of test solution (test solution containing EDTA and 4EBP1 phosphorylated antibody was prepared using activity test kit with assay buffer, the final concentration of EDTA was 8 mM, and the final concentration of 4EBP1 phosphorylated antibody was 2 nM)
2. 2.5 μL of 4× test solution was added to a 384-well plate in parallel;
3. added 2.54 μL of 4× kinase solution and incubated for 10 min;
4. then added 5 μL of 2× solutions of 4EBP1 and ATP substrates and incubated for 1 h at room temperature;
5. finally, added 10 μL of test solution to quench the reaction, and read after 60 min;
6. $IC_{50}$ value was obtained via curve fitting.

Inhibition rate (%)=(sample value−minimum)/(maximum−minimum)×100

Minimum refers to the readings of control wells without enzyme, maximum refers to the readings of DMSO control wells.

$IC_{50}$ value was obtained via curve fitting using a soft of Graphpad 5.0.

Experimental Results:

TABLE 2

Enzymatic Inhibitory Activity of Some of the Present Compounds in vitro ($IC_{50}$)

| Test Substances | PI3Kα (nM) | mTOR (nM) |
| --- | --- | --- |
| BGT-226 | 41.91 | 1.99 |
| Compound 7 | 29.3 | 38.7 |
| Compound 14 | 3.3 | 8.5 |
| Compound 22 | 10.2 | 17.5 |

TABLE 3

Enzymatic Inhibitory Activity of Some of the Present Compounds in vitro ($IC_{50}$)

| Test Substances | PI3Kα (nM) | mTOR (nM) |
| --- | --- | --- |
| BEZ-235 | 32.5 | 3.23 |
| Compound 2 | 88.4 | 54.3 |
| Compound 3 | 10.43 | 8.86 |
| Compound 6 | 33.8 | 24 |
| Compound 8 | 260.3 | 76.5 |
| Compound 9 | 872.6 | 43.7 |
| Compound 11 | 495.6 | 31.2 |
| Compound 13 | 21 | 30.3 |
| Compound 52 | 154.3 | 66.5 |

Method 2 Binding Assays
Determination of the Inhibitory Activity of PI3K
1. The Final Concentration of the Agents and Preparation of Stock Solutions of the Test Substances 1.1 3×PI3Kα kinase/antibody solution, prepared using kinase buffer containing antibody, with a final concentration of 8.469 nM, 3× substrate 1710 (kinase tracer 1710), with a final concentration of 57.29 nM;

1.2 3×mTOR kinase/antibody solution, prepared using kinase buffer containing antibody, with a final concentration of 24.72 nM, 3× substrate 314 (kinase tracer 314), with a final concentration of 32.50 nM;

1.3 A stock solution of the test substances was prepared with DMSO, the concentration thereof was 10 mM.

2. Experimental Steps 2.1 The stock solution of the test substances was diluted in 3 times of the highest final concentration, and diluted in 4 times with 10 concentration gradients using kinase buffer;

2.2 The gradiently diluted test substance was added to a 384-well plate in an amount of 5 μL well;

2.3 3× the substrate (kinase tracer) solution was added in an amount of 5 μL/well;

2.4 5× kinase/antibody solution was added in an amount of 5 μL well;

2.5 3×PI3Kα kinase solution was incubated for 50 min at room temperature, 3×mTOR kinase solution was incubated for 40 min;

2.6 Envision reading (excitation wavelength: 340 nM, emission wavelength: 615 nM and 665 nM).

3. Data processing

Inhibition rate (%)=(maximum−sample value)/(maximum−minimum)×100

The data was entered into GraphPad Prism 5.0 and plotted to obtain the curve and $IC_{50}$.

Experimental Results

TABLE 4

Enzymatic Inhibitory Activity of Some of the Present Compounds in vitro ($IC_{50}$)

| Test Substances | PI3Kα (nM) | mTOR (nM) |
|---|---|---|
| Hydrochloride of Compound 58 | 8.6 | 91.94 |
| Compound 86 | 9.7 | 257.2 |
| Compound 114 | 115.0 | 732.3 |

In the present invention, when $IC_{50}$ is 0~300 nM, the test substances are regarded as having a very good kinase inhibitory activity, when $IC_{50}$ is 0.3-3 μM, the test substances are regarded as having a good kinase inhibitory activity, when $IC_{50}$ is higher than 3 μM, the test substances are regarded as not having kinase inhibitory activity.

Experimental Conclusions

It can be seen from Tables 2 to 4 that the present compounds have good enzymatic activity in vitro.

Experimental Example 2

The Cytological Activity Measurement Experiment of the Present Compounds

Tested compounds: the present compounds, made by the applicant, see Preparative Examples for the chemical names and structures of each compound;

Control: paclitaxel, purchased from Sigma Reagent Company, 98% purity.

Experimental Methods
1. Preparation of Reagents and Compounds
1) Preparation of phosphate buffer (PBS):

8 g NaCl, 0.2 g KCl, 1.44 g $Na_2HPO_4$ and 0.24 g $KH_2PO_4$ were weighed, added 800 mL of ultrapure water, adjusted to pH=7.4, further added ultrapure water volume to 1 L, sterilized at high pressure for 20 min.

2) Preparation of XTT test working solution:

100 mg of tetrazolium salt (XTT) powder was weighed and dissolved in dark in 300 mL of phenol red-free serum-free RPMI1640 medium heated to 50° C., filtered and subpackaged, used immediately or within a week. All process should be conducted in dark.

3) Preparation of test compounds preparation of stock solutions of the test substances: the powder of test substances was dissolved in DMSO in a concentration of 10 mM.

preparation of gradiently diluted stock solutions of test substances: First, 10 mM of the stock solutions of test substances were diluted serially in 4-fold with DMSO to 10 concentrations. 2 μL of DMSO-diluted solution for each compound was taken and added to 998 μL of culture medium containing 10% fetal bovine serum (FBS). The highest concentration of the test substances was 20 μM, the concentration of DMSO was 0.2%, and there were 10 concentration gradients in total.

4) Preparation of positive compound preparation of stock solution of paclitaxel: the powder of paclitaxel was dissolved in DMSO in a concentration of 10 mM.

preparation of gradiently diluted stock solutions of paclitaxel: First, 10 mM of paclitaxel was diluted serially to 10 concentrations. 2 μL of DMSO-diluted solution of paclitaxel was taken and added to 998 μL of culture medium containing 10% fetal bovine serum. The concentration of DMSO was 0.2%, and there were 10 concentration gradients in total.

2. Cell Culture

1) Cell Recovery:

Freezing tube was taken out from liquid nitrogen and placed in a water bath at 37° C.~39° C., rapidly melted.

The frozen solution was transferred to a 15 mL sterile centrifuge tube, added 10 times the volume of culture medium and centrifuged at 1000 rpm, 4° C. for 5 min. Discarded the culture medium from the centrifuge tube, and added culture medium containing 10% FBS to resuspend the cells, and then transferred to a culture flask. The medium was changed on the next day.

2) Cell Passage

Cells in logarithmic growth phase were taken, and the culture medium was discarded, added an appropriate volume of PBS to wash once, then add an appropriate volume of digestive fluid containing 0.25% trypsinase and 0.02% EDTA, placed at 37° C. for 2~5 min, discarded the digestive fluid, washed once with PBS. Added an appropriate volume of culture medium containing 10% FBS to terminate digestion, gently pipetted the cells with a pipette, digested the cells to provide a cell suspension for passage and experiment.

3) Cell Cryopreserving

Cells in logarithmic growth phase were taken and digested with a digestive fluid containing 0.25% trypsinase and 0.02% EDTA to provide a cell suspension, centrifuged at 1000 rpm, 4° C. for 5 min. Discarded the culture medium, added frozen medium containing 10% DMSO and 90% FBS to resuspend the cells, subpackaged into freezing tubes in an amount of $2×10^6$ cells per tube. The freezing tubes were put in a process cooling box and kept at −80° C. for 24 h, then transferred to liquid nitrogen for cryopreservation.

3. Cell Plating
1) Preparation of cell suspension

The culture medium was discarded from the flask, and the cells were washed twice with PBS. Added trypsinase to digest the cell and then collected by centrifugation, resuspended with a medium containing 10% FBS, counted and adjusted to an appropriate concentration (cell viability must be greater than 90%). The cell concentration was $5 \times 10^4$ mL.

2) The cell suspension was added to 96-well plates, each well 100 μL.

3) Incubated in a cell incubator overnight at 37° C., 5% $CO_2$.

4. Drug Treatment

Added compound diluted 2-fold to the cell culture plates, three repeated in total, 100 μL well. The final volume was 200 μL, and the initial concentration was 10 μM, 4-fold dilution, 10 concentration gradients in total, wherein the concentration of BEZ-235 started from 1 μM, 3-fold dilution, 10 concentration gradients in total;

5. Cell Viability Assay by XTT Method

Discarded the culture medium, added XTT test working liquid in an amount of 150 μL well, and kept in a cell incubator at 37° C., 5% $CO_2$ for 2 h, then placed into a microplate reader and read the absorbance at 450 nm.

6. Data Processing

1) The percentage of inhibition was calculated using the following formula:

Inhibition rate (%)=(reading(solvent)−reading(compound))/reading(solvent)−reading(positive control))×100

2) The data was entered into GraphPad Prism 5.0 and plotted to obtain the curve and $IC_{50}$.

Experimental Results

Test Substances:

Control substances: BGT-226 and BEZ-235, dissolved in sterile water for injection;

The present compounds, prepared by the applicant, dissolved in sterile water for injection.

Experimental Methods:
Administration

The test substances were administrated via intravenous bolus injection (IV), dose: 2 mg/kg, administrating volume: 2 mL/kg;

The test substances were administrated via gavage (PO), dose: 4 mg/kg, administrating volume: 4 mL/kg.

Blood Sampling Time Point:

0 h before administration, 0.083 h, 0.25 h, 0.5 h, 1 h, 2 h, 4 h, 6 h, 8 h, and 24 h after administration. About 100 μl of whole blood was taken at each time point, centrifugated at 8,000 rpm in a high-speed centrifuge for 6 minutes to separate plasma, and the resulting plasma was frozen at −80° C. in a refrigerator.

Plasma Samples Analysis:

The samples of BGT-226, hydrochloride of Compound 58 and Compound 86 were treated as follows: 20 μl of plasma was taken and added 80 μl of internal standard solution (KBP-2906), subjected to vortex at 1,500 rev/min for 3 minutes, then to centrifugation at 12,000 rpm/min for 5 minutes. 60 μl of supernatant was taken and added with 100 4 of water, then homogenized by vortex and analyzed using LC-MS/MS.

The samples of other compounds were treated as follows: 20 μl of plasma was taken and added 800 μl of internal standard solution (KBP-3957), subjected to vortex at 1,500 rev/min for 10 minutes, then to centrifugation at 12,000 rpm/min for 5 minutes. 400 μl of supernatant was taken and blown to dry under nitrogen, re-dissolved in 200 μL of a mixture of methanol:water (1:1, V/V) and analyzed using LC-MS/MS.

TABLE 5

Cytologic Activity of Some of the Present Compounds in vitro ($IC_{50}$)

| Test substances | U87MG (nM) | SKOV-3 (nM) |
|---|---|---|
| Compound 3 | 84.7 | 155 |
| Compound 7 | 900.9 | 895 |
| Compound 14 | 436.7 | 890.3 |
| Compound 22 | 275.1 | 551.2 |
| Compound 30 | 499.2 | 348.9 |
| Compound 52 | 436.2 | 466.7 |
| Compound 80 | 278.9 | 542.4 |

In the present invention, when $IC_{50}$ is 0~300 nM, the test substances are regarded as having a very good inhibitory activity to cell, when $IC_{50}$ is 0.3-3 μM, the test substances are regarded as having a good inhibitory activity to cell, and when $IC_{50}$ is higher than 3 μM, the test substances are regarded as not having inhibitory activity to cell.

Experimental Conclusions

It can be seen from Table 5 that the present compounds have good cytological activity in vitro, and can inhibit the proliferation of tumor cells.

Experimental Example 3

In Vivo Pharmacokinetics Experiment of the Present Compounds in Rats

Test animals: male SD rats, weighing 230-250 g. Three rats were tested for each administration route of each compound.

TABLE 6

The evaluation results of pharmacokinetics of the present compounds in rats (IV)

| Test Substances | T½ (h) | AUC (h*ng/ml) | Cl_obs (L/h/kg) | Vss_obs (L/kg) |
|---|---|---|---|---|
| BGT-226 | 4.8 | 1520 | 1.3 | 8.72 |
| BEZ-235 | 3.19 | 1439 | 1.38 | 5.93 |
| Compound 3 | 6.48 | 1702.69 | 1.14 | 5.6 |
| Compound 7 | 0.47 | 274.63 | 7.42 | 4.45 |
| Compound 14 | 2.08 | 735.30 | 2.84 | 2.97 |
| Compound 22 | 0.72 | 356.89 | 5.57 | 5.28 |
| Hydrochloride of Compound 58 | 3.47 | 217.7 | 7.39 | 36.26 |
| Compound 86 | 0.2 | 153.9 | 13.6 | 3.58 |

TABLE 7

The evaluation results of pharmacokinetics of the present compounds (PO) in rats

| Test Substances | T½ (h) | AUC (h*ng/ml) | Cmax (ng/ml) | Tmax (h) | F % |
|---|---|---|---|---|---|
| BGT-226 | — | 852 | 61.1 | 6 | 28 |
| BEZ-235 | 4.08 | 2175.69 | 229.33 | 2.83 | 77.44 |
| Compound 3 | 5.33 | 1376.23 | 197.63 | 0.5 | 40.4 |
| Compound 7 | 1.7 | 63.44 | 34.94 | 0.5 | 11.55 |
| Compound 14 | 1.39 | 402.00 | 147.30 | 0.5 | 26.26 |
| Hydrochloride of Compound 58 | — | 258 | 46.8 | 4.67 | 59 |
| Compound 86 | 1.04 | 177 | 250.67 | 0.33 | 58 |

Experimental Conclusions

It can be seen from Tables 6 and 7 that the present compounds have good pharmacokinetic properties and good bioavailability.

Experimental Example 4

The Repeated-Dose Toxicity Test of the Present Compounds in Rats

Tested Substances:
the present compound of No. 3, made by the applicant, see Preparative Example for the chemical name and structure thereof;
control drug: BEZ-235, prepared according to the method described in WO2006122806.

The test substances were suspended in 0.5% methylcellulose solution to prepare suspensions with a concentration of 0.5 mg/mL, 1.5 mg/mL and 3 mg/mL.

Animals: SD rats, 6-8 weeks old, SPF grade, purchased from Beijing Vital River Laboratory Animal Technology Co., Ltd., licensed cell No: SCXK (Beijing) 2006-0009.

Experimental Methods

Selected 140 SD rats which meet the test requirements, half male and half female, 20 rats/group, divided into seven dose groups including Compound 3 low, medium and high dose groups, BEZ-235 low, medium and high dose groups and solvent control group. The test substances were administrated as a suspension via gavage, and administrating volume was 10 mL/kg. 0.5% methyl cellulose solution was used in the solvent group, and the administrating volume was 10 mL/kg, administered once daily for consecutive 14 days. Animals were observed daily appearance and general behavior changes.

Experimental Results

TABLE 8

The observation results of vital signs in the repeated-dose toxicity test of the present compounds in rats

| Test Substances | dose (mg/kg/day) | animal numbers | loose stools | lassitude | hair loss |
|---|---|---|---|---|---|
| Compound 3 low-dose group | 5 | 20 | 0/20 | 0/20 | 0/20 |
| Compound 3 middle-dose group | 15 | 20 | 1/20 | 0/20 | 0/20 |
| Compound 3 high-dose group | 30 | 20 | 1/20 | 4/20 | 1/20 |
| BEZ-235 low-dose group | 5 | 20 | 6/20 | 0/20 | 0/20 |
| BEZ-235 middle-dose group | 15 | 20 | 7/20 | 0/20 | 0/20 |
| BEZ-235 high-dose group | 30 | 20 | 15/20 | 0/20 | 3/20 |
| Solvent control group | — | 20 | 0/20 | 0/20 | 0/20 |

It can be seen from Table 8 that, at the low doses, there was no animals with abnormal vital signs in the group of Compound 3, whereas there were six rats with loose stools in BEZ-235 group; at the middle doses, there was one rat with loose stools in the group of Compound 3, whereas there were seven rats with loose stools in BEZ-235 group; at high doses, there were one rat with loose stools, four rats with lassitude and one rat with hair loss in the group of Compound 3, whereas there were fifteen rats with loose stools and three rats with hair loss in BEZ-235 group. Therefore, the present compounds have lower toxicity and are safer than BEZ-235.

Preparative Examples

The above contents of the present invention will be described in further detail by the following Examples, but this should not be construed that the invention is limited to the following Examples.

The abbreviations in the following Examples are defined as follows:
DCM: dichloromethane
Pd(PPh$_3$)$_4$: tetrakis(triphenylphosphine)palladium
DMAP: 4-dimethylaminopyridine
C$_3$Cl$_6$O$_3$: triphosgene
Ac$_2$O: acetic anhydride
TEA: triethylamine Preparation of ethyl 4,6-dichloro-1,5-naphthyridine-3-carboxylate (material)

The above compound was prepared according to the method disclosed in WO2010038165 A1, and the preparation procedures are as follows:

1. Preparation of 6-bromopyridin-3-amine

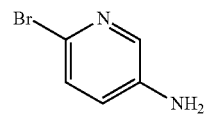

Iron powder (88 g, 1.571 mmol), concentrated hydrochloric acid (61 mL) and water (287 mL) were sequentially added to a solution of 2-bromo-5-nitropyridine (64 g, 0.317 mol) in ethanol (1 L). The mixture was reacted under reflux for 5 h. The reaction mixture was cooled, filtered and the filtrate was concentrated and then adjusted to approximately pH 7-8 with a saturated aqueous solution of sodium bicarbonate, filtered again, and the filtrate was extracted with 200 mL of dichloromethane. The organic phase was dried over anhydrous sodium sulfate, concentrated under reduced pressure to give 40.5 g of a pale yellow solid.

2. Preparation of diethyl 2-(((6-bromopyridin-3-yl)amino)methylene)malonate

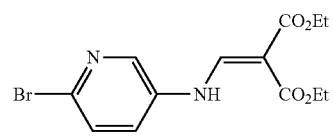 [SMILES: CCOC(=O)C(=CNc1ccc(Br)nc1)C(=O)OCC]

6-bromopyridin-3-amine (74 g, 0.43 mol) and diethyl ethoxymethylenemalonate (100 mL) were added to 680 mL of ethanol and heated under reflux for 5 h. The reaction mixture was cooled to precipitate a solid, suction filtered, and

3. Preparation of ethyl 6-bromo-4-hydroxy-1,5-naphthyridine-3-carboxylate

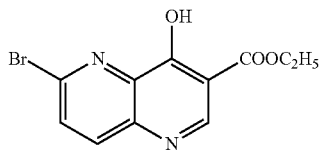

Diethyl(2-(((6-bromopyridin-3-yl)amino)methylene)malonate (40 g, 0.117 mol) was added to boiling diphenyl ether (214 mL) in batches over 5 min, heated under reflux for 45 min. After confirming a disappearance of the raw materials by a thin layer chromatography plate (ethyl acetate:petroleum ether=1:3), the reaction mixture was cooled and poured into petroleum ether to precipitate a solid, suction filtered to give 24.6 g of a khaki solid.

4. Preparation of ethyl 4,6-dichloro-1,5-naphthyridine-3-carboxylate

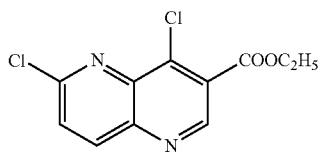

Ethyl 6-bromo-4-hydroxy-1,5-naphthyridine-3-carboxylate (49.8 g, 0.168 mmol) and N,N-dimethylaniline (8 mL) were added to phosphorus oxychloride (400 mL), and heated under reflux for 3 h. The reaction mixture was cooled, phosphorus oxychloride was distilled off under reduced pressure, and the resulting residue was poured into ice water, and adjusted approximately to pH 8 with a saturated aqueous solution of sodium bicarbonate, then extracted with 200 mL of dichloromethane. The organic phase was dried over anhydrous sodium sulfate, concentrated and subjected to silica gel column chromatography (petroleum ether:ethyl acetate=3:1) to give 20.2 g of a pale yellow solid.

Example 1

Preparation of 9-(6-aminopyridin-3-yl)-3-methyl-1-(3-(trifluoromethyl)phenyl)-3,4-dihydropyrimido[5,4-c][1,5]naphthyridin-1(2H)-one

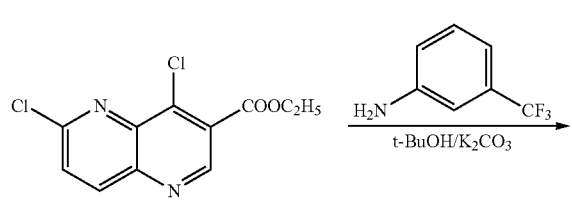

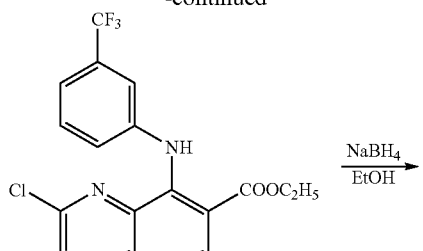

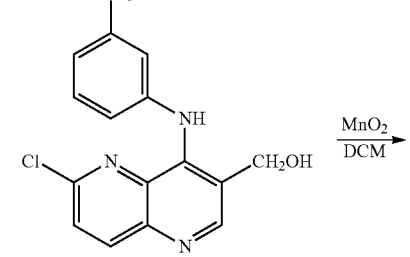

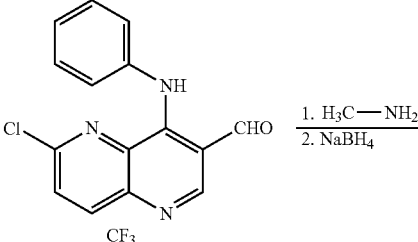

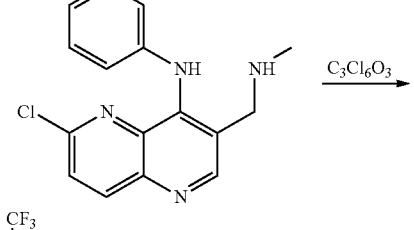

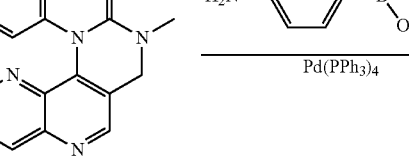

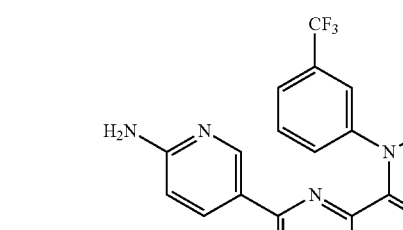

(1) Preparation of ethyl 6-chloro-4-((3-(trifluoromethyl)phenyl)amino-1,5-naphthyridine-3-carboxylate

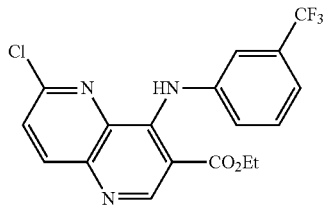 [SMILES: CCOC(=O)c1cnc2ccc(Cl)nc2c1Nc1cccc(C(F)(F)F)c1]

Ethyl 4,6-dichloro-1,5-naphthyridine-3-carboxylate (2.70 g, 10.0 mmol) and 3-(trifluoromethyl)aniline (1.77 g, 11.0 mmol) were dissolved in tert-butanol (50 mL), and to the system added potassium carbonate (4.15 g, 30.0 mmol). The reaction mixture was stirred under reflux for 3 hours. After confirming a disappearance of the raw materials by a thin layer chromatography plate (ethyl acetate:petroleum ether=1:3), the reaction mixture was suction filtered, the solid was washed with 30 mL of dichloromethane, and the resulting wash solution and the filtrate were combined, concentrated under reduced pressure, and the resulting residue was recrystallized from diethyl ether to give 3.7 g of a pale yellow solid.

(2) Preparation of 6-chloro-4-((3-(trifluoromethyl)phenyl)amino)-1,5-naphthyridine-3-carbaldehyde

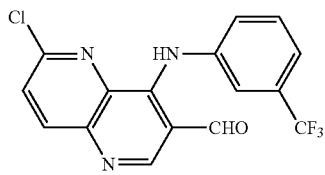 [SMILES: O=Cc1cnc2ccc(Cl)nc2c1Nc1cccc(C(F)(F)F)c1]

Ethyl 6-chloro-4-((3-(trifluoromethyl)phenyl)amino)-1,5-naphthyridine-3-carboxylate (2.5 g, 6.3 mmol) was added to ethanol (80 mL), and to the system added sodium borohydride (0.95 g, 25.1 mmol) in batches, stirred at room temperature for 24 h, ethanol was removed under reduced pressure, added 20 mL of water, and extracted with 150 mL of dichloromethane. The organic layer was dried over anhydrous sodium sulfate, concentrated under reduced pressure. The resulting 1.3 g of the crude product was dissolved in dichloromethane (20 mL), to the solution added manganese dioxide (9.6 g, 110.5 mmol) in batches. The reaction mixture was stirred at room temperature for 8 h. Filtered and the filter cake was washed with 50 mL of dichloromethane, and the resulting wash solution and the filtrate were combined and concentrated. The resulting solid was subjected to silica gel column chromatography (ethyl acetate:petroleum ether=2:1) to give 1.1 g of the product.

(3) Preparation of 6-chloro-3-((methylamino)methyl)-N-(3-(trifluoromethyl)phenyl)-1,5-naphthyridin-4-amine

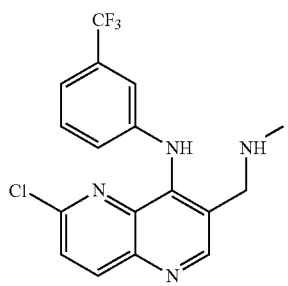 [SMILES: CNCc1cnc2ccc(Cl)nc2c1Nc1cccc(C(F)(F)F)c1]

6-chloro-4-((3-(trifluoromethyl)phenyl)amino)-1,5-naphthyridine-3-carbaldehyde (0.75 g, 2.13 mmol) was dissolved in ethanol (20 mL), added 1.2 mL of a solution of methylamine in ethanol (concentration 27%), stirred at room temperature for 4 h, and then added sodium borohydride (0.82 g, 21.7 mmol) to the system, continued stirring at room temperature for 18 h. The reaction was quenched with a saturated aqueous solution of sodium carbonate, concentrated under reduced pressure to remove ethanol, extracted with 80 mL of dichloromethane, the organic layer was dried over anhydrous sodium sulfate, concentrated under reduced pressure to obtain 0.77 g of the titled compound.

(4) Preparation of 9-chloro-3-methyl-1-(3-(trifluoromethyl)phenyl)-3,4-dihydropyrimido[5,4-c][1,5]naphthyridin-1(2H)-one

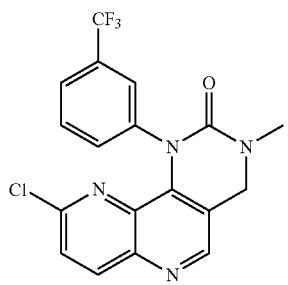 [SMILES: CN1Cc2cnc3ccc(Cl)nc3c2N(c2cccc(C(F)(F)F)c2)C1=O]

6-chloro-3-((methylamino)methyl)-N-(3-(trifluoromethyl)phenyl)-1,5-naphthyridin-4-amine (0.77 g, 2.10 mmol) was dissolved in dichloromethane (20 mL), to the reaction flask in an ice bath added triphosgene (0.68 g, 2.29 mmol) and triethylamine (0.8 mL), then stirred at room temperature for 2 h. The reaction was quenched with a saturated aqueous solution of sodium carbonate, extracted with 80 mL of dichloromethane, the organic layer was dried over anhydrous sodium sulfate, concentrated under reduced pressure to remove the solvent to give 0.82 g of the titled compound.

(5) Preparation of 9-(6-aminopyridin-3-yl)-3-methyl-1-(3-(trifluoromethyl)phenyl)-3,4-dihydropyrimido[5,4-c][1,5]naphthyridin-1(2H)-one

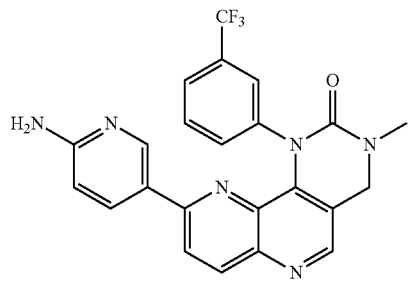 [SMILES: CN1Cc2cnc3ccc(-c4ccc(N)nc4)nc3c2N(c2cccc(C(F)(F)F)c2)C1=O]

9-chloro-3-methyl-1-(3-(trifluoromethyl)phenyl)-3,4-dihydropyrimido[5,4-c][1,5]naphthyridin-1(2H)-one (0.82 g, 2.09 mmol) obtained in the above step and 6-amino-3-pyridine boronic acid (462 mg, 2.10 mmol) were dissolved in toluene (15 mL) and ethanol (5 mL), to the system added tetrakis(triphenylphosphine) palladium (12 mg) and 2N aqueous sodium carbonate solution (3.2 mL). Refluxed and reacted under nitrogen for 6 h, cooled to room temperature, filtered and the filtrate was concentrated under reduced pressure and dissolved in 30 mL of dichloromethane, washed sequentially with water and saturated brine, dried over anhydrous sodium sulfate, concentrated and subjected to silica gel column chromatography (ethyl acetate:petroleum ether=1:1) to give 373 mg of the product.

Molecular formula: $C_{23}H_{17}F_3N_6O$; Molecular weight: 450.14; Mass spectrum (M+H): 450.9

$^1$H-NMR (d$_6$-DMSO, 400 MHz): δ 8.71 (1H, s), 8.30-8.16 (2H, m), 8.10 (1H, t), 7.86 (1H, s), 7.62 (1H, d), 7.55-7.42 (2H, m), 6.92 (1H, dd), 6.45 (2H, s), 6.26 (1H, d), 4.75 (2H, s), 3.00 (3H, s)

Example 2

Preparation of N-(5-(3-methyl-2-oxo-1-(3-(trifluoromethyl)phenyl)-1,2,3,4-tetrahydropyrimido[5,4-c][1,5]naphthyridin-9-yl)pyridin-2-yl)acetamide (Compound 7)

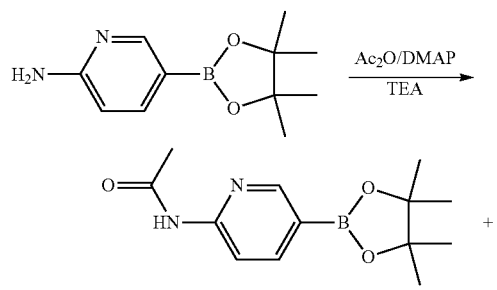

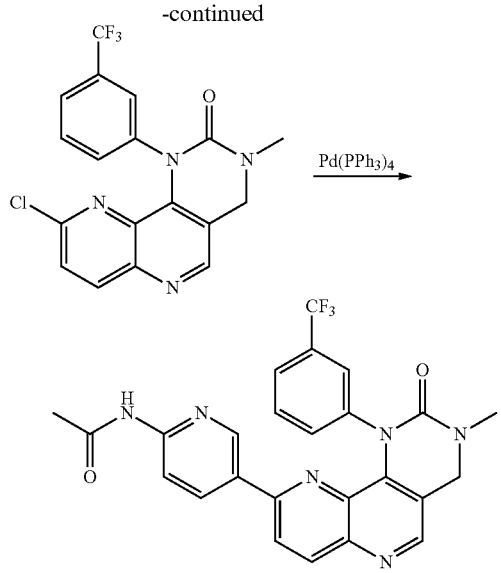

(1) Preparation of N-(5-(4,4,5,5-tetramethyl-1,3,2-dioxaborolan-2-yl)pyridin-2-yl)acetamide

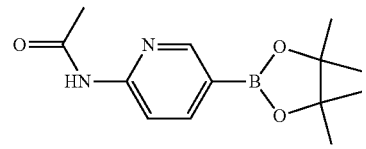 [SMILES: CC(=O)Nc1ccc(B2OC(C)(C)C(C)(C)O2)cn1]

4-dimethylaminopyridine (17 mg, 0.139 mmol), triethylamine (0.19 mL, 1.36 mmol) and acetic anhydride (153 mg, 1.50 mmol) were added sequentially to a solution of 5-(4,4,5,5-tetramethyl-1,3,2-dioxaborolan-2-yl)pyridin-2-amine (300 mg, 1.36 mmol) in dichloromethane (15 mL). The reaction mixture was stirred at room temperature for 0.5 h, then diluted with 30 mL of dichloromethane, washed with 50 mL of a saturated aqueous solution of ammonium chloride. The organic phase was dried over anhydrous magnesium sulfate, filtered and concentrated to give 225 mg of the product.

(2) Preparation of N-(5-(3-methyl-2-oxo-1-(3-(trifluoromethyl)phenyl)-1,2,3,4-tetrahydropyrimido[5,4-c][1,5]naphthyridin-9-yl)pyridin-2-yl)acetamide

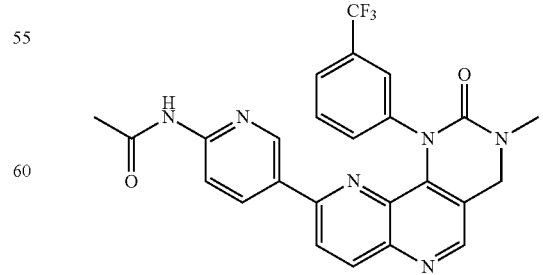

9-chloro-3-methyl-1-(3-(trifluoromethyl)phenyl)-3,4-dihydropyrimido[5,4-c][1,5]naphthyridin-2(1H)-one (314 mg, 0.80 mmol), tetrakis(triphenylphosphine) palladium (15 mg, 0.013 mmol) and 2N aqueous sodium carbonate solution (1.3 mL) were added sequentially to a solution of N-(5-(4,4,5,5-tetramethyl-1,3,2-dioxaborolan-2-yl)pyridin-2-yl)acetamide (225 mg, 0.858 mmol) in 1,4-dioxane (15 mL), and reacted under nitrogen at 90° C. for 16 h, cooled to room temperature, filtered, the organic layer was concentrated under reduced pressure, dissolved in 50 mL of dichloromethane, washed sequentially with water and saturated brine, dried over anhydrous sodium sulfate, concentrated and subjected to silica gel column chromatography (ethyl acetate) to give 267 mg of the product.

Molecular formula: $C_{25}H_{19}F_3N_6O_2$; Molecular weight: 492.1; Mass spectrum (M+H): 493.2

$^1$H-NMR ($d_6$-DMSO, 400 MHz): δ 10.64 (1H, s), 8.81 (1H, s), 8.41 (1H, d), 8.37 (1H, d), 8.25 (1H, d), 7.98 (1H, d), 7.82 (1H, s), 7.67-7.62 (1H, m), 7.61-7.52 (2H, m), 7.37 (1H, dd), 4.79 (2H, s), 3.01 (3H, s), 2.10 (3H, s)

Example 3

Preparation of 9-(2-aminopyrimidin-5-yl)-3-methyl-1-(3-(trifluoromethyl)phenyl)-3,4-dihydropyrimido[5,4-c][1,5]naphthyridin-1(2H)-one (Compound 14)

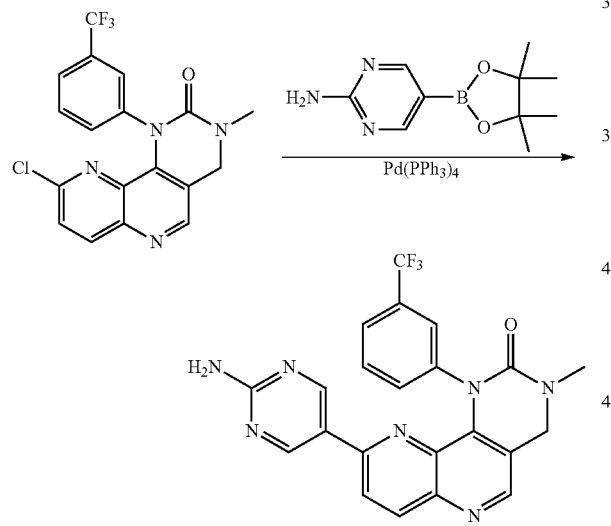

9-chloro-3-methyl-1-(3-(trifluoromethyl)phenyl)-3,4-dihydropyrimido[5,4-c][1,5]naphthyridin-1(2H)-one (315 mg, 0.802 mmol) and 5-(4,4,5,5-tetramethyl-1,3,2-dioxaborolan-2-yl)pyrimidin-2-amine (195 mg, 0.882 mmol) were dissolved in 1,5-dioxane (15 mL), to the system added tetrakis(triphenylphosphine) palladium (12 mg) and 2N aqueous sodium carbonate solution (1.4 mL). Refluxed and reacted under nitrogen for 16 h, cooled to room temperature, filtered, and the organic layer was concentrated under reduced pressure, dissolved in 50 mL of dichloromethane, washed sequentially with water and saturated brine, dried over anhydrous sodium sulfate, concentrated and subjected to silica gel column chromatography (ethyl acetate:petroleum ether=1:1) to give 185 mg of the product.

Molecular formula: $C_{22}H_{16}F_3N_7O$; Molecular weight: 451.1; Mass spectrum (M+H): 452.2

$^1$H-NMR ($d_6$-DMSO, 400 MHz): δ 8.74 (1H, s), 8.28 (1H, d), 8.12-8.07 (3H, m), 7.70 (1H, s), 7.67-7.54 (3H, m), 7.06 (2H, s), 4.76 (2H, s), 3.00 (3H, s)

Example 4

3-methyl-9-(1H-pyrrolo[2,3-b]pyridin-5-yl)-1-(3-(trifluoromethyl)phenyl)-3,4-dihydropyrimido[5,4-c][1,5]naphthyridin-1(2H)-one (Compound 22)

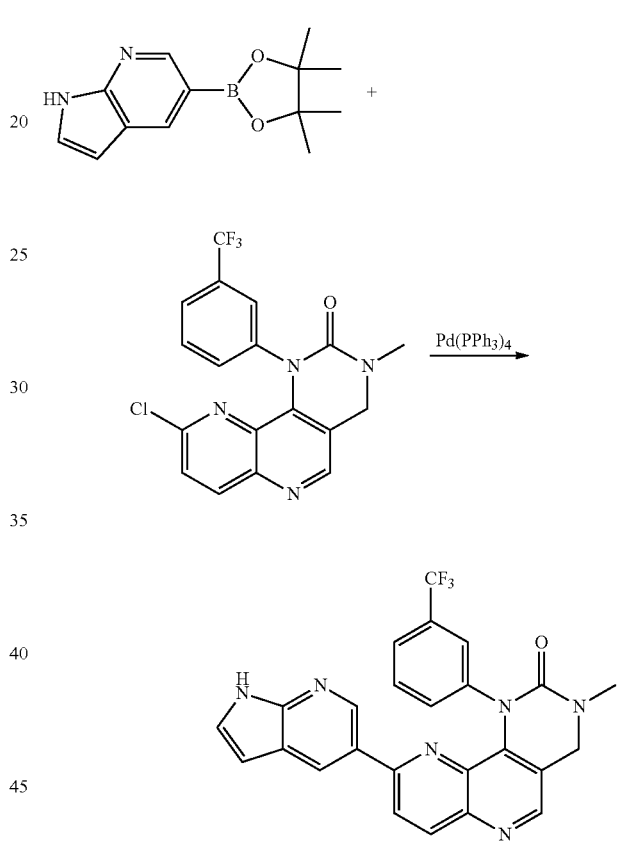

9-chloro-3-methyl-1-(3-(trifluoromethyl)phenyl)-3,4-dihydropyrimido[5,4-c][1,5]naphthyridin-1(2H)-one (326 mg, 0.83 mmol) and 5-(4,4,5,5-tetramethyl-1,3,2-dioxaborolan-2-yl)-1H-pyrrolo[2,3-b]pyridine (244 mg, 1.0 mmol) were dissolved in 1,4-dioxane (12 mL), to the system added tetrakis(triphenylphosphine) palladium (12 mg, 0.0104 mmol) and 2N aqueous sodium carbonate solution (0.6 mL). Refluxed and reacted under nitrogen for 16 h, cooled to room temperature, filtered, and the organic layer was concentrated under reduced pressure, dissolved in 50 mL of dichloromethane, washed sequentially with water and saturated brine, and the organic layer was dried over anhydrous sodium sulfate, concentrated and subjected to silica column chromatography (ethyl acetate) to give 243 mg of the product.

Molecular formula: $C_{25}H_{17}F_3N_6O$; Molecular weight: 474.14; Mass spectrum (M+H): 475.2

$^1$H-NMR (d$_6$-DMSO, 400 MHz): δ 11.78 (1H, s), 8.77 (1H, s), 8.34 (1H, d), 8.30 (1H, d), 8.27 (1H, d), 7.83 (1H, s), 7.75-7.69 (1H, m), 7.63-7.58 (3H, m), 7.50 (1H, t), 6.46 (1H, dd), 4.78 (2H, s), 3.01 (3H, s)

Example 5

Preparation of 2-(4-(9-(6-methoxypyridin-3-yl)-3-methyl-2-oxo-3,4-dihydropyrimido[5,4-c][1,5]naphthyridin-1(2H)-yl)phenyl)-2-methylpropionitrile (Compound 30)

(1) Preparation of ethyl 6-chloro-4-((4-(2-cyanopropan-2-yl)phenyl)amino)-1,5-naphthyridine-3-carboxylate

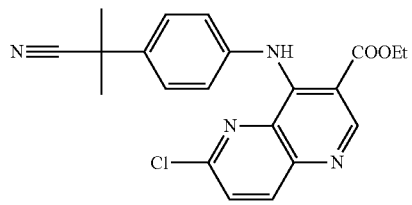 [SMILES: CCOC(=O)c1cnc2ccc(Cl)nc2c1Nc1ccc(C(C)(C)C#N)cc1]

Ethyl 4,6-dichloro-1,5-naphthyridine-3-carboxylate (6.4 g, 23.6 mmol) and 2-(4-aminophenyl)-2-methylpropionitrile (5.6 g, 35 mmol) were dissolved in tert-butanol (200 mL), to the system added potassium carbonate (16.4 g, 119 mmol), and the reaction mixture was stirred under reflux for 2 h. After confirming a disappearance of the raw materials by a thin layer chromatography plate (ethyl acetate:petroleum ether=1:3), the reaction mixture was suction filtered, the filtrate was concentrated under reduced pressure, and the resulting residue was washed with diethyl ether to give 8.1 g of a pale yellow solid.

(2) Preparation of 2-(4-((6-chloro-3-(hydroxymethyl)-1,5-naphthyridin-4-yl)amino)phenyl)-2-methylpropionitrile

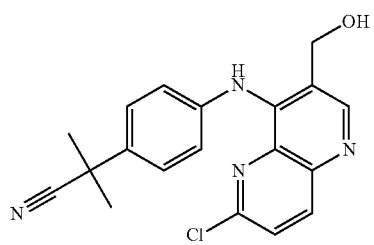 [SMILES: CC(C)(C#N)c1ccc(Nc2c(CO)cnc3ccc(Cl)nc23)cc1]

Ethyl 6-chloro-4-((4-(2-cyanopropan-2-yl)phenyl)amino)-1,5-naphthyridine-3-carboxylate (8.1 g, 20.5 mmol) was added to a mixed solvent of ethanol (120 mL) and dichloromethane (12 mL), to the system added sodium borohydride (5.4 g, 143 mmol) in batches, stirred at room temperature for 24 h, ethanol was removed under reduced pressure, adjusted pH of the solution to be neutral with 1 N dilute hydrochloric acid and extracted with 200 mL of ethyl acetate. The organic layer was dried over anhydrous sodium sulfate, concentrated under reduced pressure, and the resulting 9.0 g of a crude solid was used directly in the next step.

(3) Preparation of 2-(4-((6-chloro-3-formyl-1,5-naphthyridin-4-yl)amino)phenyl)-2-methylpropionitrile

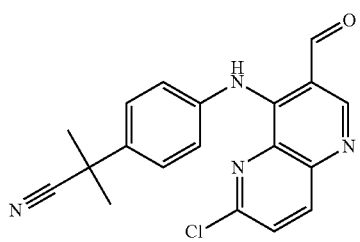 [SMILES: CC(C)(C#N)c1ccc(Nc2c(C=O)cnc3ccc(Cl)nc23)cc1]

9.0 g of the crude product of 2-(4-((6-chloro-3-(hydroxymethyl)-1,5-naphthyridin-4-yl)amino)phenyl)-2-methylpropionitrile obtained in the above step was dissolved in dichloromethane (250 mL), to the solution added manganese dioxide (67 g, 0.77 mol) in batches, and the reaction mixture was stirred at room temperature for 30 h. Filtered, and the filter cake was washed with 50 mL of dichloromethane, The resulting wash solution and the filtrate were combined and concentrated under reduced pressure to give a solid. The resulting solid was subjected to silica gel column chromatography (ethyl acetate:petroleum ether=2:1) to give 2.5 g of the product.

(4) Preparation of 2-(4-((6-chloro-3-((methylamino)methyl)-1,5-naphthyridin-4-yl)amino)phenyl)-2-methylpropionitrile

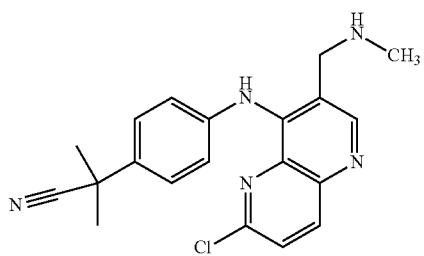 [SMILES: CNCc1cnc2ccc(Cl)nc2c1Nc1ccc(C(C)(C)C#N)cc1]

2-(4-((6-chloro-3-formyl-1,5-naphthyridin-4-yl)amino)phenyl)-2-methylpropionitrile (2.5 g, 7.1 mmol) was dissolved in ethanol (100 mL), added 3 mL of a solution of methylamine in ethanol (concentration 27%), stirred at room temperature for 10 h. Then, to the system added sodium borohydride (1.5 g, 3.97 mol), continued stirring at room temperature for 18 h, and the reaction was quenched with a saturated aqueous solution of sodium carbonate. Concentrated under reduced pressure to remove ethanol, extracted with 150 mL of dichloromethane, the organic layer was dried (5) Preparation of 2-(4-(9-chloro-3-methyl-2-oxo-3, 4-dihydropyrimido[5,4-c][1,5]naphthyridin-1(2H)-yl)phenyl)-2-methylpropionitrile

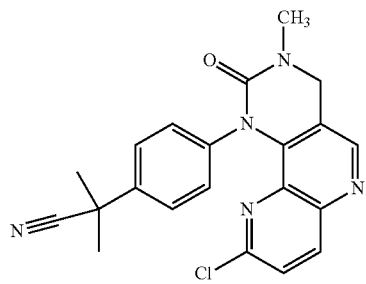 [SMILES: CN1Cc2cnc3ccc(Cl)nc3c2N(c2ccc(C(C)(C)C#N)cc2)C1=O]

2-(4-((6-chloro-3-((methylamino)methyl)-1,5-naphthyridin-4-yl)amino)phenyl)-2-methylpropionitrile (2.0 g, 5.5 mmol) was dissolved in dichloromethane (25 mL), to the reaction flask in an ice bath added triphosgene (1.8 g, 6.1 mmol) and triethylamine (0.7 mL). Then, the mixture was stirred at room temperature for 2 h. The reaction was quenched with a saturated aqueous solution of sodium carbonate, extracted with 100 mL of dichloromethane, the organic layer was dried over anhydrous sodium sulfate, the solvent was removed under reduced pressure to give 1.6 g of a pale yellow solid.

(6) Preparation of 2-(4-(9-(6-methoxypyridin-3-yl)-3-methyl-2-oxo-3,4-dihydropyrimido[5,4-c][1,5]naphthyridin-1(2H)-yl)phenyl)-2-methylpropionitrile

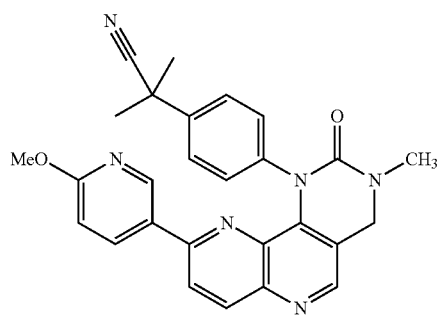 [SMILES: COc1ccc(-c2ccc3ncc4c(c3n2)N(c2ccc(C(C)(C)C#N)cc2)C(=O)N(C)C4)cn1]

2-(4-(9-chloro-3-methyl-2-oxo-3,4-dihydropyrimido[5,4-c][1,5]naphthyridin-1(2H)-yl)phenyl)-2-methylpropionitrile (700 mg, 1.79 mmol) and 6-methoxy-3-pyridine boronic acid (328 mg, 2.15 mmol) were dissolved in toluene (30 mL) and ethanol (10 mL), to the system added tetrakis(triphenylphosphine) palladium (40 mg) and 2N aqueous sodium carbonate solution (2.7 mL). Refluxed and reacted under nitrogen for 3 h, cooled to room temperature, filtered, the organic layer was concentrated under reduced pressure, dissolved in 50 mL of dichloromethane, washed sequentially with water and saturated brine, and the organic layer was dried over anhydrous sodium sulfate, and concentrated. The resulting solid was subjected to silica gel column chromatography (ethyl acetate:petroleum ether=1:1) to give 120 mg of the product.

Molecular formula: $C_{27}H_{24}N_6O_2$; Molecular weight: 464.20; MS (M+H): 465.0

$^1$H-NMR ($d_6$-DMSO, 400 MHz): δ 8.75 (1H, s), 8.32 (1H, d), 8.14 (1H, d), 8.00 (1H, d), 7.68 (1H, dd), 7.53-7.46 (2H, m), 7.41-7.35 (2H, m), 6.75 (1H, d), 4.74 (2H, s), 3.87 (3H, s), 2.99 (3H, s), 1.68 (6H, s)

Example 6

Preparation of 2-methyl-2-(4-(3-methyl-2-oxo-9-(quinolin-3-yl)-3,4-dihydropyrimido[5,4-c]1,5]naphthyridin-1(2H)-yl)phenyl)propionitrile (Compound 52)

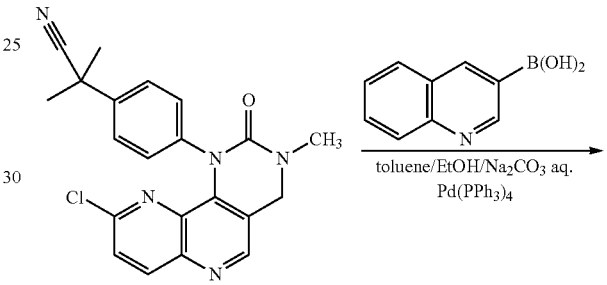

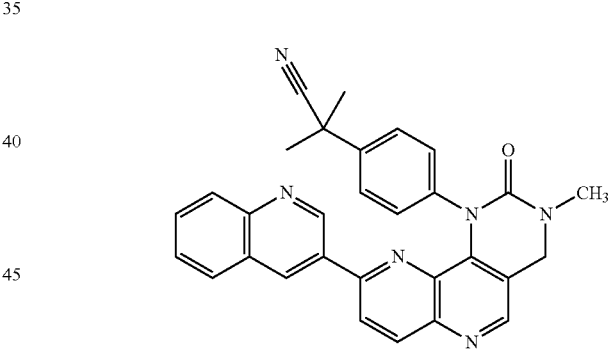

2-(4-(9-chloro-3-methyl-2-oxo-3,4-dihydropyrimido[5,4-c][1,5]naphthyridin-1(2H)-yl)phenyl)-2-methylpropionitrile (700 mg, 1.79 mmol) and quinolin-3-yl boronic acid (372 mg, 2.15 mmol) was dissolved in toluene (30 mL) and ethanol (10 mL), to the system added tetrakis(triphenylphosphine) palladium (70 mg) and 2N aqueous sodium carbonate solution (2.7 mL). Refluxed and reacted under nitrogen for 3 h, cooled to room temperature, filtered, the organic layer was concentrated under reduced pressure, dissolved in 50 mL of dichloromethane, washed sequentially with water and saturated brine, the organic layer was dried over anhydrous sodium sulfate, concentrated and subjected to silica column chromatography (ethyl acetate:petroleum ether=1:1) to give 140 mg of the product.

Molecular formula: $C_{30}H_{24}N_6O$; Molecular weight: 484.20; Mass spectrum (M+H): 485.0

¹H-NMR (d₆-DMSO, 400 MHz): δ 8.82 (1H, s), 8.69 (1H, d), 8.52 (1H, d), 8.47-8.37 (2H, m), 8.03 (1H, d), 7.98 (1H, d), 7.79 (1H, t), 7.64 (1H, t), 7.53-7.42 (4H, m), 4.78 (2H, s), 3.02 (3H, s), 1.54 (6H, s)

Example 7

Preparation of 9-(6-methoxypyridin-3-yl)-3-methyl-1-(4-(piperazin-1-yl)-3-(trifluoromethyl)phenyl)-3,4-dihydropyrimido[5,4-c][1,5]naphthyridin-2(1H)-one hydrochloride (hydrochloride of Compound 58)

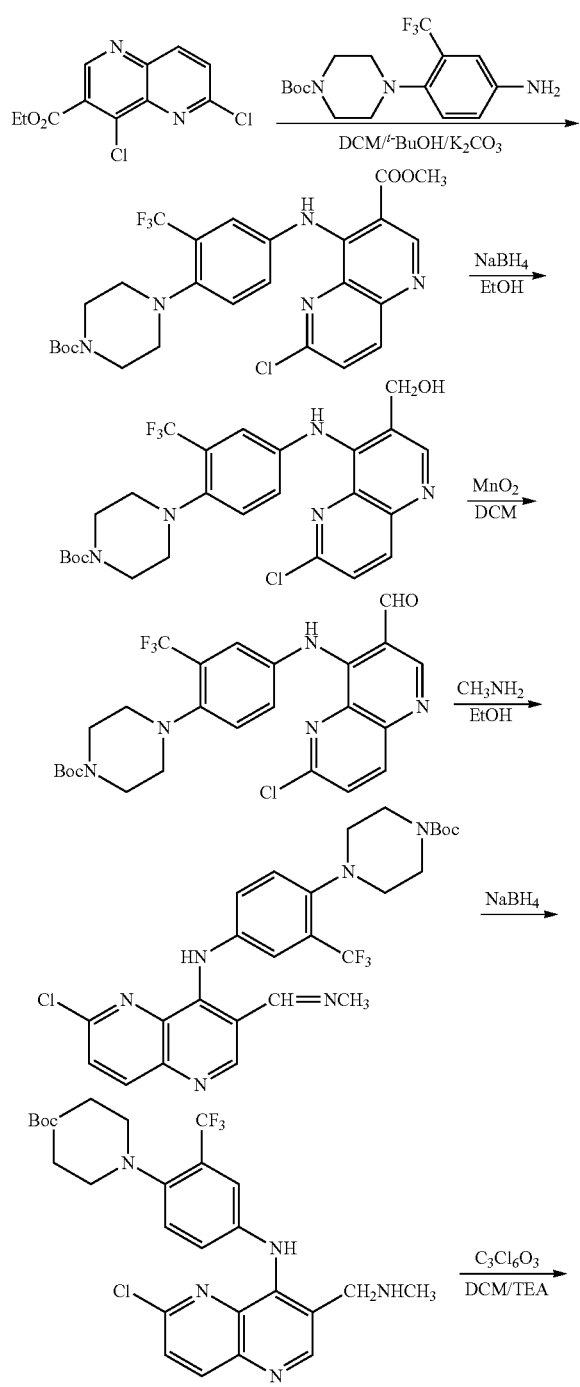

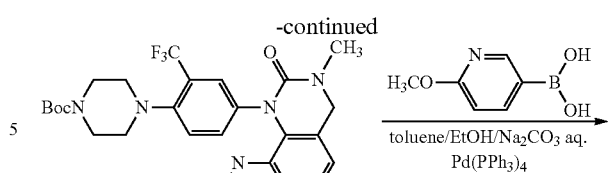

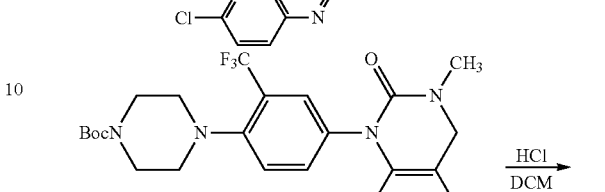

(1) Methyl 4-((4-(4-(tert-butoxycarbonyl)piperazin-1-yl)-3-(trifluoromethyl)phenyl)amino)-6-chloro-1,5-naphthyridine-3-carboxylate

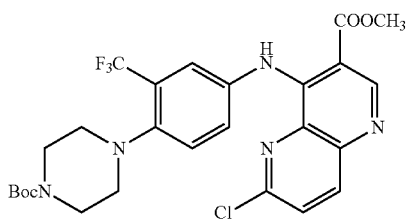 [SMILES: COC(=O)c1cnc2ccc(Cl)nc2c1Nc1ccc(N2CCN(C(=O)OC(C)(C)C)CC2)c(C(F)(F)F)c1]

Ethyl 4,6-dichloro-1,5-naphthyridine-3-carboxylate (0.5 g, 1.84 mmol) and tert-butyl 4-(4-amino-2-(trifluoromethyl)phenyl)piperazine-1-carboxylate (0.766 g, 2.22 mmol) were dissolved in a mixture of dichloromethane (5 mL) and tert-butanol (5 mL), to the system added potassium carbonate (0.612 g, 4.43 mmol). The reaction mixture was stirred at room temperature for 24 h, suction filtered, the solid was washed with 30 mL of dichloromethane, and the resulting wash solution and the filtrate were combined, concentrated under reduced pressure, and the resulting residue was recrystallized from diethyl ether to give 0.73 g of a pale yellow solid.

(2) Preparation of tert-butyl 4-(4-((6-chloro-3-(hydroxymethyl)-1,5-naphthyridin-4-yl)amino)-2-(trifluoromethyl)phenyl)piperazine-1-carboxylate

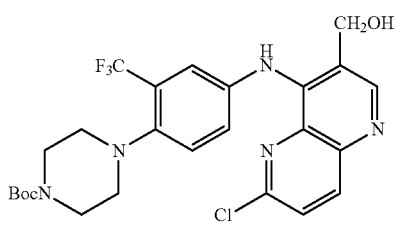 [SMILES: CC(C)(C)OC(=O)N1CCN(c2ccc(Nc3c(CO)cnc4ccc(Cl)nc34)cc2C(F)(F)F)CC1]

Methyl 4-((4-(4-(tert-butoxycarbonyl)piperazin-1-yl)-3-(trifluoromethyl)phenyl)amino)-6-chloro-1,5-naphthyridine-3-carboxylate (0.565 g, 1.0 mmol) was added to ethanol (10 mL), to the system added sodium borohydride (0.228 g, 6 mmol) in batches, stirred at room temperature for 18 h. Ethanol was removed under reduced pressure, added 10 mL of water, and extracted with 80 mL of dichloromethane. The organic layer was dried over anhydrous sodium sulfate, concentrated under reduced pressure to give 0.568 g of a crude solid product. The solid was directly used in the next step.

(3) Preparation of tert-butyl 4-(4-((6-chloro-3-formyl-1,5-naphthyridin-4-yl)amino)-2-(trifluoromethyl)phenyl)piperazine-1-carboxylate

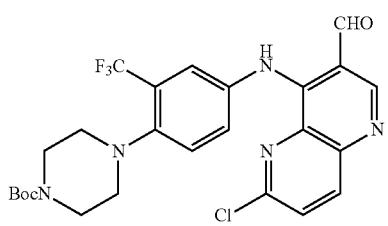 [SMILES: CC(C)(C)OC(=O)N1CCN(c2ccc(Nc3c(C=O)cnc4ccc(Cl)nc34)cc2C(F)(F)F)CC1]

tert-butyl 4-(4-((6-chloro-3-(hydroxymethyl)-1,5-naphthyridin-4-yl)amino)-2-(trifluoromethyl)phenyl) piperazine-1-carboxylate (crude 0.568 g, about 1 mmol) obtained in the above step was dissolved in dichloromethane (10 mL), to the solution added manganese dioxide (2.14 g, 24.6 mmol), and the reaction mixture was stirred at room temperature for 3 h. Filtered, and the solid was washed with 30 mL of dichloromethane. The resulting wash liquid and the filtrate were combined and concentrated, and the resulting solid was subjected to silica gel column chromatography (ethyl acetate: petroleum ether=2:1) to give 0.33 g of a product.

(4) Preparation of tert-butyl 4-(4-((6-chloro-3-((methylamino)methyl)-1,5-naphthyridin-4-yl)amino)-2-(trifluoromethyl)phenyl)piperazine-1-carboxylate

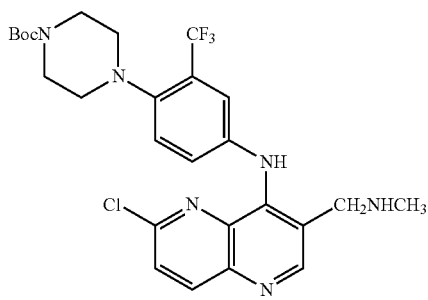

tert-butyl 4-(4-((6-chloro-3-formyl-1,5-naphthyridin-4-yl)amino)-2-(trifluoromethyl)phenyl)piperazine-1-carboxylate (0.223 g, 0.416 mmol) was dissolved in 20 mL of ethanol, added 0.3 mL of a solution of methylamine in ethanol (concentration 27%), and stirred at room temperature for 24 h. After confirming a disappearance of the raw materials by LC-MS, to the system added sodium borohydride (0.09 g, 2.38 mmol), continued stirring at room temperature for 18 h. The reaction was quenched with a saturated aqueous solution of sodium carbonate, concentrated under reduced pressure to remove ethanol, extracted with 100 mL dichloromethane. The organic layer was dried over anhydrous sodium sulfate, concentrated under reduced pressure to give 0.193 g of a solid.

(5) Preparation of tert-butyl 4-(4-(9-chloro-3-methyl-2-oxo-3,4-dihydropyrimido[5,4-c][1,5]naphthyridin-1(2H)-yl)-2-(trifluoromethyl)phenyl)piperazine-1-carboxylate

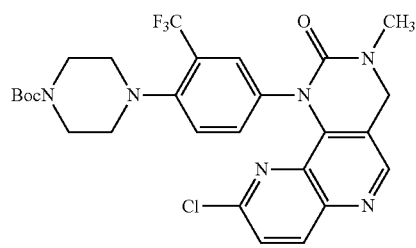 [SMILES: CN1Cc2cnc3ccc(Cl)nc3c2N(c2ccc(N3CCN(C(=O)OC(C)(C)C)CC3)c(C(F)(F)F)c2)C1=O]

tert-butyl 4-(4-((6-chloro-3-((methyl amino)methyl-1,5-naphthyridin-4-yl)amino)-2-(trifluoromethyl)phenyl)piperazine-1-carboxylate (0.452 g, 0.82 mmol) was dissolved in dichloromethane (10 mL), to the reaction flask in an ice bath added triphosgene (0.268 g, 0.90 mmol) and triethylamine (0.38 mL). Then, the mixture was stirred at room temperature for 2 h. The reaction was quenched with a saturated aqueous solution of sodium carbonate, extracted with 80 mL of dichloromethane, the organic layer was dried over anhydrous sodium sulfate, the solvent was removed under reduced pressure, and the resulting 0.473 g of solid was used directly in the next step.

(6) Preparation of tert-butyl 4-(4-(9-(6-methoxy-3-yl)-3-methyl-2-oxo-3,4-dihydropyrimido[5,4-c][1,5]naphthyridin-1(2H)-yl)-2-(trifluoromethyl)phenyl)piperazine-1-carboxylate

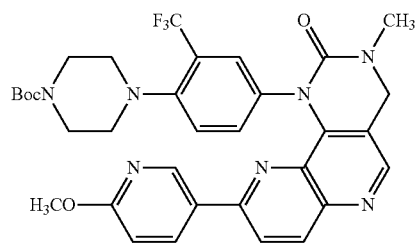 [SMILES: COc1ccc(-c2ccc3ncc4c(c3n2)N(c2ccc(N3CCN(C(=O)OC(C)(C)C)CC3)c(C(F)(F)F)c2)C(=O)N(C)C4)cn1]

tert-butyl 4-(4-(9-chloro-3-methyl-2-oxo-3,4-dihydropyrimido[5,4-c][1,5]naphthyridin-1(2H)-yl)-2-(trifluoromethyl)phenyl)piperazine-1-carboxylate (0.139 g, 0.241 mmol) and 6-methoxy-3-pyridine boronic acid (40.7 mg, 0.266 mmol) were dissolved in toluene (6 mL) and ethanol (2 mL), to the system added tetrakis(triphenylphosphine) palladium (5 mg) and 2N sodium carbonate solution (0.36 mL). Refluxed and reacted under nitrogen for 16 h, cooled to room temperature, filtered, and the organic layer was concentrated under reduced pressure and dissolved in 30 mL of dichloromethane, washed sequentially with water and saturated brine, dried over anhydrous sodium sulfate, concentrated and subjected to silica gel column chromatography (ethyl acetate: petroleum ether=2:1) to give 94.4 mg of the product.

(7) Preparation of 9-(6-methoxypyridin-3-yl)-3-methyl-1-(4-(piperazin-1-yl)-3-(trifluoromethyl)phenyl)-3,4-dihydropyrimido[5,4-c][1,5]naphthyridin-2(1H)-one hydrochloride

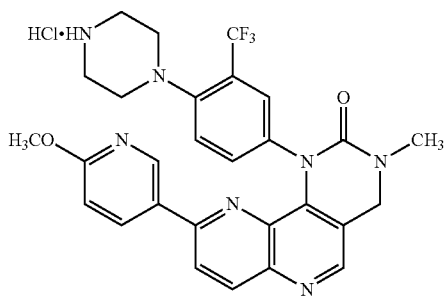

tert-butyl 4-(4-(9-(6-methoxy-3-yl)-3-methyl-2-oxo-3,4-dihydropyrimido[5,4-c][1,5]naphthyridin-1(2H)-yl)-2-(trifluoromethyl)phenyl)piperazine-1-carboxylate (94.4 mg, 0.145 mmol) was dissolved in dichloromethane (10 mL), hydrogen chloride gas was blown to the system for 0.5 h, and a solid was precipitated. The reaction mixture was suction filtered, and the filter cake was washed sequentially with dichloromethane and diethyl ether and dried to give 64 mg of a solid.

Molecular formula: $C_{28}H_{27}ClF_3N_7O_2$; Molecular weight: 586.01; Mass spectrum (M+H): 586.1

$^1$H-NMR (D$_2$O, 400 MHz): δ 8.77-8.65 (1H, m), 8.17 (1H, d), 7.95 (1H, d), 7.94-7.86 (1H, m), 7.48 (1H, s), 7.32-7.21 (3H, m), 6.69-6.58 (1H, m), 4.77 (2H, s), 3.86 (3H, s), 3.25 (4H, t), 3.04 (3H, s), 2.91-2.91 (4H, br s)

Example 8

Preparation of 3-methyl-1-(4-(piperazin-1-yl)-3-(trifluoromethyl)phenyl)-9-(quinolin-3-yl)-3,4-dihydropyrimido[5,4-c][1,5]naphthyridin-2(1H)-one hydrochloride (hydrochloride of Compound 80)

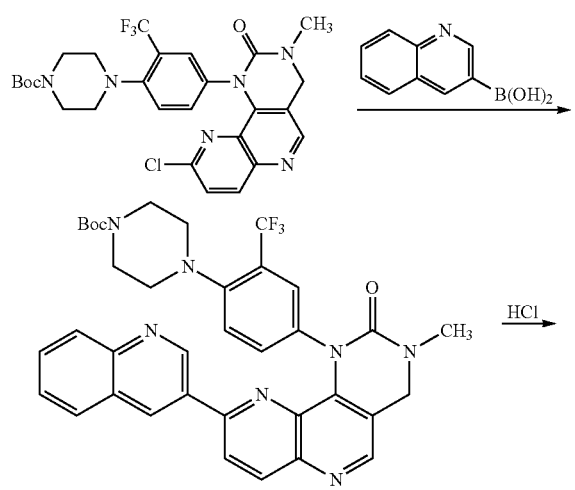

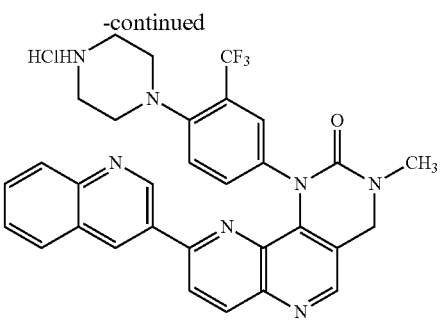

(1) Preparation of tert-butyl 4-(4-(3-methyl-2-oxo-9-(quinolin-3-yl)-3,4-dihydropyrimido[5,4-c][1,5]naphthyridin-1(2H)-yl)-2-(trifluoromethyl)phenyl)piperazine-1-carboxylate

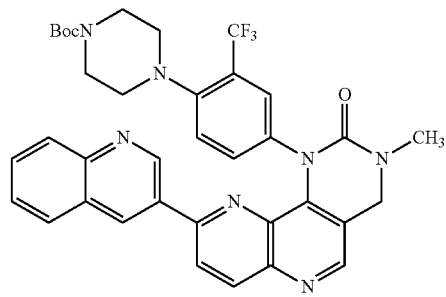 [SMILES: CN1Cc2cnc3ccc(-c4cnc5ccccc5c4)nc3c2N(c2ccc(N3CCN(C(=O)OC(C)(C)C)CC3)c(C(F)(F)F)c2)C1=O]

Specific operations were conducted according to Example 7 (6), using tert-butyl 4-(4-(9-chloro-3-methyl-2-oxo-3,4-dihydropyrimido[5,4-c][1,5]naphthyridin-1(2H)-yl)-2-(trifluoromethyl)phenyl)piperazine-1-carboxylate (0.449 g, 0.779 mmol), to give 331 mg of the product.

(2) Preparation of 3-methyl-1-(4-(piperazin-1-yl)-3-(trifluoromethyl)phenyl)-9-(quinolin-3-yl)-3,4-dihydropyrimido[5,4-c][1,5]naphthyridin-2(1H)-one hydrochloride

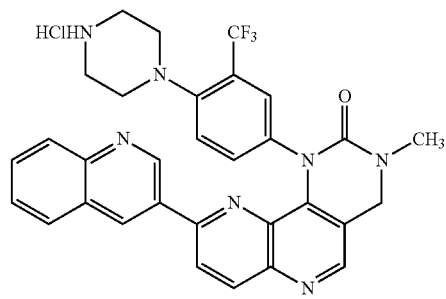

Specific operations were conducted according to Example 7 (7), using tert-butyl 4-(4-(3-methyl-2-oxo-9-(quinolin-3-yl)-3,4-dihydropyrimido[5,4-c][1,5]naphthyridin-1(2H)-yl)-2-(trifluoromethyl)phenyl)piperazine-1-carboxylate (0.331 g, 0.494 mmol), to give 261 mg of a product.

Molecular formula: $C_{31}H_{27}ClF_3N_7O$; Molecular weight: 606.04; Mass spectrum (M+H): 606.1

¹H-NMR (D₂O, 400 MHz): δ8.81 (1H, s), 8.75 (1H, s), 8.64 (1H, s), 8.41 (1H, d), 8.20 (1H, d), 8.13-8.00 (3H, m), 7.90-7.85 (1H, m), 7.70 (1H, dd), 7.45-7.40 (2H, m), 4.82 (2H, s), 3.09 (3H, s), 2.93 (4H, brs), 2.48 (4H, brs)

Example 9

Preparation of (R)-1-(1-(2-hydroxypropanoyl)piperidin-4-yl)-9-(6-methoxypyridin-3-yl)-3-methyl-3,4-dihydropyrimido[5,4-c][1,5]naphthyridin-2(1H)-one (Compound 86)

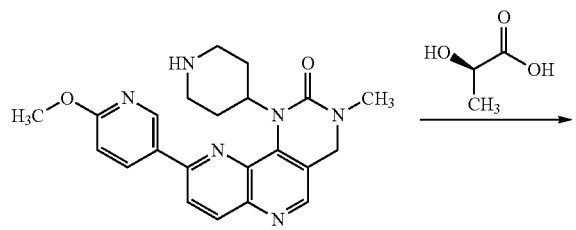

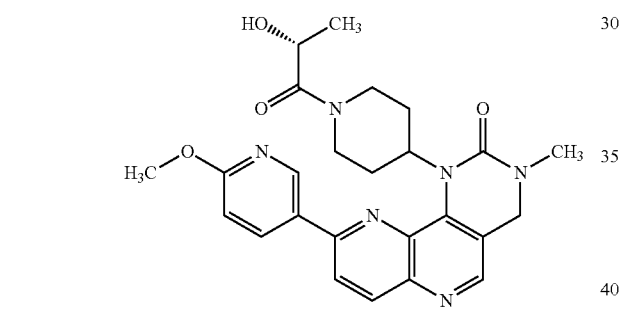

9-(6-methoxypyridin-3-yl)-3-methyl-1-(piperidin-4-yl)-3,4-dihydropyrimido[5,4-c][1,5]naphthyridin-2(1H)-one hydrochloride (hydrochloride of Compound 114 (100 mg, 0.227 mmol)) and triethylamine (0.177 mL) were added to dichloromethane (20 mL), stirred at room temperature for 0.5 h, then to the system sequentially added (R)-lactic acid (26.7 mg, 0.296 mmol), 1-hydroxybenzotriazole (37.8 mg, 0.280 mmol) and 1-ethyl-(3-dimethylaminopropyl)carbodiimide hydrochloride (70.8 mg, 0.37 mmol). The reaction mixture was stirred at room temperature for 2 h. After confirming the reaction was completed by a thin layer chromatography plate (dichloromethane:methanol=10:1), the reaction liquid was washed sequentially with a saturated aqueous solution of sodium carbonate, water and saturated brine, and the organic layer was dried over anhydrous sodium sulfate, concentrated and subjected to silica gel column chromatography (dichloromethane:methanol=10:1) to give 88 mg of a white solid.

Molecular formula: $C_{25}H_{28}N_6O_4$; Molecular weight: 476.53; Mass spectrum (M+H): 477.2

¹H-NMR (CDCl₃, 400 MHz): δ 8.76 (1H, d), 8.59 (1H, s), 8.42 (1H, d), 8.17-8.13 (1H, m), 7.97 (1H, d), 6.91 (1H, d), 5.11-5.01 (1H, m), 4.72 (1H, t), 4.54-4.37 (3H, m), 4.03 (3H, d), 4.00-3.86 (1H, br s), 3.82 (1H, d), 3.06 (3H, s), 2.99-2.68 (3H, m), 2.59-2.30 (2H, m), 2.28-2.10 (1H, m), 1.40 (1.5H, d), 1.27 (1.5H, d)

Example 10

Preparation of 9-(6-methoxypyridin-3-yl)-3-methyl-1-(piperidin-4-yl)-3,4-dihydropyrimido[5,4-c][1,5]naphthyridin-2(1H)-one hydrochloride (hydrochloride of Compound 114)

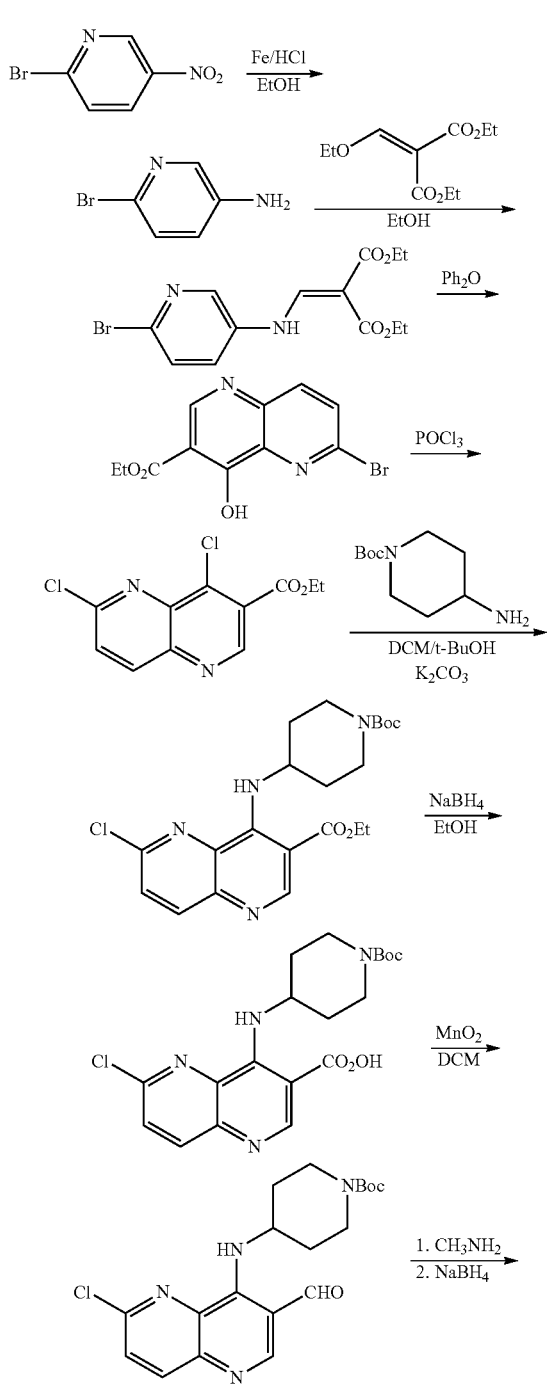

-continued

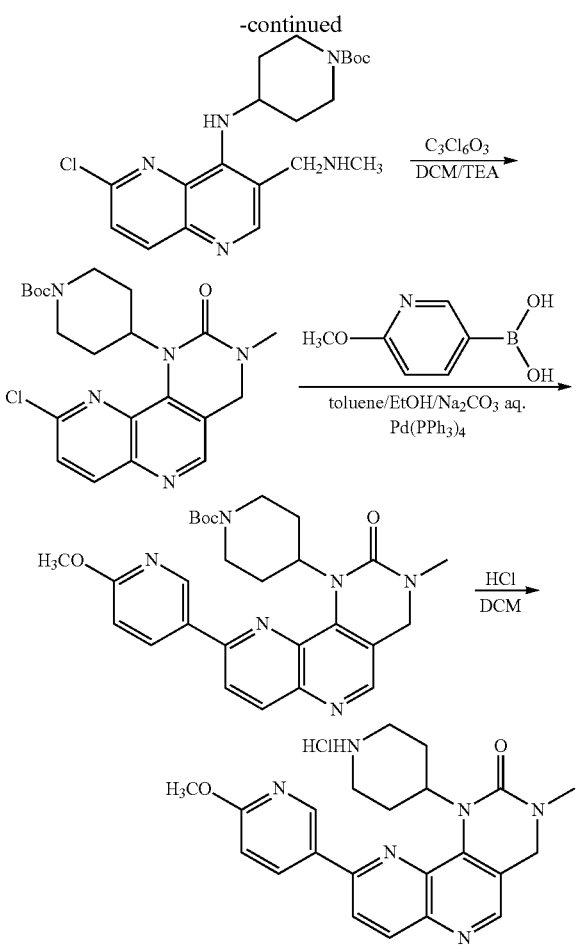

(1) Preparation of 6-bromopyridin-3-amine

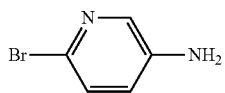

Iron powder (2.8 g, 50 mmol), concentrated hydrochloric acid (1.9 mL) and water (9.1 mL) were sequentially added to a solution of 2-bromo-5-nitropyridine (2.03 g, 10 mmol) in ethanol (48 mL), reacted under reflux for 5 h, cooled, filtered and the filtrate was concentrated, adjusted pH approximately to 7-8 with a saturated aqueous solution of sodium carbonate, and extracted with 100 mL of dichloromethane. The organic layer was dried over anhydrous sodium sulfate, concentrated under reduced pressure to give 1.58 g of a red brown solid.

(2) Preparation of diethyl 2-((((6-bromopyridin-3-yl)amino)methylene)malonate

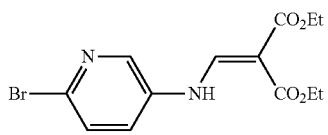

6-bromopyridin-3-amine (40.3 g, 0.233 mol) and diethyl ethoxymethylene malonate (56.5 g, 0.261 mol) were added in 400 mL of ethanol, and reacted under reflux for 5 h, cooled and precipitated a solid. The reaction mixture was suction filtered and the resulting solid was washed with petroleum ether to give 71 g of a pale yellow solid.

(3) Preparation of ethyl 6-bromo-4-hydroxy-1,5-naphthyridine-3-carboxylate

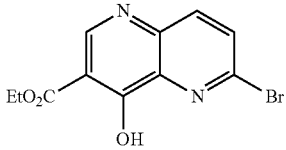 [SMILES: CCOC(=O)c1cnc2ccc(Br)nc2c1O]

Diethyl(2-((((6-bromopyridin-3-yl)amino)methylene)malonate (36 g, 0.105 mol) was added to boiling diphenyl ether (185 mL) in batches over 5 min, and reacted under reflux for 45 min. After confirming a disappearance of the raw materials by a thin layer chromatography plate (ethyl acetate:petroleum ether=1:3), cooled and poured into petroleum ether to precipitate a solid. The reaction mixture was suction filtered to give 17.1 g of a khaki solid.

(4) Preparation of ethyl 4,6-dichloro-1,5-naphthyridine-carboxylate

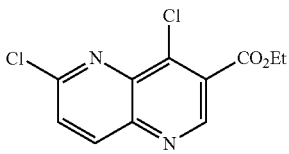 [SMILES: CCOC(=O)c1cnc2ccc(Cl)nc2c1Cl]

Ethyl 6-bromo-4-hydroxy-1,5-naphthyridine-3-carboxylate (15 g, 50.5 mmol) and N,N-dimethylaniline (5 mL) were added to phosphorus oxychloride (50 mL), reacted under refluxed for 3 h, cooled, phosphorus oxychloride was distilled off under reduced pressure, the residue was poured into icewater, adjusted pH approximately to 8 with a saturated aqueous solution of sodium carbonate, and then extracted with 100 mL of dichloromethane. The organic layer was dried over anhydrous sodium sulfate, concentrated and subjected to silica gel column chromatography (petroleum ether:ethyl acetate=3:1) to give 5.1 g of a pale yellow solid (yield 37.3%).

(5) Preparation of ethyl 4-(1-((tert-butoxycarbonyl)piperidin-4-yl)amino)-6-chloro-1,5-naphthyridine-3-carboxylate

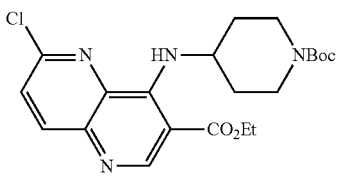

Ethyl 4,6-dichloro-1,5-naphthyridine-3-carboxylate (0.5 g, 1.85 mmol) and tert-butyl 4-aminopiperidine-1-carboxylate (0.45 g, 2.22 mmol) were dissolved in a mixture of dichloromethane (5 mL) and tert-butanol (5 mL). Potassium carbonate was added to the system (0.612 g, 4.43 mmol), and the reaction mixture was stirred at room temperature for 24 h and suction filtrated, the solid was washed with 30 mL of dichloromethane. The washing liquid and the filtrate were combined, concentrated under reduced pressure, and the resulting residue was recrystallized from diethyl ether to give 0.73 g of a pale yellow solid.

(6) Preparation of tert-butyl 4-((6-chloro-3-(hydroxymethyl)-1,5-naphthyridin-4-yl)amino)piperidine-1-carboxylate

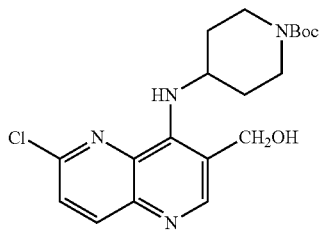 [SMILES: CC(C)(C)OC(=O)N1CCC(Nc2c(CO)cnc3ccc(Cl)nc23)CC1]

Ethyl 4-(1-((tert-butoxycarbonyl)piperidin-4-yl)amino)-6-chloro-1,5-naphthyridine-3-carboxylate (0.43 g, 1.0 mmol) was added to ethanol (10 mL), and to the system added sodium borohydride (0.228 g, 6 mmol) in batches, stirred at room temperature for 18 h. Ethanol was removed under reduced pressure, then added 10 mL of water and extracted with 80 mL of dichloromethane. The organic layer was dried over anhydrous sodium sulfate, concentrated under reduced pressure to give 0.39 g of a solid. The solid was used directly in the next step.

(7) Preparation of tert-butyl 4-((6-chloro-3-formyl-1,5-naphthyridin-4-yl)amino)piperidine-1-carboxylate

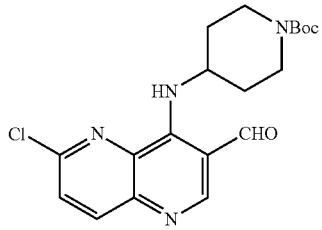 [SMILES: CC(C)(C)OC(=O)N1CCC(Nc2c(C=O)cnc3ccc(Cl)nc23)CC1]

tert-butyl 4-((6-chloro-3-(hydroxymethyl)-1,5-naphthyridin-4-yl)amino)piperidine-1-carboxylate (0.39 g, 1 mmol) was dissolved in dichloromethane (10 mL), and to the solution added manganese dioxide (2.14 g, 32 mmol). The reaction mixture was stirred at room temperature for 3 h, filtered and the solid was washed with 30 mL of dichloromethane. The resulting wash liquid and the filtrate were combined and concentrated, and the resulting solid was recrystallized from methanol to give 0.311 g of a white solid.

(8) Preparation of tert-butyl 4-((6-chloro-3-((methylamino)methyl)-1,5-naphthyridin-4-yl)amino) piperidine-1-carboxylate

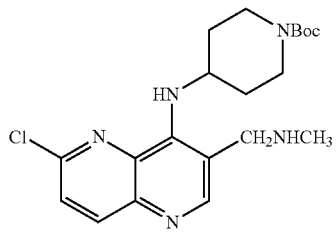

tert-butyl 4-((6-chloro-3-formyl-1,5-naphthyridin-4-yl) amino)piperidine-1-carboxylate (0.31 g, 0.79 mmol) was dissolved in ethanol, added 0.59 mL of a solution of methylamine in ethanol (concentration 27%), stirred at room temperature for 24 h. After confirming a disappearance of the raw materials by LC-MS, to the system added sodium borohydride (0.181 g, 4.60 mmol), continued to stirring at room temperature for 18 h. The reaction was quenched with a saturated aqueous solution of sodium carbonate, concentrated under reduced pressure to remove ethanol, extracted with 100 mL of dichloromethane. The organic layer was dried over anhydrous sodium sulfate and concentrated under reduced pressure to give 0.27 g of a solid (yield 84.2%).

(9) Preparation of tert-butyl 4-(9-chloro-3-methyl-2-oxo-3,4-dihydropyrimido[5,4-c][1,5]naphthyridin-1 (2H)-yl)piperidine-1-carboxylate

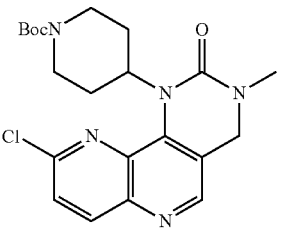 [SMILES: CN1Cc2cnc3ccc(Cl)nc3c2N(C2CCN(C(=O)OC(C)(C)C)CC2)C1=O]

tert-butyl 4-((6-chloro-3-((methylamino)methyl)-1,5-naphthyridin-4-yl)amino)piperidine-1-carboxylate (0.312 g, 0.77 mmol) was dissolved in dichloromethane (10 mL), to the reaction flask in an ice bath added triphosgene (0.274 g, 0.923 mmol) and triethylamine (0.324 mL). The mixture was stirred at room temperature for 2 h. The reaction was quenched with a saturated aqueous solution of sodium carbonate, and extracted with 80 mL of dichloromethane. The organic layer was dried over anhydrous sodium sulfate, and the solvent was removed under reduced pressure to give 0.332 g of a solid. The solid was used directly in the next step.

(10) Preparation of tert-butyl 4-(9-(6-methoxypyridin-3-yl)-3-methyl-2-oxo-3,4-dihydropyrimido[5,4-c][1,5]naphthyridin-1(2H)-yl)piperidine-1-carboxylate

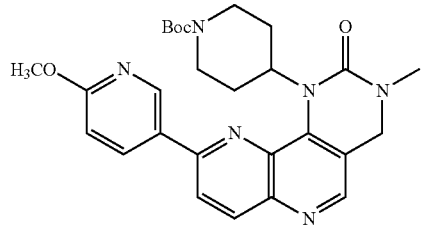 [SMILES: COc1ccc(-c2ccc3ncc4c(c3n2)N(C2CCN(C(=O)OC(C)(C)C)CC2)C(=O)N(C)C4)cn1]

tert-butyl 4-(9-chloro-3-methyl-2-oxo-3,4-dihydropyrimido[5,4-c][1,5]naphthyridin-1(2H)-yl)piperidine-1-carboxylate (0.104 g, 0.241 mmol) and 6-methoxy-3-pyridine boronic acid (40.7 mg, 0.266 mmol) were dissolved in toluene (6 mL) and ethanol (2 mL), and to the system added tetrakis(triphenylphosphine)palladium (5 mg) and 2N sodium carbonate solution (0.36 mL), reacted under reflux under nitrogen for 16 h, cooled to room temperature, filtered and the organic layer was concentrated under reduced pressure and dissolved in 30 mL of dichloromethane, followed by washing sequentially with water and saturated brine, dried over anhydrous sodium sulfate, concentrated and subjected to silica gel column chromatography (ethyl acetate:petroleum ether=2:1) to give 75 mg of the product.

(11) Preparation of 9-(6-methoxypyridin-3-yl)-3-methyl-1-(piperidin-4-yl)-3,4-dihydropyrimido[5,4-c][1,5]naphthyridin-2(1H)-one hydrochloride

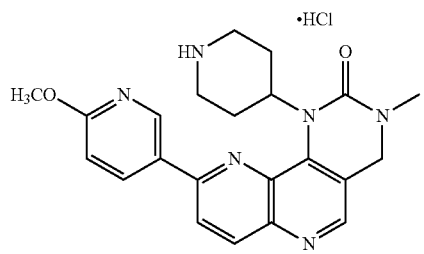 [SMILES: Cl ; COc1ccc(-c2ccc3ncc4c(c3n2)N(C2CCNCC2)C(=O)N(C)C4)cn1]

tert-butyl 4-(9-(6-methoxypyridin-3-yl)-3-methyl-2-oxo-3,4-dihydropyrimido[5,4-c][1,5]naphthyridin-1(2H)-yl)piperidine-1-carboxylate (75 mg, 0.149 mmol) was dissolved in dichloromethane (10 mL), hydrogen chloride gas was blown to the system for 0.5 h, and a solid was precipitated. The reaction mixture was filtered, the filter cake was washed sequentially with dichloromethane and diethyl ether, and the resulting solid was dried to give 50 mg of the titled compound.

Molecular formula: $C_{22}H_{25}ClN_6O_2$; Molecular weight: 440.93; Mass spectrum (M+H): 441.1

$^1$H-NMR (D$_2$O, 400 MHz): δ 8.65 (1H, d), 8.52 (1H, d), 8.34 (1H, d), 8.25-8.20 (1H, m), 8.16 (1H, d), 7.05-7.02 (1H, m), 4.97 (1H, m), 4.56 (2H, s), 3.93 (3H, d), 3.41 (2H, d), 2.98 (3H, s), 2.89-2.67 (4H, m), 2.35 (2H, d)

The invention claimed is:
1. A compound of general formula (I):

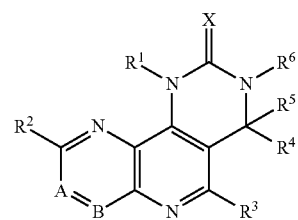

or a pharmaceutically acceptable salt, ester, solvate or stereoisomer thereof,
wherein
X is O or S;
A and B are each CR$^8$, R$^8$ is hydrogen, halogen, cyano, hydroxy, carboxyl, —(CH$_2$)$_n$NR$^{10a}$R$^{10b}$, —(CH$_2$)$_n$C(O)R$^{11}$, —(CH$_2$)$_n$S(O)$_m$R$^{11}$, —(CH$_2$)$_n$S(O)$_m$NR$^{10a}$R$^{10b}$, —(CH$_2$)$_n$N(R$^{10a}$)S(O)$_m$R$^{11}$, —(CH$_2$)$_n$C(O)NR$^{10a}$R$^{10b}$, —(CH$_2$)$_n$OC(O)R$^{11}$, —(CH$_2$)$_n$C(O)(CH$_2$)$_n$OR$^{11}$, —(CH$_2$)$_n$N(R$^{10a}$)C(O)R$^{11}$, C$_{1-6}$ alkyl or C$_{1-6}$ alkoxy, wherein C$_{1-6}$ alkyl and C$_{1-6}$ alkoxy may be optionally substituted with 1 to 3 substituents selected from halogen, hydroxy and carboxyl;
R$^1$ is (trifluoromethyl)phenyl;
R$^2$ is hydrogen, C$_{1-6}$ alkyl, C$_{2-8}$ alkenyl, C$_{2-8}$ alkynyl, C$_{3-8}$ cycloalkyl, 6- to 14-membered aryl, 5- to 14-membered heteroaryl, 3- to 14-membered heterocyclic group, 7- to 12-membered spirocyclic group or 7- to 12-membered endocyclic group, all of which except hydrogen may be optionally substituted with 1 to 5 R$^{9b}$;
R$^3$ is hydrogen, carboxyl or C$_{1-6}$ alkyl, wherein C$_{1-6}$ alkyl may be optionally substituted with 1 to 3 substituents selected from halogen, hydroxy and carboxyl;
R$^4$ and R$^5$ are each independently hydrogen or C$_{1-6}$ alkyl, wherein C$_{1-6}$ alkyl may be optionally substituted with 1 to 3 substituents selected from halogen, hydroxy and carboxyl; or R$^4$ and R$^5$ combine each other to form C$_{3-8}$ cycloalkyl, 5- to 6-membered monocyclic heteroaryl or 5- to 6-membered monocyclic heterocyclic group;
R$^6$ is hydrogen or C$_{1-6}$ alkyl, wherein C$_{1-6}$ alkyl may be optionally substituted with 1 to 3 substituents selected from halogen, hydroxy and carboxyl;
R$^{9b}$ is
(1) halogen, cyano, hydroxy, —(CH$_2$)$_n$NR$^{10a}$R$^{10b}$, —(CH$_2$)$_n$C(O)R$^{11}$, —(CH$_2$)$_n$S(O)$_m$R$^{11}$, —(CH$_2$)$_n$S(O)$_m$NR$^{10a}$R$^{10b}$, —(CH$_2$)$_n$N(R$^{10a}$)S(O)$_m$R$^{11}$, —(CH$_2$)$_n$C(O)NR$^{10a}$R$^{10b}$, —(CH$_2$)$_n$OC(O)R$^{11}$, —(CH$_2$)$_n$C(O)(CH$_2$)$_n$OR$^{11}$, —(CH$_2$)$_n$N(R$^{10a}$)C(O)R$^{11}$;
(2) C$_{1-6}$ alkyl, C$_{2-8}$ alkenyl, C$_{2-8}$ alkynyl or C$_{1-6}$ alkoxy, all of which may be optionally substituted with 1 to 3 substituents selected from halogen, hydroxy and cyano;
(3) C$_{3-8}$ cycloalkyl, 6- to 14-membered aryl, 5- to 14-membered heteroaryl or 3- to 14-membered heterocyclic group, all of which may be optionally substituted with 1 to 3 substituents selected from halogen, hydroxy, cyano, trifluoromethyl, C$_{1-6}$ alkyl, C$_{2-8}$ alkenyl, C$_{2-8}$ alkynyl, C$_{1-6}$ alkoxy, —(CH$_2$)$_n$NR$^{10a}$R$^{10b}$, —(CH$_2$)$_n$C(O)R$^{11}$, —(CH$_2$)$_n$C(O)NR$^{10a}$R$^{10b}$, —(CH$_2$)$_n$S(O)$_m$R$^{11}$, —(CH$_2$)$_n$S(O)$_m$NR$^{10a}$R$^{10b}$, —(CH$_2$)$_n$N(R$^{10a}$)S(O)$_m$R$^{11}$, —(CH$_2$)$_n$OC(O)R$^{11}$ and —(CH$_2$)$_n$N(R$^{10a}$)C(O)R$^{11}$;

$R^{10a}$ and $R^{10b}$ are each independently hydrogen, $C_{1-6}$ alkyl, $C_{3-8}$ cycloalkyl, 6- to 14-membered aryl, 5- to 14-membered heteroaryl or 3- to 14-membered heterocyclic group, all of which except hydrogen may be optionally substituted with 1 to 3 substituents selected from hydroxy, halogen, cyano, carboxyl, —$(CH_2)_nNR^{10a}R^{10b}$, sulfamoyl, carbamoyl and sulfamino;

$R^{11}$ is hydrogen, $C_{1-6}$ alkyl or $C_{1-6}$ alkoxy, wherein $C_{1-6}$ alkyl and $C_{1-6}$ alkoxy may be optionally substituted with 1 to 3 substituents selected from halogen, cyano, hydroxy, carboxyl, —$(CH_2)_nNR^{10a}R^{10b}$, sulfamoyl and carbamoyl;

m is 0, 1 or 2; and n is 0-4.

2. The compound of claim 1, or a pharmaceutically acceptable salt, ester, solvate or stereoisomer thereof, wherein $R^8$ is hydrogen, halogen, cyano, hydroxy, carboxyl, —$(CH_2)_nNR^{10a}R^{10b}$, —$(CH_2)_nS(O)_mNR^{10a}R^{10b}$, —$(CH_2)_nN(R^{10a})S(O)_mR^{11}$, $C_{1-6}$ alkyl or $C_{1-6}$ alkoxy, wherein $C_{1-6}$ alkyl and $C_{1-6}$ alkoxy may be optionally substituted with 1 to 3 substituents selected from halogen, hydroxy and carboxyl;

$R^1$ is (trifluoromethyl)phenyl $R^2$ is $C_{3-8}$ cycloalkyl, 6- to 10-membered aryl, 5- to 10-membered heteroaryl or 5- to 10-membered heterocyclic group, all of which may be optionally substituted with 1 to 3 $R^{9b}$;

$R^3$, $R^4$, $R^5$ and $R^6$ are each independently hydrogen or $C_{1-6}$ alkyl, wherein $C_{1-6}$ alkyl may be optionally substituted with 1 to 3 substituents selected from halogen, hydroxy and carboxyl;

$R^{9b}$ is (1) halogen, cyano, hydroxy, —$(CH_2)_nNR^{10a}R^{10b}$, —$(CH_2)_nC(O)R^{11}$, —$(CH_2)_nS(O)_mR^{11}$, —$(CH_2)_nS(O)_mNR^{10a}R^{10b}$, —$(CH_2)_nN(R^{10a})S(O)_mR^{11}$, —$(CH_2)_nC(O)NR^{10a}R^{10b}$, —$(CH_2)_nOC(O)R^{11}$, —$(CH_2)_nC(O)(CH_2)_nOR^{11}$, —$(CH_2)_nN(R^{10a})C(O)R^{11}$;

(2) $C_{1-6}$ alkyl or $C_{1-6}$ alkoxy, all of which may be optionally substituted with 1 to 3 substituents selected from halogen, hydroxy and cyano;

(3) $C_{3-8}$ cycloalkyl, 6- to 10-membered aryl, 5- to 10-membered heteroaryl or 5- to 10-membered heterocyclic group, all of which may be optionally substituted with 1 to 3 substituents selected from halogen, hydroxy, cyano, trifluoromethyl, $C_{1-6}$ alkyl, $C_{1-6}$ alkoxy, —$(CH_2)_nNR^{10a}R^{10b}$, —$(CH_2)_nC(O)R^{11}$, —$(CH_2)_nC(O)NR^{10a}R^{10b}$, —$(CH_2)_nS(O)_mR^{11}$, —$(CH_2)_nS(O)_mNR^{10a}R^{10b}$, —$(CH_2)_nN(R^{10a})S(O)_mR^{11}$ and —$(CH_2)_nN(R^{10a})C(O)R^{11}$;

$R^{10a}$ and $R^{10b}$ are each independently hydrogen or $C_{1-6}$ alkyl, wherein $C_{1-6}$ alkyl may be optionally substituted with 1 to 3 substituents selected from hydroxy, halogen, cyano, carboxyl, —$(CH_2)_nNR^{10a}R^{10b}$, sulfamoyl, carbamoyl and sulfamino; and $R^{11}$ is hydrogen or $C_{1-6}$ alkyl, wherein $C_{1-6}$ alkyl may be optionally substituted with 1 to 3 substituents selected from halogen, cyano, hydroxy, carboxyl, —$NR^{10a}R^{10b}$, sulfamoyl and carbamoyl.

3. The compound of claim 2, or a pharmaceutically acceptable salt, ester, solvate or stereoisomer thereof, wherein X is O;

A and B are each CH;

$R^1$ is (trifluoromethyl)phenyl;

$R^2$ is 6- to 10-membered aryl, 5- to 6-membered monocyclic heteroaryl, 9- to 10-membered fused heteroaryl, 5- to 6-membered monocyclic heterocyclic group or 9- to 10-membered fused heterocyclic group, all of which may be optionally substituted with 1 to 3 $R^{9b}$;

$R^3$, $R^4$ and $R^5$ are each hydrogen;

$R^6$ is hydrogen or $C_{1-6}$ alkyl;

$R^{9b}$ is (1) halogen, cyano, hydroxy, —$(CH_2)_nNR^{10a}R^{10b}$, —$(CH_2)_nC(O)R^{11}$, —$(CH_2)_nS(O)_mR^{11}$, —$(CH_2)_nS(O)_mNR^{10a}R^{10b}$, —$(CH_2)_nN(R^{10a})S(O)_mR^{11}$, —$(CH_2)_nC(O)NR^{10a}R^{10b}$, —$(CH_2)_nOC(O)R^{11}$, —$(CH_2)_nC(O)(CH_2)_nOR^{11}$, —$(CH_2)_nN(R^{10a})C(O)R^{11}$;

(2) $C_{1-6}$ alkyl or $C_{1-6}$ alkoxy, all of which may be optionally substituted with 1 to 3 substituents selected from halogen, hydroxy and cyano;

(3) 5- to 10-membered heteroaryl or 5- to 10-membered heterocyclic group, all of which may be optionally substituted with 1 to 3 substituents selected from halogen, hydroxy, cyano, trifluoromethyl, $C_{1-6}$ alkyl, $C_{1-6}$ alkoxy, —$(CH_2)_nNR^{10a}R^{10b}$, —$(CH_2)_nC(O)R^{11}$, —$(CH_2)_nC(O)NR^{10a}R^{10b}$, —$(CH_2)_nS(O)_mR^{11}$, —$(CH_2)_nS(O)_mNR^{10a}R^{10b}$, —$(CH_2)_nN(R^{10a})S(O)_mR^{11}$, —$(CH_2)_nOC(O)R^{11}$ and —$(CH_2)_nN(R^{10a})C(O)R^{11}$;

$R^{10a}$ and $R^{10b}$ are each independently hydrogen or $C_{1-6}$ alkyl;

$R^{11}$ is hydrogen or $C_{1-6}$ alkyl, wherein $C_{1-6}$ alkyl may be optionally substituted with 1 to 3 substituents selected from halogen, cyano, hydroxyl and —$(CH_2)_nNR^{10a}R^{10b}$; and n is 0-3.

4. The compound of claim 3, or a pharmaceutically acceptable salt, ester, solvate or stereoisomer thereof, wherein $R^1$ is (trifluoromethyl)phenyl;

$R^2$ is 6- to 10-membered aryl, 5- to 6-membered monocyclic heteroaryl or 9- to 10-membered fused heteroaryl, all of which may be optionally substituted with 1 to 3 $R^{9b}$; and $R^{9b}$ is (1) halogen, cyano, hydroxy, —$(CH_2)_nNR^{10a}R^{10b}$, —$(CH_2)_nN(R^{10a})C(O)R^{11}$, —$(CH_2)_nC(O)R^{11}$, —$(CH_2)_nS(O)_mR^{11}$, —$(CH_2)_nC(O)NR^{10a}R^{10b}$, —$(CH_2)_nC(O)(CH_2)_nOR^{11}$;

(2) $C_{1-6}$ alkyl or $C_{1-6}$ alkoxy, all of which may be optionally substituted with 1 to 3 substituents selected from halogen, hydroxy and cyano;

(3) 5- to 6-membered monocyclic heteroaryl or 5- to 6-membered monocyclic heterocyclic group, all of which may be optionally substituted with 1 to 3 substituents selected from halogen, hydroxy, cyano, trifluoromethyl, $C_{1-6}$ alkyl, $C_{1-6}$ alkoxy, —$(CH_2)_nNR^{10a}R^{10b}$, —$(CH_2)_nC(O)R^{11}$, —$(CH_2)_nC(O)NR^{10a}R^{10b}$, —$(CH_2)_nOC(O)R^{11}$ and —$(CH_2)_nN(R^{10a})C(O)R^{11}$.

5. The compound of claim 4, or a pharmaceutically acceptable salt, ester, solvate or stereoisomer thereof, wherein $R^1$ is (trifluoromethyl)phenyl;

$R^2$ is phenyl, pyridyl, pyrimidinyl, thienyl, pyrazolyl, indazolyl, indolyl, pyridopyrrolyl, pyrazolopyridyl or quinolyl, all of which may be optionally substituted with 1 to 3 $R^{9b}$;

$R^{9b}$ is (1) cyano, hydroxy, —$NR^{10a}R^{10b}$, —$N(R^{10a})C(O)R^{11}$, —$C(O)R^{11}$, —$S(O)_mR^{11}$, —$C(O)NR^{10a}R^{10b}$, —$C(O)CH_2OR^{11}$;

(2) $C_{1-6}$ alkyl or $C_{1-6}$ alkoxy, all of which may be optionally substituted with 1 to 3 substituents selected from halogen, hydroxy and cyano;

(3) pyrrolyl, pyrazolyl, imidazolyl, piperidinyl, piperazinyl or morpholinyl, all of which may be optionally substituted with 1 to 3 substituents selected from halogen, hydroxy, cyano, trifluoromethyl, $C_{1-6}$ alkyl, $C_{1-6}$ alkoxy, —$NR^{10a}R^{10b}$, —$C(O)R^{11}$, —$C(O)NR^{10a}R^{10b}$, —$OC(O)R^{11}$, —$N(R^{10a})C(O)R^{11}$;

$R^{11}$ is hydrogen or $C_{1-6}$ alkyl, wherein $C_{1-6}$ alkyl may be optionally substituted with 1 to 3 substituents selected from halogen, cyano and hydroxy; and n is 0.

6. The compound of claim 1, or a pharmaceutically acceptable salt, ester, solvate or stereoisomer thereof, which is selected from the following compounds:

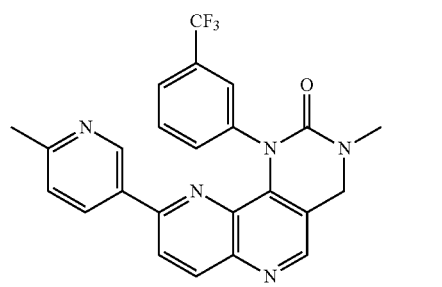
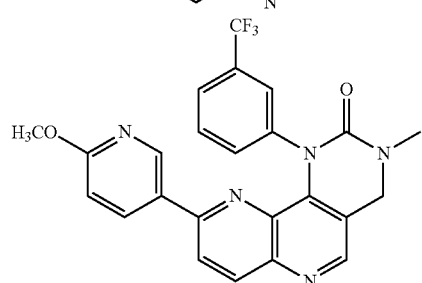
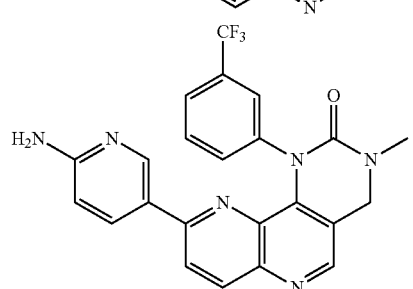
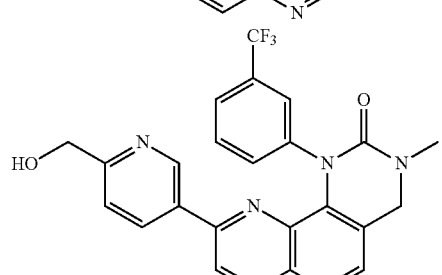
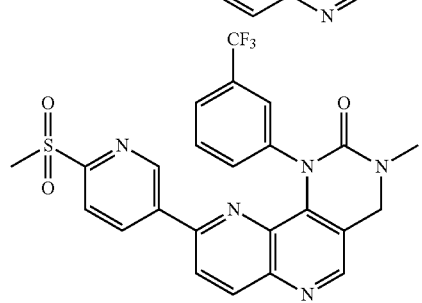

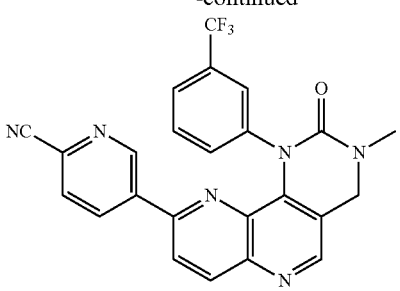

-continued

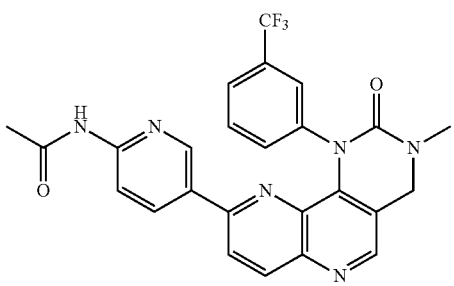
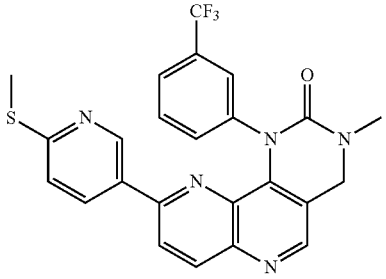
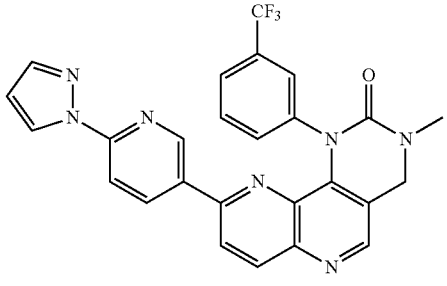
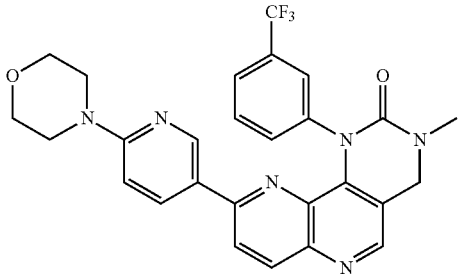
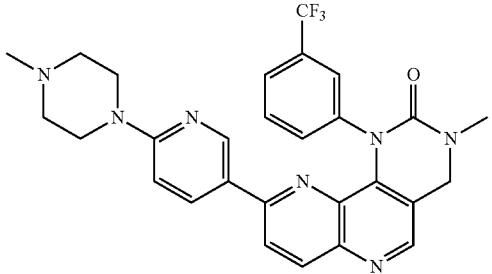

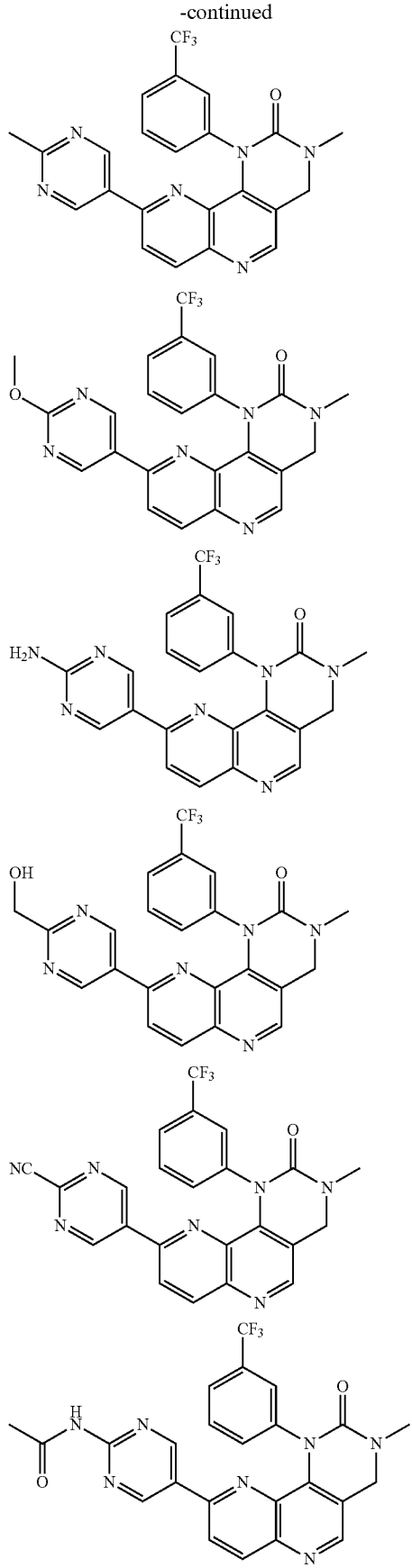
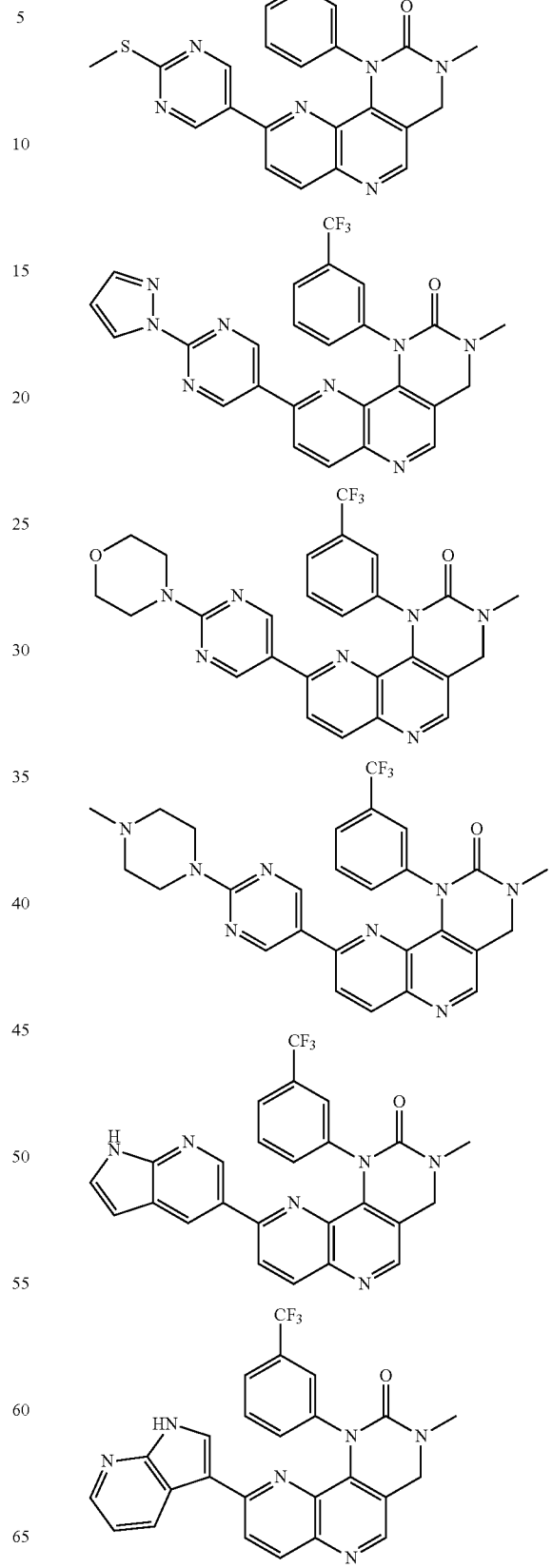

-continued

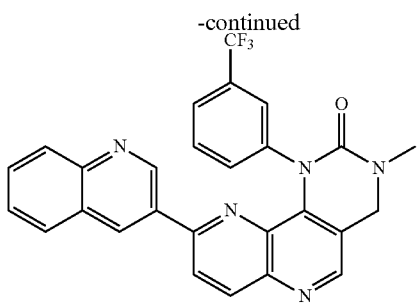

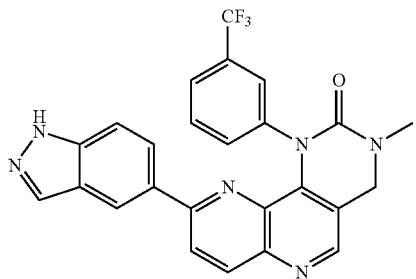

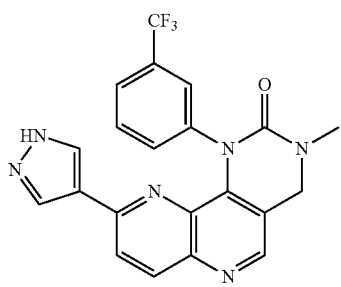

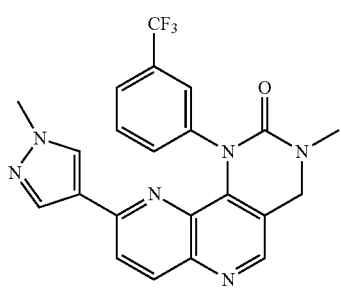

-continued

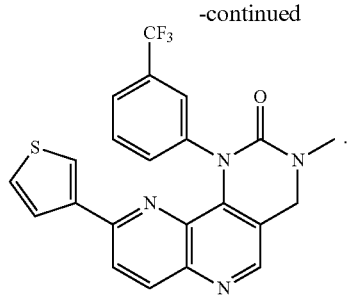

7. A pharmaceutical composition comprising the compound of claim 1, a pharmaceutically acceptable salt, ester, solvate or stereoisomer thereof and one or more pharmaceutically acceptable carriers, further comprising one or more antitumor agents and immunosuppressants, wherein the antitumor agents and immunosuppressive agents are
  (1) anti-metabolites selected from the group consisting of capecitabine, gemcitabine and pemetrexed disodium;
  (2) growth factor inhibitors selected from the group consisting of pazopanib, imatinib, erlotinib, lapatinib, gefitinib and vandetanib;
  (3) antibodies selected from the group consisting of Herceptin and Avastin;
  (4) mitotic inhibitors selected from the group consisting of paclitaxel, vinorelbine, docetaxel and doxorubicin;
  (5) anti-tumor hormones selected from the group consisting of letrozole, tamoxifen, fulvestrant, flutamide and triptorelin;
  (6) alkylating agents selected from the group consisting of cyclophosphamide, nitrogen mustard, melphalan, chlorambucil and carmustine;
  (7) platinum metals selected from the group consisting of carboplatin, cisplatin and oxaliplatin;
  (8) topoisomerase inhibitors selected from the group consisting of camptothecin, topotecan and irinotecan;
  (9) immunosuppressants selected from the group consisting of everolimus, sirolimus and temsirolimus;
  (10) purine analogues selected from the group consisting of 6-mercaptopurine, 6-thioguanine and azathioprine;
  (11) antibiotics selected from the group consisting of streptozotocin D, daunorubicin, doxorubicin, mitoxantrone, bleomycin and plicamycin; or
  (12) adrenal cortex inhibitor which is aminoglutethimide.

8. A method for treating a proliferative disease, comprising administering to a patient a therapeutically effective amount of the compound of claim 1, a pharmaceutically acceptable salt, ester, solvate or stereoisomer thereof, wherein the proliferative disease is selected from brain or ovarian cancer.

* * * * *